(12) United States Patent
Wu et al.

(10) Patent No.: US 9,234,176 B2
(45) Date of Patent: Jan. 12, 2016

(54) CHEMICALLY DEFINED PRODUCTION OF CARDIOMYOCYTES FROM PLURIPOTENT STEM CELLS

(71) Applicant: The Board of Trustees of the Leland Stanford Junior University, Palo Alto, CA (US)

(72) Inventors: Joseph Wu, Stanford, CA (US); Robert C. Robbins, Stanford, CA (US); Paul W. Burridge, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 48 days.

(21) Appl. No.: 14/079,312

(22) Filed: Nov. 13, 2013

(65) Prior Publication Data

US 2014/0134733 A1 May 15, 2014

Related U.S. Application Data

(60) Provisional application No. 61/725,907, filed on Nov. 13, 2012.

(51) Int. Cl.
*C12N 5/00* (2006.01)
*C12N 5/02* (2006.01)
*C12N 5/071* (2010.01)
*C12N 5/077* (2010.01)

(52) U.S. Cl.
CPC .......... *C12N 5/0657* (2013.01); *C12N 2500/38* (2013.01); *C12N 2501/415* (2013.01); *C12N 2501/727* (2013.01); *C12N 2506/02* (2013.01); *C12N 2506/45* (2013.01)

(58) Field of Classification Search
CPC .................................................. C12N 5/0657
USPC ......................................................... 435/377
See application file for complete search history.

(56) References Cited

U.S. PATENT DOCUMENTS

| | | | |
|---|---|---|---|
| 7,425,448 B2 | 9/2008 | Xu | |
| 7,763,464 B2 | 7/2010 | Xu | |
| 7,897,389 B2 | 3/2011 | Gold et al. | |
| 8,158,421 B2 | 4/2012 | Passier et al. | |
| 2002/0076747 A1 | 6/2002 | Price et al. | |
| 2008/0254003 A1 | 10/2008 | Passier et al. | |
| 2011/0097799 A1 | 4/2011 | Stankewicz et al. | |
| 2011/0142935 A1 | 6/2011 | Kamp et al. | |
| 2012/0129211 A1 | 5/2012 | Kattman et al. | |
| 2013/0189785 A1 * | 7/2013 | Palecek et al. | 435/377 |

FOREIGN PATENT DOCUMENTS

| | | | |
|---|---|---|---|
| WO | WO2010101849 A1 | 9/2010 | |
| WO | WO 2010101849 A1 * | 9/2010 | |
| WO | WO2011160128 A2 | 12/2011 | |

OTHER PUBLICATIONS

Shiraki et al, Genes to Cells, 13:731-746, 2008.*
Pucéat, Methods, 45: 168-171, 2008.*
Wobus et al. (1997) J MoL Cell Cardiology 29:1525.*
Schuldiner (2000) PNAS 97:11307.*
Tohyama (2011, Circulation, Abstract 12671, 124:A12671.*
Paige (PLoSONE, 2010, 5:e1 1134, pp. 1-8.*
Naito (2006, PNAS, 103:19812-19817.*
Claassen (2009, Mol Reprod Dev, 76:722-733.*
Kramer et al. (2000) Mech. of Dev. 92:193-205.*
Burridge et al., "Improved Human Embryonic Stem Cell Embryoid Body Homogeneity and Cardiomyocyte Differentiation from a Novel V-96 Plate Aggregation System Highlights Interline Variability", Stem Cells (2007), 25:929-938.
Burridge et al., "A Universal System for Highly Efficient Cardiac Differentiation of Human Induced Pluripotent Stem Cells That Eliminates Interline Variability", PLoS ONE (2011), 6(4):e18293.
Burridge et al., "Production of De Novo Cardiomyocytes: Human Pluripotent Stem Cell Differentiation and Direct Reprogramming", Cell Stem Cell (2012), 10(1):16-28.
Gonzalez et al., "Stepwise chemically induced cardiomyocyte specification of human embryonic stem cells", Angew Chem Int Ed Engl (2011), 50(47):11181-11185.
Honda et al., "Electrophysiological Characterization of Cardiomyocytes Derived From Human Induced Pluripotent Stem Cells", J Pharmacol Sci (2011), 117:149-159.
Kim et al., "Non-Cardiomyocytes Influence the Electrophysiological Maturation of Human Embryonic Stem Cell-Derived Cardiomyocytes During Differentiation", Stem Cells and Dev (2010), 19(6):783-795.
Laflamme et al., "Cardiomyocytes derived from human embryonic stem cells in pro-survival factors enhance function of infarcted rat hearts", Nature Biotechnol (2007), 25:1015-1024.
Lian et al., "Robust cardiomyocyte differentiation from human pluripotent stem cells via temporal modulation of canonical Wnt signaling", Proc Natl Acad Sci USA (2012), 109(27):E1848-E1857.
Ren et al., "Small Molecule Wnt Inhibitors Enhance the Efficiency of BMP-4-Directed Cardiac Differentiation of Human Pluripotent Stem Cells", J Mol Cell Cardiol (2011), 51(3):280-287.
Willems et al., "Small molecule inhibitors of the Wnt pathway potently promote cardiomyocytes from human embryonic stem cell derived mesoderm", Circ Res (2011), 109(4):360-364.
Watanabe et al., "A ROCK inhibitor permits survival of dissociated human embryonic stem cells", Nat Biotechnol (2007), 25(6):681-686.

* cited by examiner

*Primary Examiner* — Valarie Bertoglio
(74) *Attorney, Agent, or Firm* — Bozicevic, Field & Francis LLP; Pamela Sherwood

(57) ABSTRACT

Methods are provided for producing a cardiomyocyte population from a mammalian pluripotent stem cell population. Aspects of the methods include using a Wnt signaling agonist and antagonist, each in minimal media, to modulate Wnt signaling. Also provided are kits for practicing the methods described herein.

16 Claims, 12 Drawing Sheets
(8 of 12 Drawing Sheet(s) Filed in Color)

| d0 | d1 | d2 | d3 | d4 | d5 | Relative efficiency | % TNNT2⁺ |
|---|---|---|---|---|---|---|---|
| GSK3βi | | WNTi | | Δ | | - | |
| GSK3βi | | WNTi | | Δ | Δ | - | |
| GSK3βi | WNTi | Δ | | Δ | | ++ | 56.2±10.3 |
| GSK3βi | WNTi | Δ | Δ | Δ | | + | 12.2±5.6 |
| GSK3βi | WNTi | | Δ | | Δ | ++ | 59.2±7.9 |
| GSK3βi | | Δ | | WNTi | | +++ | 68.4±16.6 |
| GSK3βi | | Δ | | WNTi | Δ | +++ | 67.2±9.4 |
| GSK3βi | | Δ | | Δ | WNTi | - | |
| GSK3βi | Δ | | WNTi | | Δ | ++ | 60.7±7.9 |
| GSK3βi | Δ | WNTi | | Δ | | ++ | 58.4±12.4 |
| GSK3βi | Δ | WNTi | | Δ | Δ | ++ | 60.1±15.4 |
| GSK3βi | Δ | | Δ | | WNTi | - | |
| GSK3βi | Δ | Δ | | WNTi | | ++ | 40.1±20.2 |
| GSK3βi | Δ | Δ | | WNTi | Δ | + | 30.7±12.4 |
| GSK3βi | Δ | Δ | Δ | | WNTi | - | |
| | GSK3βi | | WNTi | | Δ | ++++ | 84.1±9.1 |
| | GSK3βi | WNTi | | Δ | | ++++ | 86.1±10.0 |
| | GSK3βi | WNTi | | Δ | Δ | ++++ | 78.0±9.8 |
| | GSK3βi | | Δ | | WNTi | - | |
| | GSK3βi | Δ | | WNTi | | +++ | 65.4±5.6 |
| | GSK3βi | Δ | WNTi | | Δ | +++ | 61.1±13.2 |
| | GSK3βi | Δ | Δ | | WNTi | - | |

Application of small molecule inhibitors on day of differentiation

Figure 11

CHEMICALLY DEFINED PRODUCTION OF CARDIOMYOCYTES FROM PLURIPOTENT STEM CELLS

GOVERNMENT RIGHTS

This invention was made with government support under contracts HL099776 and HL089027 awarded by the National Institutes of Health. The Government has certain rights in the invention.

BACKGROUND OF THE INVENTION

Stem cells are capable of self-renewal and can differentiate into specialized cell types. Pluripotent stem cells, such as those found in the embryo, retain the potential to differentiate into any cell type of the organism. The ability to culture pluripotent stem cells has created enormous research and therapeutic potential. For example, directing the differentiation of stem cells to grow desired cell types, tissues, and organs could provide an unprecedented tool in the clinic by providing a means for transplantation and/or repair of damaged tissues and organs, such as cardiac muscle. Directed differentiation of stem cells would also provide an inexhaustible supply of cells for drug screens and for the exploration of fundamental questions of basic research. The advent of induced pluripotent stem cell technology, which facilitates the derivation of pluripotent stem cells from differentiated adult cells, further opened the door for the exploitation of patient-derived pluripotent stem cells to achieve personalized medicine.

Cardiomyocytes are the muscle cells of the heart and can be produced in vitro by directing the differentiation of pluripotent stem cells. Cardiomyocytes produced in culture exhibit features in common with those isolated from heart tissue. Namely, cardiomyocytes in culture begin to spontaneously beat and do so in a synchronized manner. The ability to produce beating cardiomyocytes in culture has far reaching implications for the clinic, including the repair of damage caused by myocardial infarction.

Secreted Wnt glycoproteins form a family of signaling molecules that trigger the highly conserved Wnt signaling pathway, which regulates numerous cell-to-cell interactions during embryogenesis and throughout adult life. The Wnt signaling pathway controls several aspects of cellular behavior, including cell differentiation, cell growth, cell proliferation, cell survival, morphogenesis, organogenesis, and tissue patterning. Controlled timing and levels of Wnt signaling are crucial for several facets of proper heart development, including the differentiation of cardiomyocytes and cardiomyocyte progenitors. As such, the directed differentiation of cardiomyocytes from pluripotent stem cells in vitro can be achieved by temporal control of the Wnt signaling pathway.

The production of cardiomyocytes produced from pluripotent stem cells for use in therapy and/or research will benefit from reduced cost, increased efficiency, increased reproducibility, increased flexibility (successful implementation using multiple different stem cell lines), increased scalability, and increased availability of essential components. The present invention addresses these needs.

Publications

Publications of interest include Laflamme et al., Nat Biotechnol. 2007 September; 25 (9):1015-24; Willems at al., Circ Res. 2011 August 5; 109 (4):360-4; Ren at al., J Mol Cell Cardiol. 2011 September; 51 (3):280-7; Burridge et al., Cell Stem Cell. 2012 January 6; 10 (1):16-28; Gonzalez at al., Angew Chem Int Ed Engl. 2011 November 18; 50 (47): 11181-5; and Lian et al., Proc Natl Acad Sci USA. 2012 July 3:109 (27):E1848-57.

SUMMARY OF THE INVENTION

Methods are provided for producing a cardiomyocyte population from a mammalian pluripotent stem cell population. In the methods of the invention the mammalian pluripotent stem cell population is contacted with an effective amount of a Wnt signaling agonist in a minimal media for a period of about 12-60 hours, to produce an agonist-contacted cell population; and the agonist-contacted cell population with an effective amount of a Wnt signaling antagonist in a minimal media for a period of at least 12 hours. Pluripotent stem cells of interest include embryonic stem cells and induced pluripotent stem cells.

In some embodiments of the invention the Wnt signaling agonist is an inhibitor of GSK-3β, which may include, without limitation, BIO, CHIR-99021, or a combination thereof. In some embodiments the Wnt signaling antagonist is a compound selected from the group consisting of: C59, IWR-1, IWP-2, IWP-4, XAV-939, and combinations thereof.

The presence of cardiomyocytes may be confirmed by various methods known in the art, including for example determining a cardiomyocyte electrophysiological profile, determining responsiveness to known cardioactive drugs, contacting the cell population with an antibody specific for a cardiomyocyte marker protein, and determining the percentage of cells positive for expression, etc.

Kits for practicing the methods of the invention are also included, and generally include defined medium, a Wnt signaling agonist, and a Wnt signaling antagonist. Kits may also include reagents useful in detecting the presence of cardiomyocytes.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

FIG. 11: Timing of Wnt signaling modulation on cardiac differentiation efficiency, and effect of inhibition of pathways associated with mesoderm induction and specification. a) Time points for the addition of CHIR99021 and Wnt-C59 were modified as shown. Percentage of $TNNT2_+$ cells was measured at day 15 using flow cytometry; –, 0-10% $TNNT2^+$; +, 10-60% $TNNT2^+$; ++, 60-65% $TNNT2^+$; +++, 65-75% $TNNT2^+$; ++++, >75% $TNNT2^+$; GSK3B inhibitor. CHIR99021; Wnt inhibitor, Wnt-C59; Δ, media change. n=2 (hiPSC 59FSDNC3 and hESC H7 lines).

DETAILED DESCRIPTION OF THE EMBODIMENTS

Figure 1:
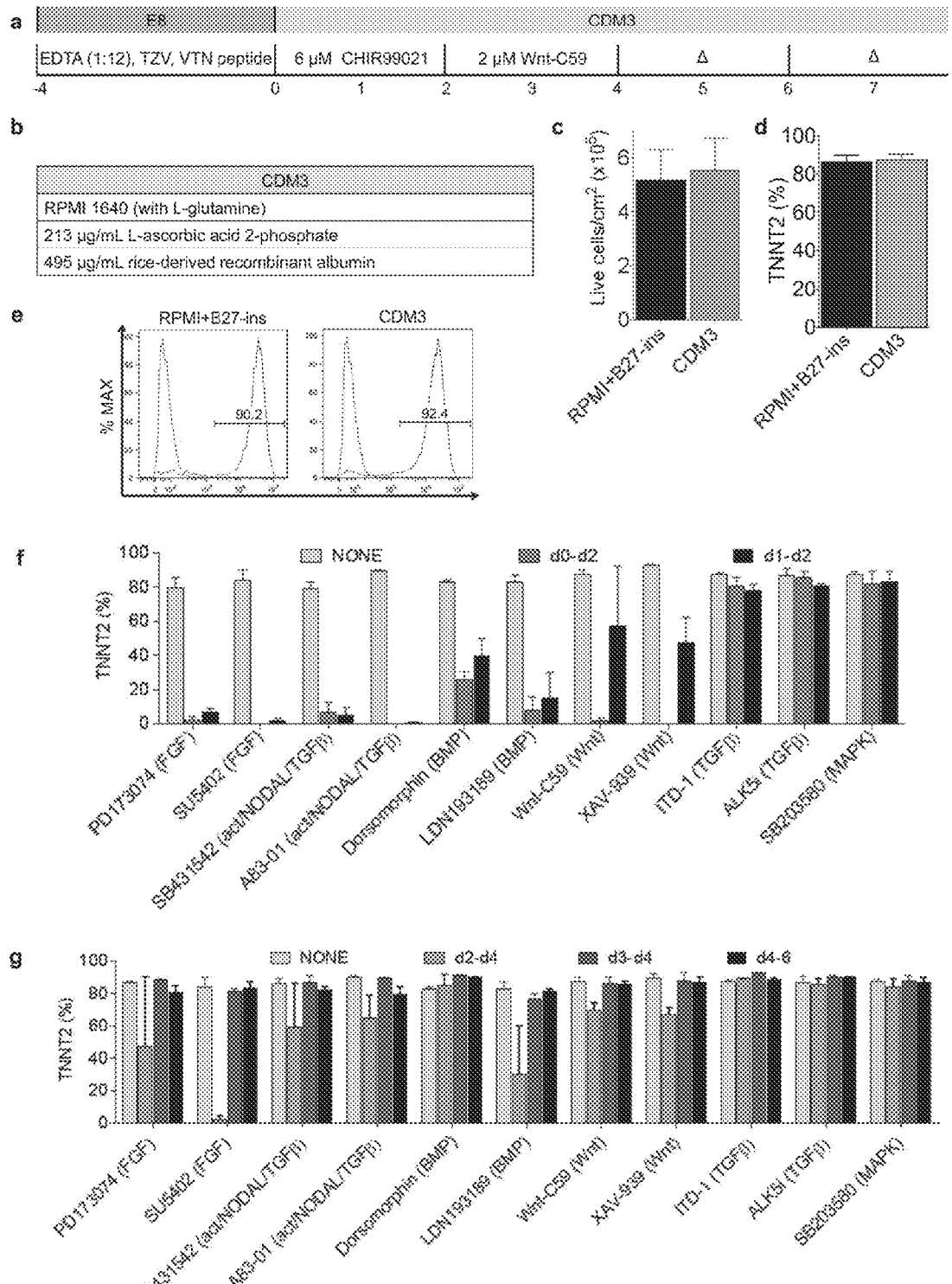
FIG. 1: Chemically defined differentiation protocol for efficient cardiac differentiation of hiPSCs. a) Schematic of optimized chemically defined cardiac differentiation protocol. E8, chemically defined pluripotency media; EDTA, ethylenediaminetetraacetic acid used for clump cell passaging TZV. thiazovivin; VTN, vitronectin; CDM3, chemically defined medium components; Δ, media change. b) Simple three-component formula of CDM3. c) Comparison of cardiac differentiation efficiency from differentiations in RPMI+B27-ins media and CDM3, measured by flow cytometry for cardiac troponin T (TNNT2) on day 15 cells (hiPSC line 59FSDNC3 shown), n=4. d) Comparison of total cell yield from differentiations in RPMI+B27-ins media and CDM3 at day 15, n=4. e) Typical TNNT2$^+$ populations in cells produced from differentiations in RPMI+B27-ins media and CDM3 measured by flow cytometry on day 15 cells. f) Effect of inhibition of signaling pathways during early differentiation. Small molecules that inhibit pathways associated with mesoderm induction were added at designated time points (day 0-2 or day 1-2), normal doses of CHIR99021, Wnt-C59, and media changes timings were maintained. Percentage of TNNT2+ was measured at d15 using flow cytometry, n=3. g) Effect of inhibition of signaling pathways post mesoderm induction. As f) but assessing cardiac induction time points (day 2-4, day 3-4, or day 4-6), n=3.

Methods are provided for producing a cardiomyocyte population from a mammalian pluripotent stem cell population. The methods of the invention comprise the steps of sequentially using a Wnt signaling agonist and antagonist, each in minimal media, to modulate Wnt signaling. Also provided are kits for practicing the methods described herein.

In some embodiments, a subject method is a method of producing a cardiomyocyte population from a mammalian pluripotent stem cell population, the method comprising: (a) contacting the mammalian pluripotent stem cell population with an effective amount of a Wnt signaling agonist in a minimal media for a period of about 12-60 hours, to produce an agonist-contacted cell population; and (b) contacting the agonist-contacted cell population with an effective amount of a Wnt signaling antagonist in a minimal media for a period of at least 12 hours. In some embodiments, the methods do not include contacting cells with small molecule agonists or antagonists (i.e., inhibitors) other than Wnt signaling agonists and antagonists. In some embodiments, the methods do not include contacting cells with the compounds SB431542 or LY364947 (inhibitors of TGFB), dorsomorphin or LDN 193189 (inhibitors of BMP), or SB203580 (an inhibitor of p38 MAPK). Minimal media of interest include, without limitation, CDM3, D3, D4, or D11 media, as described herein.

The pluripotent stem cell population is typically passaged in maintenance medium prior to cardiomyocyte induction. Maintenance media may comprise a ROCK inhibitor.

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context dearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed Methods Aspects of the invention include methods of producing a cardiomyocyte population from a mammalian pluripotent stem cell population. The term "population", e.g., cell population" or "population of cells", as used herein means a grouping (i.e., a population) of two or more cells that are separated (i.e., isolated) from other cells and/or cell groupings. For example, a 6-well culture dish can contain 6 cell populations, each population residing in an individual well. The cells of a cell population can be, but need not be, clonal derivatives of one another. A cell population can be derived from one individual cell. For example, if individual cells are each placed in a single well of a 6-well culture dish and each cell divides one time, then the dish will contain 6 cell populations. A cell population can be any desired size and contain any number of cells greater than one cell. For example, a cell population can be 2 or more, 10 or more, 100 or more, 1,000 or more, 5,000 or more, $10^4$ or more, $10^5$ or more, $10^6$ or more, $10^7$ or more, $10^8$ or more, $10^9$ or more, $10^{10}$ or more, $10^{11}$ or more, $10^{12}$ or more, $10^{13}$ or more, $10^{14}$ or more, $10^{15}$ or more, $10^{16}$ or more, $10^{17}$ or more, $10^{18}$ or more, $10^{19}$ or more, or $10^{20}$ or more cells.

Stem Cells and Cardiomyocytes

The term "stem cell" is used herein to refer to a mammalian cell that has the ability both to self-renew and to generate a differentiated cell type (see Morrison et al. (1997) Cell 88:287-298). In the context of cell ontogeny, the adjective "differentiated", or "differentiating" is a relative term. A "differentiated cell" is a cell that has progressed further down the developmental pathway than the cell it is being compared with. Thus, pluripotent stem cells (described below) can differentiate into lineage-restricted progenitor cells (e.g., mesodermal stem cells), which in turn can differentiate into cells that are further restricted (e.g., cardiomyocyte progenitors), which can differentiate into end-stage cells (i.e., terminally differentiated cells, e.g., cardiomyocytes), which play a characteristic role in a certain tissue type, and may or may not retain the capacity to proliferate further. Stem cells may be characterized by both the presence of specific markers (e.g., proteins, RNAs, etc.) and the absence of specific markers. Stem cells may also be identified by functional assays both in vitro and in vivo, particularly assays relating to the ability of stem cells to give rise to multiple differentiated progeny.

The stem cells of interest are mammalian, where the term refers to cells isolated from any animal classified as a mammal, including humans, domestic and farm animals, and zoo, laboratory, sports, or pet animals, such as dogs, horses, cats, cows, mice, rats, rabbits, etc. In some embodiments, the mammal is a human and the mammalian cells (i.e., a mammalian stem cell population) are therefore human cells (i.e., a human stem cell population).

A "progenitor cell" is a type of stem cell that typically does not have extensive self-renewal capacity (i.e., the number of self-renewing divisions is limited), and often can only generate a limited number of differentiated cell types (e.g., a specific subset of cells found in the tissue from which they derive). Thus, a progenitor cell is differentiated relative to its mother stem cell, but can also give rise to cells that are further differentiated (e.g., terminally differentiated cells). For the purposes of the present invention, progenitor cells are those cells that are committed to a lineage of interest (e.g., a cardiomyocyte progenitor), but have not yet differentiated into a mature cell (e.g., a cardiomyocyte).

When a stem cell divides symmetrically, both resulting daughter cells are equivalent. For example, a stem cell may undergo a self-renewing symmetric division in which both resulting daughter cells are stem cells with an equal amount of differentiation potential as the mother cell. However, a symmetric division is not necessarily a self-renewing division because both resulting daughter cells may instead be differentiated relative to the mother cell. When a stem cell divides asymmetrically, the resulting daughter cells are different than one another. For example, if a stem cell undergoes a self-renewing asymmetric division, then one of the resulting daughter cells is a stem cell with the same amount of differentiation potential as the mother cell while the other daughter cell is differentiated relative to the mother cell (e.g., a more lineage restricted progenitor cell, a terminally differentiated cell, etc.). A stem cell may directly differentiate, or may instead produce a differentiated cell type through an asymmetric or symmetric cell division.

Pluripotent Stem Cells

Stem cells (i.e., cell populations) of interest include pluripotent stem cells (PSCs. i.e., a PSC population). The term "pluripotent stem cell" or "PSC" is used herein to mean a stem cell capable of producing all cell types of the organism. Therefore, a PSC can give rise to cells of all germ layers of the organism (e.g., the endoderm, mesoderm, and ectoderm of a mammal). Pluripotent cells are capable of forming teratomas and of contributing to ectoderm, mesoderm. or endoderm tissues in a living organism.

PSCs can be derived in a number of different ways. For example, embryonic stem cells (ESCs) are derived from the inner cell mass of an embryo (Thomson et al, Science. 1998 November 6; 282(5391):1145-7) whereas induced pluripotent stem cells (iPSCs) are derived from somatic cells (Takahashi et. al, Cell. 2007 November 30; 131(5):861-72; Takahashi et. al, Nat Protoc. 2007; 2(12):3081-9; Yu et. al, Science. 2007 December 21:318(5858):1917-20. Epub 2007 November 20). Because the term PSC refers to pluripotent stem cells regardless of their derivation, the term PSC encompasses the terms ESC and iPSC, as well as the term embryonic germ stem cells (EGSC), which are another example of a PSC. A human PSC can be referred to as an "hPSC", an "hESC", an "hEGSC", and/or an "hiPSC", depending on the context and the derivation of the PSC. PSCs may be in the form of an established cell line, they may be obtained directly from primary embryonic tissue, or they may be derived from a somatic cell. The methods described herein can be used to produce cardiomyocytes from any mammalian PSC population, including but not limited to an ESC population, an iPSC population, and/or an EGSC population.

By "embryonic stem cell" (ESC) is meant a PSC that was isolated from an embryo, typically from the inner cell mass of the blastocyst. ESC lines are listed in the NIH Human Embryonic Stem Cell Registry, e.g. hESBGN-01, hESBGN-02, hESBGN-03, hESBGN-04 (BresaGen, Inc.); HES-1, HES-2, HES-3, HES-4, HES-5, HES-6 (ES Cell International); MizhES1 (MizMedi Hospital-Seoul National University); HSF-1, HSF-6 (University of California at San Francisco); and H1, H7, H9, H13, H14 (Wisconsin Alumni Research Foundation (WiCell Research Institute)). Stem cells of interest also include embryonic stem cells from other primates, such as Rhesus stem cells and marmoset stem cells. The stem cells may be obtained from any mammalian species, e.g. human, equine, bovine, porcine, canine, feline, rodent, e.g. mice, rats, hamster, primate, etc. (Thomson et al. (1998) Science 282: 1145; Thomson et al. (1995) Proc. Natl. Acad. Sci USA 92:7844; Thomson et al. (1996) Biol. Reprod. 55:254;Shamblott et al., Proc. Natl. Acad. Sci. USA 95:13726, 1998). In culture, ESCs typically grow as flat colonies with large nucleo-cytoplasmic ratios, defined borders and prominent nucleoli. In addition, ESCs express SSEA-3, SSEA-4, TRA-1-60, TRA-1-81, and Alkaline Phosphatase, but not SSEA-1. Examples of methods of generating and characterizing ESCs may be found in, for example, U.S. Pat. Nos. 7,029,913, 5,843,780, and 6,200,806, the disclosures of which are incorporated herein by reference. Methods for proliferating hESCs in the undifferentiated form are described in WO 99/20741, WO 01/51616, and WO 03/020920.

By "embryonic germ stem cell" (EGSC) or "embryonic germ cell" or "EG cell" is meant a PSC that is derived from germ cells and/or germ cell progenitors, e.g. primordial germ cells, i.e. those that would become sperm and eggs. Embryonic germ cells (EG cells) are thought to have properties similar to embryonic stem cells as described above. Examples of methods of generating and characterizing EG cells may be found in, for example, U.S. Pat. No. 7,153,684; Matsui, Y., et al. (1992) Cell 70:841; Shamblott, M., et al. (2001) Proc. Natl. Acad. Sci. USA 98: 113; Shamblott, M., et al. (1998) Proc. Natl. Acad. Sci. USA, 95:13726; and Koshimizu, U., et al. (1996) Development, 122:1235. the disclosures of which are incorporated herein by reference.

By "induced pluripotent stem cell" or "iPSC" it is meant a PSC that is derived from a cell that is not a PSC (i.e., from a cell this is differentiated relative to a PSC). iPSCs can be derived from multiple different cell types, including terminally differentiated cells. iPSCs have an ES cell-like morphology, growing as flat colonies with large nucleo-cytoplasmic ratios, defined borders and prominent nuclei. In addition, iPSCs express one or more key pluripotency markers known by one of ordinary skill in the art, including but not limited to Alkaline Phosphatase, SSEA3, SSEA4, Sox2, Oct3/4, Nanog, TRA160, TRA181, TDGF 1, Dnmt3b, FoxD3, GDF3, Cyp26a1, TERT, and zfp42. Examples of methods of generating and characterizing iPSCs may be found in, for example, U.S. Patent Publication Nos. US20090047263, US20090068742, US20090191159, US20090227032, US20090246875, and US20090304646, the disclosures of which are incorporated herein by reference. Generally, to generate iPSCs, somatic cells are provided with reprogramming factors (e.g. Oct4, SOX2. KLF4, MYC, Nanog, Lin28, etc.) known in the art to reprogram the somatic cells to become pluripotent stem cells.

By "somatic cell" it is meant a cell of an organism that is not a germ cell. Thus, in the absence of experimental manipulation, a mammalian somatic cell does not ordinarily give rise to all types of cells in the body, although adult somatic stem cells do exist (e.g., lineage restricted progenitor cells) While some organisms have been shown to contain adult somatic pluripotent stem cells, such a cell has not yet been shown to exist in mammals, including humans.

By "mitotic cell" it is meant a cell undergoing mitosis. Mitosis is the process by which a eukaryotic cell separates the chromosomes in its nucleus into two identical sets in two separate nuclei. It is generally followed immediately by cytokinesis, which divides the nuclei, cytoplasm, organelles and cell membrane into two cells containing roughly equal shares of these cellular components.

By "post-mitotic cell" it is meant a cell that has exited from mitosis, i.e., it is "quiescent", i.e. it is no longer undergoing divisions. This post-mitotic state may be temporary (i.e. reversible) or it may be permanent. Many terminally differentiated cells are considered to be post-mitotic, although some terminally differentiated cells can become mitotic under particular circumstances (e.g., injury).

Cardiomyocytes

As used herein, a "cardiomyocyte" or "myocardial cell" is a terminally differentiated heart muscle cell. Embryonic cardiomyogenesis (i.e., the formation of the heart muscle) begins with the generation of mesoderm via the process of gastrulation, which has been studied in the mouse (Arnold et al., (2009) Nat. Rev. Mol. Cell Biol. 10, 91-103; Buckingham et al., 2005, Nat. Rev. Genet. 6, 826-835; Tam et al., 2007, Nat. Rev. Genet. 8, 368-381). At mouse embryonic day 5.75 (E5.75), mesodermal markers such as T (brachyury) and Eomes are induced, which then induce the expression of MESP1, which is described in the art as the "master regulator" of cardiac progenitor specification (Burridge et al., Cell Stem Cell. 2012 January 6; 10 (1):16-28). Downstream of MESP1, cardiogenesis relies on a complex web of interacting factors and genes, including Tbx5, Nkx2-5, Mef2c, Gata4, Hand2, Myocd, Isl1, and Foxh1 (Bondue et. al, (2010) Circ. Res. 107, 1414-1427). Once cardiogenic mesoderm is specified, canonical WNT and NOTCH signaling regulate CPC (Cardiac Progenitor Cell) maintenance and differentiation, respectively (Qyang et al., 2007 Cell Stem Cell 1, 165-179; Kwon et al., 2009 Nat. Cell Biol. 11, 951-957).

The cardiac mesoderm gives rise to the endocardium. the first heart field (FHF, which forms the atria, left ventricle, and the nodal conduction system), the secondary heart field (SHF, which forms the right ventricle, outflow tract, and part of the atria), and the proepicardial mesenchyme (Buckingham et al., 2005 Nat. Rev. Genet. 6, 826-835.). The FHF differentiates at the cardiac crescent stage, whereas the SHF (marked by the expression of Isl1) remains in an undifferentiated progenitor state, due to inhibitory WNT signals from the midline, until incorporation into the heart (Kwon et al., 2007 Proc. Natl. Acad. Sci. USA 104, 10894-10899). Once the cardiac crescent is formed, it is exposed to BMP signaling from the underlying anterior ectoderm as well as to BMP, FGF, anti-canonical WNT, and noncanonical WNT signaling from the overlying anterior endoderm (Solloway and Harvey, 2003 Cardiovasc. Res. 58, 264-277). By E8.0, these cells form a primitive heart tube, consisting of an interior layer of endocardial cells and an exterior layer of myocardial cells. Once within the heart, FHF and SHF cells appear to proliferate in response to endocardial-derived signals, such as neuregulin1 (NRG1), which is driven by NOTCH signaling (Grego-Bessa at al., 2007 Dev. Cell 12, 415-429), and epicardial signals, such as retinoic acid, that function via FGF signaling (Lavine et al., 2005 Dev. Cell 8, 85-95).

With regard to producing cardiomyocytes from pluripotent stem cells, there is consensus that the cardiac differentiation process is very delicate, and the variability in each individual component of the cardiac differentiation strategy must be carefully optimized to reliably produce cardiomyocytes.

The cardiomyocytes produced to date from hPSCs are largely immature and most analogous to fetal stages of development; these hPSC-derived cardiomyocytes exhibit automaticity (spontaneous contraction), fetal-type ion channel expression (Beqqali et al., 2006 Stem Cells 24, 1956-1967), fetal-type electrophysiological signals (Davis et al., 2011 Trends Mol. Med. 17, 475-484.), fetal-type gene expression patterns, and fetal-type physical phenotypes (Cao et al., 2008 PLoS ONE 3, e3474). Conflicting data exist regarding the maturity of Ca2+ handling and sarcoplasmic reticulum status for hPSC-derived cardiomyocytes, although there is evidence that hPSC-derived cardiomyocytes demonstrate some mature properties (Itzhaki at al., 2011b PLoS ONE 6, e18037). The lack of maturity of hPSC-derived cardiomyocytes may reduce the suitability of drug testing but may also have benefits in regards to regenerative medicine. For example, rodent fetal cardiomyocytes have been demonstrated to have enhanced cell survival over adult cardiomyocytes after engraftment into the rat heart (Reinecke et al., 1999 Circulation 100, 193-202), although the issue of automaticity still remains. Three major subtypes of hPSC-derived cardiomyocytes can be derived that have atrial-, ventricular-, or nodal-like phenotypes as determined by electrophysiological analysis of action potentials (APs). Common hPSC differentiation methodologies create a mixture of these cell types. An enriched population of nodal-like cells could potentially be used in the formation of a biological pacemaker, whereas ventricular types may be used for recovery from myocardial infarction. Zhu and colleagues demonstrated that GATA6-GFP can mark nodal-like cells (Zhu et al., 2010 Circ. Res. 107, 776-786) and that inhibition of NRG1b/ERBB signaling can enhance the population of nodal-like cardiomyocytes. Zhang and colleagues have similarly demonstrated that retinoic acid can increase the proportion of atrial-like cardiomyocytes and that retinoic acid inhibition can increase the proportion of ventricular-like cells (Zhang et al., 2011 Cell Res. 21, 579-587).

Phenotypes of cardiomyocytes that arise during development of the mammalian heart can be distinguished: primary cardiomyocytes; nodal cardiomyocytes; conducting cardiomyocytes and working cardiomyocytes. All cardiomyocytes have sarcomeres and a sarcoplasmic reticulum (SR), are coupled by gap junctions, and display automaticity. Cells of the primary heart tube are characterized by high automaticity, low conduction velocity, low contractility, and low SR activity. This phenotype largely persists in nodal cells. In contrast, atrial and ventricular working myocardial cells display virtually no automaticity, are well coupled intercellularly, have well developed sarcomeres, and have a high SR activity. Conducting cells from the atrioventricular bundle, bundle branches and peripheral ventricular conduction system have poorly developed sarcomeres, low SR activity, but are well coupled and display high automaticity.

A "cardiomyocyte progenitor" is defined as a cell that is capable (without dedifferentiation or reprogramming) of giving rise to progeny that include cardiomyocytes.

Such progenitors may express various cytoplasmic and nuclear markers typical of the lineage, including, without limitation, cardiac troponin I (cTnI), cardiac troponin T (cTnT), sarcomeric myosin heavy chain (MHC), GATA-4, Nkx2.5, N-cadherin, β1-adrenoceptor (β1-AR), ANF, the MEF-2 family of transcription factors, creatine kinase MB (CK-MB), myoglobin, or atrial natriuretic factor (ANF).

Verifying Cardiomyocyte Production

In some embodiments, the methods include the step of verifying the presence of cardiomyocytes n the antagonist-contacted cell population. Verifying relies on phenotypes (e.g., gene or protein expression, electrophysiological profile, responsiveness to cardioactive drugs, etc.) known in the art to be characteristic of cardiomyocytes. In some such embodiments, verifying includes determining a cardiomyocyte electrophysiological profile. (i.e., electrophysiological profiling) (see Davis et. al, Trends Mol Med. 2011 September; 17(9): 475-84. Epub 2011 June 22.; Kim et. al, Stem Cells Dev. 2010 June; 19(6):783-95.; and Ma et. at, Am J Physiol Heart Circ Physiol. 2011 November; 301(5):H2006-17. Epub 2011 September 2.) In some embodiments, the stage of differentiation (i.e., the degree of cardiomyocyte maturity) can also be gleaned from electrophysiological profiles. For example, Kim et. al, (Kim et. al, Stem Cells Dev. 2010 June; 19(6):783-95) compared the action potential amplitude (APA), maximum diastolic potential (MDP), maximal upstroke velocity ($dV/dt_{max}$), and cAPD90 (cAPD90 is the measured action potential (AP) duration at the 90% of repolarization (APD90) corrected as such: cAPD90=APD90/square root of RR) between immature and mature PSC derived cardiomyocytes. The mature subgroup of cardiomyocytes possessed more hyperpolarized MDP, higher APA, and faster maximal upstroke velocity than the immature group. Thus, in some embodiments, the step of verifying the presence of cardiomyocytes includes a determination of the level of maturation of the cardiomyocytes. In some embodiments, the step of verifying the presence of cardiomyocytes includes a determination of the level of maturation of the cardiomyocytes via electrophysiological profiling.

In some embodiments, verifying includes determining responsiveness (e.g., beating frequency, contractility, and the like) to known cardioactive drugs. Studies have demonstrated that PSC derived cardiomyocytes will react to cardioactive drugs with the expected response (Davis et. al, Trends Mol Med. 2011 September; 17(9):475-84. Epub 2011 June 22; Yokoo et. al, Biochem Biophys Res Commun. 2009 September 25; 387(3):482-8. Epub 2009 July 16; The effects of cardioactive drugs on cardiomyocytes derived from human induced pluripotent stem cells.) Thus, some embodiments include the verification of the presence of cardiomyocytes by the demonstration of cardiomyocyte-like responses to cardioactive drugs. Cardioactive drugs are known in the art, as are methods to detect responsiveness to such drugs (Davis et. al, Trends Mol Med. 2011 September; 17(9):475-84. Epub 2011 June 22; Yokoo et. al, Biochem Biophys Res Commun. 2009 September 25; 387(3):482-8. Epub 2009 July 16; Reppel et. al, Cell Physiol Biochem. 2007; 19(5-6); 213-24). Suitable cardioactive drugs include but are not limited to; (i) Sodium ($Na^+$) channel blockers including (but not limited to) quinidine, procainamide, disopryamide, tocainide, mexiletine, propafenone, moricizine, flecainide, tetrodotoxin, phenytoin, encainide, and lidocaine; (ii) Potassium ($K^+$) channel blockers including (but not limited to): 4-aminopyridine (4-AP), dofetilide, $BaCl_2$, sotalol, ibutilide, amiodarone, sparfloxacin, procainamide, 293-B, DPO-1, glibenclamide, E-4031, azimilide, bretyllum, clofilium, nifekalant, tedisamil, sematilide, and ampyra; (iii) Calcium ($Ca^{2+}$) channel blockers including (but not limited to): verapamil, nifedipine, diltiazem, mibefradil, bepridil, fluspirilene, fendiline, amlodipine, aranidipine, azelnidipine, bamidipine, benidipine, cilnidipine, cinalong, clevidipine, isradipine, efonidipine, felodipine, lacidipine, lercanidipine, manidipine, nicardipine, nilvadipine, nimodipine, nisoldipine, nitrendipine, pranidipine, and w-conotoxin: and (iv) Multi-channel blockers including (but not limited to): procainamide, and terfenadine.

In some embodiments, verifying includes contacting the antagonist-contacted cell population with an antibody specific for a cardiomyocyte marker protein, and determining the percentage of cells positive for expression, wherein cells positive for expression are cardiomyocytes. Any protein marker that is in specific to a cardiomyocyte relative to the surrounding isolated cell population can be used to verify the production of cardiomyocytes. For example, suitable protein markers specific to cardiomyocytes that can be used include, but are not limited to cardiac troponin T type 2 (cTNT, TNNT2), myosin light chain 2 a (MLC2a) (atrial and immature ventricular cardiomyocytes), myosin light chain 2 v (MLC2v) (mature ventricular cardiomyocytes), EMILIN2 (Van Hoof et al., 2010 J. Proteome Res. 9, 1610-1618), SIRPA (Dubois et al., 2011 Nat. Biotechnol. 29, 1011-1018; Elliott et al., 2011 Nat. Methods 8, 1037-1040), and VCAM (Elliott et al., 2011; Uosaki et al, 2011). In some embodiments, markers such as Gata6, Tbx5. Nkx2-5, Mef2c, Gata4, Hand2, Myocd, Isl1, Foxh1, and MYH6 are used to verify the production of cardiomyocytes.

In some cases, at least 80% (e.g., at least 85%, at least 90%, at least 95%, or at least 98%) of the cells of the antagonist-contacted cell population are determined to be cardiomyocytes.

Cardiomyocyte Purification:

To increase the fraction of obtained cells that are cardiomyocytes, it is sometimes advantageous to enrich for (i.e., purify) the produced cardiomyocytes. Traditional methods for the purification of cardiomyocytes that involve density gradient centrifugation (Xu et al., 2002 Circ. Res. 91, 501-508.) are unsuitable for large-scale practice and routinely result in only a 5- to 10-fold enrichment in cardiomyocyte populations (Murry and Keller, 2008 Cell 132, 661-680). Genetic selection of cells based on the expression of a selectable marker driven by a lineage-restricted promoter such as NKX2-5 (Elliott et al., 2011 Nat. Methods 8, 1037-1040), MYH6 (Anderson et al., 2007 Mol. Ther. 15, 2027-2036), MLC2V (Huber et al., 2007 FASEB J. 21, 2551-2563), and ISL1 (Bu et al., 2009 Nature 460, 113-117) offers the possibility of isolating myocardial precursors at high purity; when this process is coupled with antibiotic selection, it is possible to generate cells at greater than 99% purity. Indeed, it has been demonstrated that an MYH6-blastocidin hiPSC line can be differentiated using simple suspension culture and 10% FBS in DMEM to produce hiPSC-derived cardiomyocytes in commercial quantities (Ma et al., 2011 Am. J. Physiol. Heart Circ. Physiol. 301, H2006-H2017). The principal drawback of genetic selection is the necessity (at present) of inserting a selection cassette into the host genome, which may increase the risk of tumorigenesis and is therefore unsuitable for clinical practice.

Antibodies to cell surface markers have the advantage of not requiring genetic modification of stem cell populations, and therefore may be applicable to all hPSC lines. FACS has the ability to analyze multiple surface markers simultaneously, and it has been used to isolate cardiac progenitor populations based on the expression of the receptor tyrosine kinases KDR (FLK1/VEGFR2) and PDGFRA (Kattman et al., 2011 Cell Stem Cell 8, 228-240). Because this population also contains endothelial and smooth muscle populations, the differentiated progeny represents a mixture of cardiomyocyte and vascular lineages. The recent identification of markers expressed specifically on cardiomyocytes, including EMILIN2 (Van Hoof et al., 2010 J. Proteome Res. 9, 1610-1618), SIRPA (Dubois et al., 2011 Nat. Biotechnol. 29, 1011-1018; Elliott et al., 2011 Nat. Methods 8, 1037-1040), and VCAM (Elliott et al., 2011 Nat. Methods 8, 1037-1040; Uosaki et al., 2011 PLoS ONE 6, e23657), has made it possible to isolate highly enriched populations of these cells from hESCs or hiPSCs by FACS or magnetic bead sorting.

Another nongenetic method for isolating hPSC-derived cardiomyocytes is based on the use of the mitochondrial dye tetramethylrhodamine methyl ester perchlorate (TMRM) (Hattori et al., 2010 Nat. Methods 7, 61-66). Because this dye only functions in cardiomyocytes with high mitochondrial density, it does not detect the most immature cells that develop in the cultures (Dubois et al., 2011 Nat. Biotechnol. 29, 1011-1018).

In some embodiments, the cardiomyocytes are purified (i.e., enriched) from surrounding cells by the technique of glucose deprivation. In some such embodiments, once beating cells are observed (usually about 9-13 days after the PSCs are contacted with a Wnt signaling agonist), the culture media is replaced with minimal media lacking glucose, which media is optionally supplemented with lactate, e.g. at a concentration of from about 1 mM, about 2.5 mM, about 5 mM, and not more than about 25 mM, not more than about 15 mM, not more than about 10 mM. In the absence of glucose, non-cardiomyoctes are lost due to lack of glycogen stores. Culture in minimal media lacking glucose (i.e., glucose deprivation) can persist for a total of about 3-5 days (e.g., about 3-4 days, about 4-5 days. about 3 days, about 4 days, or about 5 days). The media is then replaced with media containing glucose. Therefore, in some embodiments, an antagonist-contacted cell population is contacted with a minimal media lacking glucose for a period of time sufficient to enrich the cell population for cardiomyocytes. A cell population enriched for cardiomyocytes is one in which at least about 70% (e.g., at least about 75%, at least about 80%, at least about 85%, at least about 90%, at least about 95%, at least about 97%, at least about 98%, at least about 99%, or 100%) of the cells of the cell population are cardiomyocytes.

Cardiomyocyte Cryopreservation

In some embodiments, the cardiomyoctes (i.e., a cardiomyocyte population) produced from a mammalian PSC is preserved for future use. Methods of cryopreservation are known in the art (Xu et al, Regen Med. 2011 January; 6(1): 53-66; Norström et. al, Exp Biol Med (Maywood). 2006 December; 231(11):1753-62). Specifically, cardiomyocytes can be cryopreserved with ~70-90% viability by performing the following steps: (i) replace culture media with 1 mL per 10 $cm^2$ room temperature TrypLE (ii) incubate at 37° C. for 5-10 min. (iii) Detach cells from growth cell surface with minimal media (described below) and manually triturate to form a single cell suspension. (iv) count cells, (v) centrifuge at 200 g for 4 min, (vi) resuspend cell pellet in minimal media with 10% DMSO, and (vii) freeze cells and store in liquid nitrogen using standard tissue culture techniques commonly used in the art to preserve cells. Cells can be frozen at 1-50 million cells per vial. Cardiomyocytes should be frozen on any day between day 11-15 (counting day 0 as the day PSCs are contacted with a Wnt signaling agonist). While cardiomyocytes can be frozen after day 15, cells tend to become more and more difficult to dissociate as time proceeds. When ready for use, cardiomyoctes should be thawed in a manner as commonly known in the art for thawing frozen cultured cells.

Wnt Signaling Agonists and Antagonists

Wnt Signaling Pathway

The misregulation of Wnt signaling components at various stages during embryogenesis leads to catastrophic developmental defects while misregulation in adults leads to various disease states, including cancer. There are two main branches of the Wnt signaling pathway: (1) the canonical β-Catenin dependent Wnt signaling pathway and (2) the non-canonical β-Catenin independent pathways, which include planar cell polarity (PCP) signaling as well as Calcium signaling (Gao, et. al. Cell Signal. 2010 May; 22(5):717-27. Epub 2009 December 13). As used herein, the terms "Wnt signaling" and "Wnt/β-Catenin signaling" are used interchangeably to refer to the canonical β-Catenin dependent Wnt signaling pathway. As such, a "Wnt signaling agonist" (described in greater detail below) increases output from the β-Catenin dependent Wnt signaling pathway while a "Wnt signaling antagonist" (described in greater detail below) decreases output from the β-Catenin dependent Wnt signaling pathway. Aspects of the invention include modulation of the Wnt signaling pathway by contacting a mammalian PSC population with a Wnt signaling agonist to produce an agonist-contacted cell population, and further contacting the agonist-contacted cell population with a Wnt signaling antagonist.

Activation of the Wnt pathway culminates when the protein β-Catenin enters the cell nucleus (for recent review of the canonical β-Catenin dependent Wnt signaling pathway see Clevers et. al., Cell. 2012 June 8; 149(6):1192-205: Wnt/β-catenin signaling and disease). However, in the absence of Wnt signaling, free cytosolic β-Catenin is incorporated into a complex, known in the art as the β-Catenin destruction complex, which includes the proteins Axin, Adenomatous Polyposis Coli (APC), and glycogen synthase kinase (GSK-3β). Phosphorylation of β-Catenin by GSK-3β designates β-Catenin for the ubiquitin pathway and degradation by proteasomes (via βTRCP).

Transduction of the β-Catenin dependent Wnt signaling pathway (i.e., the Wnt signaling pathway) is triggered by the binding of secreted Wnt ligands to two distinct families of cell-surface receptors: the Frizzled (Fz) receptor family and the LDL-receptor-related protein (LRP) family (Akiyama, Cytokine Growth Factor Rev. 11:273-82 (2000)). This binding leads to the activation of Dishevelled (Dvl) proteins, which inhibit glycogen synthase kinase-3β (GSK-3β) activity (i.e., phosphorylation of O-Catenin), leading to the cytosolic stabilization of β-Catenin. Stabilized β-Catenin then enters the nucleus and associates with the TCF/LEF (T Cell-specific transcription Factor/Lymphoid Enhancer Factor) family of transcription factors to induce transcription of important downstream target genes. Secreted antagonists (i.e., negative regulatory components) of the Wnt signaling pathway include members of the WIF (Wnt inhibitory factor), sFRP (Secreted Frizzled Related Protein), Dkk (Dickkopf), Notum, and WISE/SOST families, which interfere with the appropriate interactions among Wnt, Frizzled, and LRP proteins (Melkonyan et al., 1997, Proc Natl Acad Sci USA 94(25):13636-41; Moon et al., 1997, Cell 88(6):725-8; Fedi et al., 1999, *J Biol Chem* 274(27):19465-72; Nusse, 2001, Nature 411(6835):255-6; Clevers et. al., Cell. 2012 June 8; 149(6):1192-205: Wnt/β-catenin signaling and disease).

Thus, in the absence of Wnt signaling, cytosolic (and therefore nuclear) levels of β-Catenin are kept low by negative regulatory components of the pathway while in the presence of Wnt signaling, cytosolic (and therefore nuclear) levels of β-Catenin are stabilized by positive regulatory components of the pathway.

By "negative regulatory components" of the Wnt pathway, it is meant proteins that function by antagonizing the Wnt pathway, thus resulting in decreased pathway output (i.e., decreased target gene expression). Examples of known negative regulatory components of the Wnt pathway include, but are in no way limited to: WIF, sFRP, Dkk, APCDD1, Notum, SOST, Axin, APC, GSK-33, CK1γ, WTX, and βTrCP.

By "positive regulatory components" of the Wnt pathway, it is meant proteins that function by enhancing the Wnt pathway, thus resulting in increased pathway output (i.e., increased target gene expression). Examples of known positive regulatory components of the Wnt pathway include, but are in no way limited to: Wnt, Norrin, R-spondin, PORCN, Wls, Frizzled, LRP5 and LRP6, Tspan12, Lgr4, Lgr$_6$, Lgr6, Dvl, β-Catenin, and TCF/LEF.

In some embodiments, a subject Wnt signaling agonist and/or antagonist is "specific for" or "specifically binds to" a regulatory component of the Wnt signaling pathway such that binding results in modification of pathway output (i.e., transcription of target genes). The binding of an agonist or antagonist can be mediated by covalent or non-covalent interactions or a combination of covalent and non-covalent interactions. When the interaction of the agonist or antagonist with the component to which it specifically binds produces a non-covalently bound complex, the binding which occurs is typically electrostatic, hydrogen-bonding, or the result of lipophilic interactions. In particular, specific binding is characterized by the preferential binding of one member of a pair to a particular species relative to other species within the family of compounds to which the corresponding member of the binding member belongs. Thus, for example, a Wnt signaling agonist that is specific for the negative regulatory component GSK-3 preferably binds to GSK-3 relative to other proteins in the cell.

Wnt Signaling Agonist

A subject Wnt signaling agonist is any molecule (e.g., a chemical compound; a non-coding nucleic acid, e.g., a non-coding RNA; a polypeptide; a nucleic acid encoding a polypeptide, etc.) that results in increased output (i.e., increased target gene expression) from the Wnt signaling pathway. For example, a Wnt signaling agonist can function by stabilizing, enhancing the expression of, or enhancing the function of a positive regulatory component of the pathway or by destabilizing, decreasing the expression of, or inhibiting the function of a negative regulatory component of the pathway. Thus, a Wnt signaling agonist can be a nucleic acid encoding one or more positive regulatory components of the pathway. A Wnt signaling agonist can also be a small molecule or nucleic acid that stabilizes a positive regulatory component of the pathway either at the level of mRNA or protein.

In some embodiments, a Wnt signaling agonist functions by stabilizing β-Catenin, thus allowing nuclear levels of β-Catenin to rise. β-Catenin can be stabilized in multiple different ways. As multiple different negative regulatory components of the Wnt signaling pathway function by facilitating the degradation of β-Catenin, a subject Wnt signaling agonist can be a small molecule or nucleic acid inhibitor (e.g., microRNA, shRNA, etc.)(functioning at the level of mRNA or protein) of a negative regulatory component of the pathway. For example, in some embodiments, the Wnt signaling agonist is an inhibitor of GSK-3β. In some such embodiments, the inhibitor of GSK-3β is a small molecule chemical compound (e.g., TWS119, BIO, CHIR-99021,SB 216763, SB 415286, CHIR-98014 and the like).

TWS119: 3-(6-(3-aminophenyl)-7H-pyrrolo[2,3-d]pyrimidin-4-yloxy)phenol is described by Ding et. al, Proc Natl Acad Sci USA. 2003 June 24; 100(13):7632-7. BIO: 6-bromo-3-[(3E)-1,3-dihydro-3-(hydroxyimino)-2H-indol-2-ylidene]-1,3-dihydro-(3Z)-2H-indol-2-one or (2'Z,3'E)-6-Bromoindirubin-3'-oxime is described by Meijer et. al, Chem Biol. 2003 December; 10(12):1255.66. CHIR-99021: 6-[[2-[[4-(2,4-dichlorophenyl)-5-(5-methyl-1H-imidazol-2-yl)-2-pyrimidinyl]amino]ethyl]amino]-3-pyridinecarbonitrile is described by Bennett et al., J Biol Chem. 2002 August 23:277 (34):30998-1004. SB 216763: 3-(2,4-dichlorophenyl)-4-(1-methyl-1H-indol-3-yl)-1H-pyrrole-2,5-dione is described by Cross et al., J Neurochem. 2001 April; 77(1):94-102. SB 415286: 3-(3-chloro-4-hydroxyphenylamino)-4-(2-nitrophenyl)-1H-pyrrole-2,5-dione is described by Cross et al., J Neurochem. 2001 April; 77(1):94-102. CHIR-98014: N2-(2-(4-(2,4-dichlorophenyl)-5-(1H-imidazol-1-yl)pyrimidin-2-ylamino)ethyl)-5 nitropyridine-2,6-diamine is described by Ring et al., Diabetes. 2003 March; 52(3):588-95. Each reference is herein specifically incorporated by reference.

Aspects of the invention include contacting a mammalian PSC population with a Wnt signaling agonist for a period of about 12-60 hours (e.g., about 12-80 hours, about 12-48 hours, about 12-24 hours, about 24-60 hours, about 24-48 hours, about 24-36 hours, about 12 hours, about 18 hours, about 20 hours, about 22 hours, about 24 hours, about 26 hours, about 28 hours, about 30 hours, about 36 hours, about 42 hours, about 48 hours, about 54 hours, or about 60 hours).

The effective dose of a wnt agonist may be at least about 0.1 µM. at least about 1 µM, at least about 2.5 µM, at least about 5 µM, and usually not more than about 500 µM, not more than about 250 µM, not more than about 100 µM, not more than about 50 µM. In some embodiments the effective amount is around about 6 µM.

Wnt Signaling Antagonist

A subject Wnt signaling antagonist is any molecule (e.g., a chemical compound; a nucleic acid, e.g., a non-coding RNA; a polypeptide; a nucleic acid encoding a polypeptide, etc.) that antagonizes the Wnt signaling pathway, thus resulting in decreased pathway output (i.e., decreased target gene expression). For example, a Wnt signaling antagonist can function by destabilizing, decreasing the expression of, or inhibiting the function of a positive regulatory component of the pathway or by stabilizing, enhancing the expression of, or enhancing the function of a negative regulatory component of the pathway.

Thus, a Wnt signaling antagonist can be a nucleic acid encoding one or more negative regulatory components of the pathway. A Wnt signaling antagonist can also be a small molecule or nucleic acid that stabilizes a negative regulatory component of the pathway either at the level of mRNA or protein. Likewise, a subject Wnt signaling antagonist can be a small molecule or nucleic acid inhibitor (e.g., microRNA, shRNA, etc.) (functioning at the level of mRNA or protein) of a positive regulatory component of the pathway. In some embodiments, the Wnt signaling antagonist is a small molecule chemical compound (e.g., C59, ICG-001, IWR-1, IWP-2, IWP-4, XAV-939, pyrvinium, PKF115-584, and the like).

C59: 2-(4-(2-Methylpyridin-4-yl)phenyl)-N-4-(pyridin-3-yl)phenyl)acetamide) is described in WO2010101849. ICG-001: (6S,9aS)-6-(4-hydroxybenzyl)-N-benzyl-8-(naphthalen-1-ylmethyl)-4,7-diaxo-hexahydro-2H-pyrazino[1,2-a]pyrimidine-1(6H)-carboxamide is described in Emami et. al, Proc Natl Acad Sci USA. 2004 August 24; 101(34):12682-7. IWR-1: 4-(1,3,3a,4,7,7a-Hexahydro-1,3-dioxo-4,7-methano-2H-isoindol-2-yl)-N-8-quinolinyl-Benzamide is described by Chen, B., et al., Nat Chem Biol. 2009 February; 5(2):100-7. IWP-2: N-(6-Methyl-2-benzothiazoyl)-2-[(3,4,6,7-tetrahydro-4-oxo-3-phenylthieno[3,2-d]pyrimidin-2-yl)thio]-acetamide is described by Chen, B., et al., Nat Chem Biol. 2009 February; 5(2):100-7. IWP-4: 2-(3,4,6,7-tetrahydro-3-(2-methoxyphenyl)-4-oxothieno[3,2-d]pyrimidin-2-ylthio)-N-(6-methylbenzo[d]thiazol-2-yl)acetamide is described by Chen, B., et al., Nat Chem Biol. 2009 February; 5(2):100-7. XAV939 (XAV-939): 3,5,7,8-Tetrahydro-2-[4-(trifluoromethyl)phenyl]-4H-thiopyrano[4,3-d]pyrimidin-4-one is described by Huang et al., Nature. 2009 October 1; 461(7264):614-20. Pyrvinium: 6-Dimethylamino-2'-(2-(2,5-dimethyl-1-phenyl-3-pyrrolyl)vinyl)-1-methylquinolinium 2-[(E)-2-(2,S-dimethyl-1-phenylpyrrol-3-yl)ethenyl]-1-methylquinolin-1-ium-6-amine is described by Saraswati et. al, PLoS One. 2010 Nov. 29; 5(11):e15521. PKF115-584: (1R)-2-[12-[(2R)-2-(Benzoyloxy)propyl]-3,10-dihydro-4,9-dihydroxy-2,6,7,11-tetramethoxy-3,10-dioxo-1-perylenyl]-1-methylethylcarbonic acid 4-hydroxyphenyl ester is described by Lepourcelet et. al, Cancer Cell. 2004 January; 5(1):91-102. Each reference is herein specifically incorporated by reference.

Aspects of the invention include contacting a mammalian PSC population with a Wnt signaling antagonist for a period of about 12-60 hours (e.g., about 12-60 hours, about 12-48 hours, about 12-24 hours, about 24-60 hours, about 24-48 hours, about 24-36 hours, about 12 hours, about 18 hours, about 20 hours, about 22 hours, about 24 hours, about 26 hours, about 28 hours, about 30 hours, about 36 hours, about 42 hours, about 48 hours, about 54 hours, or about 60 hours).

The effective dose of a wnt antagonist may be at least about 0.1 µM, at least about 0.5 µM, at least about 1 µM, at least about 2 µM, and usually not more than about 500 µM, not more than about 250 µM, not more than about 100 µM, not more than about 50 M. In some embodiments the effective amount is around about 2 µM.

Aspects of the invention include contacting a mammalian PSC population with a Wnt signaling agonist to produce an agonist-contacted cell population, and further contacting the agonist-contacted cell population with a Wnt signaling antagonist. In some embodiments, the initiation of contact between a mammalian PSC population and a Wnt signaling agonist is about 3 days prior to the initiation of contact between the agonist-contacted cell population and a Wnt signaling antagonist. In some embodiments, the termination of contact between a mammalian PSC population and a Wnt signaling agonist is about 1 day prior to the initiation of contact between the agonist-contacted cell population and a Wnt signaling antagonist, although such a period of time between contacting with the antagonist and the agonist is not required.

In some embodiments, an agonist-contacted cell population is contacted with a Wnt signaling antagonist for a period of at least about 12 hours (e.g., at least about 16 hours, at least about 18 hours, at least about 20 hours, at least about 22 hours, at least about 24 hours, at least about 26 hours, at least about 28 hours, at least about 30 hours, at least about 36 hours, at least about 42 hours, at least about 48 hours, at least about 54 hours, at least about 60 hours, about 12 hours, about 16 hours, about 18 hours, about 20 hours, about 22 hours, about 24 hours, about 26 hours, about 28 hours, about 30 hours, about 36 hours, about 42 hours, about 48 hours, about 54 hours, or about 60 hours).

Cell Culture and Media
Cell Culture

The terms "passaging" or "passage" (i.e., splitting or split) in the context of cell culture are known in the art and refer to the transferring of a small number of cells into a new vessel. Cells can be cultured if they are split regularly because it avoids the senescence associated with high cell density. For adherent cells, such as PSCs, cells need to be detached from the growth surface as part of the passaging protocol. Detachment is commonly performed with the enzyme trypsin and/or other commercially available reagents (e.g., TrypLE, EDTA (Ethylenediaminetetraacetic acid), etc.). A small number of detached cells (e.g., as few as one cell) can then be used to seed a new cell population, e.g., after dilution with additional media. In some embodiments, PSCs are seeded (i.e., plated) at $1.2 \times 10^4$ to $2 \times 10^4$ cells/cm$^2$ of vessel surface area during passaging, which corresponds to roughly 300,000 to 500,000 cells in a commonly used T25 sized tissue culture vessel. Therefore, as used herein, to passage a cell population means to dissociate at least a portion of the cells of the cell population, dilute the dissociated cells, and to plate the diluted dissociated cells (i.e., to seed a new cell population). When stem cells are said to be passaged in a particular type of media, it is meant that after dissociation and dilution, the cells are plated (i.e., a new population is seeded) in the particular type of media. In some embodiments, a PSC population is passaged in media supplemented with a ROCK inhibitor (discussed below).

One difficulty of PSC culture is that PSCs are particularly sensitive to dissociation, which is required for passaging, expansion, cryopreservation, and other applications. When PSCs are completely dissociated into single cells, programmed cell death (apoptosis) is rapidly induced. Recently, it has been discovered that an inhibitor of Rho associated kinase (ROCK) increases the survival rate of dissociated, single PSC cells. Thus, ROCK inhibitors have been used in a variety of applications associated with PSC dissociation such as passaging, expansion, cryopreservation, gene transfer, differentiation induction, and cell sorting (Krawetz et al, Bioessays. 2009 March; 31(3):336-43).

In some embodiments, a subject mammalian PSC population is contacted with a ROCK inhibitor. Any ROCK inhibitor may be used. Suitable ROCK inhibitors include but are not limited to Thiazovivin, Y-27632, GSK429286A, and Fasudil. In some embodiments, a PSC population is passaged in media supplemented with a ROCK inhibitor. As such and as explained above, newly seeded (i.e., plated) dissociated cells are contacted with a ROCK inhibitor for a period of at least 20 hours, (e.g., at least 24 hours, about 20 hours, or about 24 hours). As is known in the art, to remove a supplement (e.g., a ROCK inhibitor), the media is aspirated and replaced with media that is devoid of the supplement.

Two basic methods for the cardiac differentiation of PSCs are currently in use: the formation of embryoid bodies (EBs), and culturing PSCs as a monolayer. Each method relies on progressive sequential inductive environments using growth factors and/or small molecules (Burridge et al., Cell Stem Cell. 2012 January 6; 10 (1):16-28). Methods of the invention do not include the formation of embryoid bodies (EBs), which include suspending PSC colonies to form spherical aggregates. As such, in some embodiments, cells are cultured as a monolayer. In some such embodiments, to enhance the transition from a stem cell state into a differentiated cardiomyocyte. cells are cultured on a matrix. Various suitable matrices are known in the art and are commercially available (e.g., Geltrex/Matrigel, Synthemax, or Vitronectin).

In some embodiments, a laminin matrix is used, e.g. recombinant laminin 521, truncated laminin 511, and the like. The laminin may be used at a concentration of at least about 0.5 µg/cm$^2$, at least about 1 µg/cm$^2$, at least about 2-2.5 µg/cm$^2$. While excess amounts are not harmful, it is desirable for cost to use a minimum amount, i.e. not more than about 50 µg/cm$^2$, not more than about 25 µg/cm$^2$, not more than about 10 µg/cm$^2$.

In some embodiments, prior to contact with a Wnt signaling agonist (described below), a mammalian PSC population is passaged about every 3-5 days (e.g., about every 3 days, about every 4 days, or about every 5 days). In some embodiments, a mammalian PSC population is passaged about 3-5 days (e.g., about 3-4 days, about 4-5 days, about 3 days, about 4 days, or about 5 days) prior to contact with a Wnt signaling agonist. In some embodiments, a mammalian PSC population is passaged about 6-8 days (e.g., about 6-7 days, about 7-8 days, about 6 days, about 7 days, or about 8 days) prior to contact with a Wnt signaling antagonist (described below).

The terms "media" and "medium" are herein used interchangeably. Cell culture media is the liquid mixture that baths cells during in vitro culture.

Maintenance Media

Subject PSCs are cultured in an appropriate liquid nutrient medium. Various media formulations are available (e.g., Dulbecco's Modified Eagle Medium (DMEM), RPMI, Iscove's medium, etc.), are known in the art, and can be used to culture a PSC population prior to contacting a Wnt signaling agonist. The medium may be supplemented with serum or with defined additives. Appropriate antibiotics to prevent bacterial growth and other additives, such as pyruvate (0.1-5 mM), glutamine (0.5-5 mM), 2-mercaptoethanol (1-10×10$^{-5}$ M) may also be included.

The terms "maintenance media", "E8 media", or simply "E8" are used interchangeably herein to refer to a specific media formulation for the culture of PSCs prior to contact with a Wnt signaling agonist. As displayed in Table 1, maintenance media contains, in addition to the components of the commercially available solution of DMEM/F12 with L-Glutamine and HEPES, a final concentration of about 543 ug/ml sodium bicarbonate, about 64 ug/ml L-ascorbic acid 2-phosphate, about 14 ng/ml sodium selenite, about 10.7 ug/ml recombinant human transferrin, about 20 ug/ml recombinant human Insulin, about 100 ng/ml recombinant human FGF2, and about 2 ng/ml recombinant human TGFB1. In some embodiments, prior to contact with the Wnt signaling agonist, a subject PSC population is cultured in maintenance media. In some such embodiments, the maintenance media is supplemented with a ROCK inhibitor for a period of at least 20 hours, (e.g., at least 24 hours, about 20 hours, or about 24 hours) each time the mammalian pluripotent stem cell population is passaged (as described above).

TABLE 1

(E8 media, "Maintenance media")

| Component | [final] | [stock] | volume |
|---|---|---|---|
| DMEM/F12 with L-Glutamine and HEPES | | | 500 ml |
| Sodium bicarbonate | 543 µg/ml | 75 mg/ml | 3.62 ml |
| L-Ascorbic acid 2-phosphate | 64 µg/ml | 64 mg/ml | 500 µl |
| Sodium selenite | 14 ng/ml | 70 µg/ml | 100 µl |
| Recombinant human transferrin | 10.7 µg/ml | 50 mg/ml | 107 µl |
| Recombinant human insulin | 20 µg/ml | 4 mg/ml | 2.5 ml |
| Recombinant human FGF2 | 100 ng/ml | 200 ng/ul | 250 µl |
| Recombinant human TGFB1 | 2 ng/ml | 100 ng/ul | 10 µl |

Minimal Media and Chemically Defined Minimal Media

Minimal media is used in methods of the invention for the culture of cells during contact with the Wnt signaling agonist and antagonist. The term "minimal media" is used herein to refer to a cell culture media formulation that includes a small number of ingredients (e.g., 12, 11, 10, 9, 8, 7, 6, 5, 4, 3, 2, or 1 ingredients) required to be added by the performer of the method, and preferably all ingredients are chemically defined. The term "chemically defined minimal media" is used herein to refer to a minimal media formulation (such that a "chemically defined minimal media" is a type of "minimal media") that does not contain proteins or lysates (e.g., serum albumin, such as bovine serum albumin or human serum albumin) isolated from a an animal blood or serum.

In some embodiments, once a PSC population is contacted with a Wnt signaling agonist in minimal media (e.g., CDM3 media, D3 media, D4 media, D11 media, etc.), the cells are cultured in minimal media throughout the remainder of the method, or until cardiomyocytes are produced. The minimal media can be "CDM3 media", "D3 media" "D4 media", or "D11 media". all of which are defined below. In some embodiments, the minimal media is a chemically defined minimal media. In some such embodiments, the chemically defined minimal media is "CDM3 media." In some embodiments, the minimal media is selected from a group consisting of: CDM3 media, D3 media, 04 media, and D11 media.

A chemically defined minimal media of interest will generally replace BSA (Bovine Serum Albumin) with recombinant albumin, which is conveniently, although not necessarily, recombinant human albumin. Recombinantly produced albumins from other mammals or avians may also be used. The recombinant albumin may be present at a concentration of at least about 50 µg/ml, at least about 100 µg/ml, at least about 250 µg/ml, at least about 500 µg/ml, at least about 750 µg/ml, at least about 1 mg/ml, and not more than about 5 mg/ml, usually not more than about 2.5 mg/ml. In some embodiments the recombinant albumin is present at a concentration of from about 450 to 550 µg/ml.

Chemically defined medium base on RPMI will contain glucose and glutamine at conventional concentrations, e.g. 1-5 mM glutamine, usually about 2 mM glutamine; and glucose at a concentration of from 100-500 mg/liter, from 200-400 mg/liter, or around about 300 mg/liter.

A preferred chemically defined medium also comprises L-ascorbic acid 2-phosphate at a concentration of at least about 50 µg/ml, at least about 100 µg/ml, at least about 250 µg/ml, at least about 500 µg/ml, at least about 750 µg/ml and not more than about 1 mg/ml. In some embodiments the L-ascorbic acid 2-phosphate is present at a concentration of from about 150 to 750 µg/ml, from about 150 to 500 µg/ml, from about 150 to 250 µg/ml.

The inventors formulated a chemically defined minimal media (CDM3 media) for culturing cells of the subject methods that facilitates highly efficient cardiomyocyte differentiation from PSCs. CDM3 media is low cost because the components are inexpensive and readily available. In some embodiments, the chemically defined minimal media is CDM3 media. The term "CDM3 media" or simply "CDM3" as used herein is exemplified by the media formulation displayed in Table 2. CDM3 media (lacking a Wnt signaling agonist and antagonist), includes, in addition to the components of the commercially available solution of RPMI 1640 with glucose and L-glutamine as described in the paragraphs above, recombinant albumin as described above, for example at a concentration of from about 100 µg/ml to about 1 mg/ml, and L-ascorbic acid 2-phosphate as described above, for example at a concentration of from about 150 to 750 µg/ml.

TABLE 2

(exemplary CDM3 media)

| Component | [final] | [stock] | volume |
|---|---|---|---|
| RPMI 1640 (with glucose, 2 mM L-glutamine) | | | 500 mL |
| Recombinant human albumin | 495 µg/mL | 75 mg/mL | 247 mg |
| L-Ascorbic acid 2-phosphate | 213 µg/mL | 64 mg/mL | 106 mg |

The inventors also formulated a minimal media called D3 media for culturing cells of the subject methods that facilitates highly efficient cardiomyocyte differentiation from PSCs. D3 media is low cost because the components are inexpensive and readily available. In some embodiments, the minimal media is D3 media. The term "D3 media" or simply "D3" as used herein refers to the media formulation displayed in Table 3. D3 media (lacking a Wnt signaling agonist and antagonist), contains, in addition to the components of the commercially available solution of RPMI 1640 with glucose and 2 mM L-glutamine, a final concentration of about 2.5 mg/ml Bovine Serum Albumin (BSA), and about 640 µg/ml L-ascorbic acid 2-phosphate. This formulation is still referred to as D3 media when BSA is replaced with Human Serum Albumin (HSA).

TABLE 3

(D3 media, an example of a minimal media)

| Component | [final] | [stock] | volume |
|---|---|---|---|
| RPMI 1640 (with glucose, 2 mM L-glutamine) | | | 500 ml |
| Bovine Serum Albumin (BSA) | 2.5 mg/ml | | 1.25 g |
| L-Ascorbic acid 2-phosphate | 640 µg/ml | | 320 mg |

The inventors also discovered a minimal media called D4 media for culturing cells of the subject methods that facilitates highly efficient cardiomyocyte differentiation from PSCs. D4 media is low cost because the components are inexpensive and readily available. In some embodiments, the minimal media is D4 media. The term "D4 media" or simply "D4" as used herein refers to the media formulation displayed in Table 4. D4 media (lacking a Wnt signaling agonist and antagonist), contains, in addition to the components of the commercially available solution of RPMI 1640 with glucose and 2 mM L-glutamine, a final concentration of about 2.5 mg/ml Bovine Serum Albumin (BSA), about 640 ug/ml L-ascorbic acid 2-phosphate, about 1 ug/ml Linolenic acid, and about 1 ug/ml Linoleic acid. This formulation is still referred to as D4 media when BSA is replaced with Human Serum Albumin (HSA).

TABLE 4

(D4 media, an example of a minimal media)

| Component | [final] | [stock] | volume |
|---|---|---|---|
| RPMI 1640 (with glucose, 2 mM L-glutamine) | | | 500 ml |
| Bovine Serum Albumin (BSA) | 2.5 mg/ml | | 1.25 g |
| L-Ascorbic acid 2-phosphate | 640 µg/ml | | 320 mg |
| Linolenic acid | 1 µg/ml | 100 mg/ml | 5 µl |
| Linoleic acid | 1 µg/ml | 100 mg/ml | 5 µl |

The inventors also discovered a minimal media called D11 media for culturing cells of the subject methods that facilitates highly efficient cardiomyocyte differentiation from PSCs. D11 media is low cost because the components are inexpensive and readily available. The term "D11 media" or simply "D11" as used herein refers to the media formulation (lacking a Wnt signaling agonist and antagonist) containing, in addition to the components of the commercially available solutions of RPMI 1640 with glucose and 2 mM L-glutamine, a final concentration of about 2.5 mg/ml BSA, about 14 ng/ml sodium selenite, about 640 µg/ml L-ascorbic acid 2-phosphate, about 10.7 µg/ml recombinant transferrin, about 1 µg/ml Linolenic acid, about 1 µg/m Linoleic acid, about 2 ng/ml of 3,3',5-Triiodo-L-thyronine. about 2 µg/mL L-Carnitine, about 2 µg/mL D,L-alpha-Tocopherol acetate, and about 100 ng/ml retinyl acetate. This formulation is still referred to as D11 media when BSA is replaced with Human Serum Albumin (HSA).

For further elaboration of general techniques useful in the practice of this invention, the practitioner can refer to standard textbooks and reviews in cell biology, tissue culture, embryology, and cardiophysiology. With respect to tissue culture and embryonic stem cells, the reader may wish to refer to Teratocarcinomas and embryonic stem cells: A practical approach (E. J. Robertson, ed., IRL Press Ltd. 1987); Guide to Techniques in Mouse Development (P. M. Wasserman et al. eds., Academic Press 1993); Embryonic Stem Cell Differentiation in Vitro (M. V. Wiles, Meth. Enzymol. 225:900, 1993); Properties and uses of Embryonic Stem Cells: Prospects for Application to Human Biology and Gene Therapy (P. D. Rathjen et al., Reprod. Fertil. Dev. 10:31, 1998). With respect to the culture of heart cells, standard references include The Heart Cell in Culture (A. Pinson ed., CRC Press 1987), Isolated Adult Cardiomyocytes (Vols. I & II, Piper & Isenberg eds, CRC Press 1989), Heart Development (Harvey & Rosenthal, Academic Press 1998).

Utility

Relative to methods known in the art for producing cardiomyocytes, the above described methods of producing a cardiomyocyte population from a PSC population provide reduced cost, increased efficiency, increased reproducibility, increased flexibility (successful implementation using multiple different stem cell lines), increased scalability, and increased availability of essential components.

In vitro cardiomyocytes produced by the subject methods provide a source of donor cardiomyocytes for cell replacement in damaged hearts. Many forms of heart disease, including congenital defects and acquired injuries, are irreversible because they are associated with the loss of non-regenerative, terminally differentiated cardiomyocytes. Current therapeutic regimes are palliative, and in the case of end-stage heart failure, transplantation remains the last resort. However, transplantation is limited by a severe shortage of both donor cells and organs. In cases of myocardial infarction, 1 billion cells would potentially need to be replaced, highlighting the need for high-throughput and reproducible methodologies for de novo cardiomyocyte production. The subject methods fulfill this need.

As such, the cardiomyocytes may be used for tissue reconstitution or regeneration in a human patient or other subject in need of such treatment. The cells are administered in a manner that permits them to graft or migrate to the intended tissue site and reconstitute or regenerate the functionally deficient area. Special devices are available that are adapted for administering cells capable of reconstituting cardiac function directly to the chambers of the heart, the pericardium, or the interior of the cardiac muscle at the desired location. The cells may be administered to a recipient heart by intracoronary injection, e.g. into the coronary circulation. The cells may also be administered by intramuscular injection into the wall of the heart.

Medical indications for such treatment include treatment of acute and chronic heart conditions of various kinds, such as coronary heart disease, cardiomyopathy. endocarditis, congenital cardiovascular defects, and congestive heart failure. Efficacy of treatment can be monitored by clinically accepted criteria, such as reduction in area occupied by scar tissue or revascularization of scar tissue, and in the frequency and severity of angina; or an improvement in developed pressure, systolic pressure, end diastolic pressure, patient mobility, and quality of life.

The differentiating cells may be administered in any physiologically acceptable excipient, where the cells may find an appropriate site for regeneration and differentiation. The cells may be introduced by injection, catheter, or the like.

The cells of this invention can be supplied in the form of a pharmaceutical composition, comprising an isotonic excipient prepared under sufficiently sterile conditions for human administration. For general principles in medicinal formulation, the reader is referred to Cell Therapy: Stem Cell Transplantation, Gene Therapy, and Cellular Immunotherapy, by G. Morstyn & W. Sheridan eds, Cambridge University Press, 1996; and Hematopoietic Stem Cell Therapy, E. D. Ball, J. Lister & P. Law, Churchill Livingstone, 2000. Choice of the cellular excipient and any accompanying elements of the composition will be adapted in accordance with the route and device used for administration. The composition may also comprise or be accompanied with one or more other ingredients that facilitate the engraftment or functional mobilization of the cells. Suitable ingredients include matrix proteins that support or promote adhesion of the cells, or complementary cell types.

Cells of the subject methods may be genetically altered in order to introduce genes useful in the differentiated cardiomyocyte, e.g. repair of a genetic defect in an individual, selectable marker, etc. Cells may also be genetically modified to enhance survival, control proliferation, and the like. Cells may be genetically altering by transfection or transduction with a suitable vector, homologous recombination, or other appropriate technique, so that they express a gene of interest. In one embodiment, cells are transfected with genes encoding a telomerase catalytic component (TERT), typically under a heterologous promoter that increases telomerase expression beyond what occurs under the endogenous promoter, (see International Patent Application WO 98/14592). In other embodiments, a selectable marker is introduced, to provide for greater purity of the desired differentiating cell.

The cells of this invention can also be genetically altered in order to enhance their ability to be involved in tissue regeneration, or to deliver a therapeutic gene to a site of administration. A vector is designed using the known encoding sequence for the desired gene, operatively linked to a promoter that is either pan-specific or specifically active in cardiomyocytes. Of particular interest are cells that are genetically altered to express one or more growth factors of various types, cardiotropic factors such as atrial natriuretic factor, cripto, and cardiac transcription regulation factors, such as GATA-4. Nkx2.5. and MEF2-C.

Many vectors useful for transferring exogenous genes into target mammalian cells are available. The vectors may be episomal, e.g. plasmids, virus derived vectors such cytomegalovirus. adenovirus, etc., or may be integrated into the target cell genome, through homologous recombination or random integration, e.g. retrovirus derived vectors such MMLV, HIV-1, ALV, etc. For modification of stem cells, lentiviral vectors are preferred. Lentiviral vectors such as those based on HIV or FIV gag sequences can be used to transfect non-dividing cells, such as the resting phase of human stem cells (see Uchida et al. (1998) *P.N.A.S.* 95(20): 11939-44).

Combinations of retroviruses and an appropriate packaging line may also find use, where the capsid proteins will be functional for infecting the target cells. Usually, the cells and virus will be incubated for at least about 24 hours in the culture medium. The cells are then allowed to grow in the culture medium for short intervals in some applications, e.g. 24-73 hours, or for at least two weeks, and may be allowed to grow for five weeks or more, before analysis. Commonly used retroviral vectors are "defective", i.e. unable to produce viral proteins required for productive infection. Replication of the vector requires growth in the packaging cell line.

The host cell specificity of the retrovirus is determined by the envelope protein, env (p120). The envelope protein is provided by the packaging cell line. Envelope proteins are of at least three types, ecotropic, amphotropic and xenotropic. Retroviruses packaged with ecotropic envelope protein, e.g. MMLV, are capable of infecting most murine and rat cell types. Ecotropic packaging cell lines include BOSC23 (Pear et at (1993) P.N.A.S. 90:8392-8396). Retroviruses bearing amphotropic envelope protein, e.g. 4070A (Danos et at, supra.), are capable of infecting most mammalian cell types, including human, dog and mouse. Amphotropic packaging cell lines include PA12 (Miller et al. (1985) Mol. Cell. Biol. 5:431-437); PA317 (Miller et al. (1986) Mol. Cell. Biol. 6:2895-2902) GRIP (Danos et al. (1988) PNAS 85:6460-6464). Retroviruses packaged with xenotropic envelope protein, e.g. AKR env, are capable of infecting most mammalian cell types, except murine cells.

The vectors may include genes that must later be removed, e.g. using a recombinase system such as Cre/Lox, or the cells that express them destroyed, e.g. by including genes that allow selective toxicity such as herpesvirus TK, bcl-xs, etc. Suitable inducible promoters are activated in a desired target cell type, either the transfected cell, or progeny thereof. By transcriptional activation, it is intended that transcription will be increased above basal levels in the target cell by at least about 100 fold, more usually by at least about 1000 fold.

The cells of this invention can be used to prepare a cDNA library relatively uncontaminated with cDNA preferentially expressed in cells from other lineages. For example, cardiomyocytes are collected by centrifugation at 1000 rpm for 5 min, and then mRNA is prepared from the pellet by standard techniques (Sambrook et al., supra). After reverse transcribing into cDNA, the preparation can be subtracted with cDNA from undifferentiated ES cells, other progenitor cells, or end-stage cells from the cardiomyocyte or any other developmental pathway.

The differentiated cells of this invention can also be used to prepare antibodies that are specific for markers of cardiomyocytes and their precursors. Polyclonal antibodies can be prepared by injecting a vertebrate animal with cells of this invention in an immunogenic form. Production of monoclonal antibodies is described in such standard references as U.S. Pat. Nos. 4,491,632, 4,472,500 and 4,444,887, and Methods in Enzymology 73B:3 (1981). Specific antibody molecules can also be produced by contacting a library of immunocompetent cells or viral particles with the target antigen, and growing out positively selected clones. See Marks et al., New Eng. J. Med. 335:730, 1996, and McGuiness et al., Nature Biotechnol. 14:1449, 1996. A further alternative is reassembly of random DNA fragments into antibody encoding regions, as described in EP patent application 1,094,108 A.

Gene expression may be examined before, during, and/or after the production of cardiomyocytes by the subject methods. The expressed set of genes may be compared against other subsets of cells, against PSC cells, against adult heart tissue. and the like, as known in the art. Any suitable qualitative or quantitative methods known in the art for detecting specific mRNAs can be used. mRNA can be detected by, for example, hybridization to a microarray, next-generation sequencing, in situ hybridization, by reverse transcriptase-polymerase chain reaction (rtPCR), or in Northern blots containing poly A mRNA. One of skill in the art can readily use these methods to determine differences in the size or amount of mRNA transcripts between two samples.

Any suitable method for detecting and comparing mRNA expression levels in a sample can be used in connection with the methods of the invention. For example, the mRNA from a sample can be sequenced via next-generation sequencing methods known in the art such as nanopore sequencing (e.g. as described in Soni et al Clin Chem 53: 1996-2001 2007, or as described by Oxford Nanopore Technologies), Illumina's reversible terminator method, Roche's pyrosequencing method (454), Life Technologies' sequencing by ligation (the SOLID platform) or Life Technologies' Ion Torrent platform. Examples of such methods are described in the following references: Margulies et al (Nature 2005 437: 376-80); Ronaghi et al (Analytical Biochemistry 1996 242: 84-9); Shendure (Science 2005 309: 1728); Imelfort et al (Brief Bioinform. 2009 10:609-18); Fox et al (Methods Mol Biol. 2009; 553:79-108); Appleby et al (Methods Mol Biol. 2009; 513: 19-39) and Morozova (Genomics. 2008 92:255-64), which are incorporated by reference for the general descriptions of the methods and the particular steps of the methods, including all starting products, reagents, and final products for each of the steps.

Alternatively, gene expression in a sample can be detected using hybridization analysis, which is based on the specificity of nucleotide interactions. Oligonucleotides or cDNA can be used to selectively identify or capture DNA or RNA of specific sequence composition, and the amount of RNA or cDNA hybridized to a known capture sequence determined qualitatively or quantitatively, to provide information about the relative representation of a particular message within the pool of cellular messages in a sample. Hybridization analysis can be designed to allow for concurrent screening of the relative expression of hundreds to thousands of genes by using, for example, array-based technologies having high density formats, including filters, microscope slides, or microchips, or solution-based technologies that use spectroscopic analysis (e.g., mass spectrometry).

Hybridization to arrays may be performed, where the arrays can be produced according to any suitable methods known in the art. For example, methods of producing large arrays of oligonucleotides are described in U.S. Pat. Nos. 5,134,854, and 5,445,934 using light-directed synthesis techniques. Using a computer controlled system, a heterogeneous array of monomers is converted, through simultaneous coupling at a number of reaction sites, into a heterogeneous array of polymers. Alternatively, microarrays are generated by deposition of pre-synthesized oligonucleotides onto a solid substrate, for example as described in PCT published application no. WO 95/35505.

Methods for collection of data from hybridization of samples with an array are also well known in the art. For example, the polynucleotides of the cell samples can be generated using a detectable fluorescent label, and hybridization of the polynucleotides in the samples detected by scanning the microarrays for the presence of the detectable label. Methods and devices for detecting fluorescently marked targets on devices are known in the art. Generally, such detection devices include a microscope and light source for directing light at a substrate. A photon counter detects fluorescence from the substrate, while an x-y translation stage varies the location of the substrate. A confocal detection device that can be used in the subject methods is described in U.S. Pat. No. 5,631,734. A scanning laser microscope is described in Shalon et al., Genome Res. (1996) 6:639. A scan, using the appropriate excitation line, is performed for each fluorophore used. The digital images generated from the scan are then combined for subsequent analysis. For any particular array element, the ratio of the fluorescent signal from one sample is compared to the fluorescent signal from another sample, and the relative signal intensity determined.

Methods for analyzing the data collected from hybridization to arrays are well known in the art. For example, where detection of hybridization involves a fluorescent label, data analysis can include the steps of determining fluorescent intensity as a function of substrate position from the data collected, removing outliers, i.e. data deviating from a predetermined statistical distribution, and calculating the relative binding affinity of the targets from the remaining data. The resulting data can be displayed as an image with the intensity in each region varying according to the binding affinity between targets and probes.

Pattern matching can be performed manually, or can be performed using a computer program. Methods for preparation of substrate matrices (e.g., arrays), design of oligonucleotides for use with such matrices, labeling of probes, hybridization conditions, scanning of hybridized matrices, and analysis of patterns generated, including comparison analysis, are described in, for example, U.S. Pat. No. 5,800,992.

In vitro cardiomyocytes produced by the subject methods provide also provide a source cells for novel cardiac drug discovery, development, and safety testing. The pharmaceutical industry currently invests approximately $1.5 billion to successfully develop a candidate drug from primary screening to market. Among the drugs that ultimately make it to market, many are later withdrawn due to side effects associated with electrophysiological alterations of the heart (Braam et al., 2010). The use of in vitro cardiomyocytes produced by the subject methods offers the pharmaceutical industry an invaluable tool for preclinical screening of candidate drugs to treat cardiomyopathy, arrhythmia, and heart failure, as well as therapeutics to combat secondary cardiac toxicities. The development of new screens using In vitro cardiomyocytes produced by the subject methods should reduce the time and cost of bringing new drugs to market.

In screening assays for biologically active agents (e.g., small molecule compounds, peptides, viruses, etc.) of the subject cardiomyocytes, usually a culture comprising the subject cardiomyocytes, is contacted with the agent of interest, and the effect of the agent assessed by monitoring output parameters, such as expression of markers, cell viability, electrophysiology, and the like.

Agents of interest for screening include known and unknown compounds that encompass numerous chemical classes, primarily organic molecules, which may include organometallic molecules, inorganic molecules, genetic sequences, etc. An important aspect of the invention is to evaluate candidate drugs, including toxicity testing; and the like.

In addition to complex biological agents, such as viruses, candidate agents include organic molecules comprising functional groups necessary for structural interactions, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Included are pharmacologically active drugs, genetically active molecules, etc. Compounds of interest include chemotherapeutic agents, hormones or hormone antagonists, etc. Exemplary of pharmaceutical agents suitable for this invention are those described in, "The Pharmacological Basis of Therapeutics," Goodman and Gilman, McGraw-Hill, New York, N.Y., (1996), Ninth edition, under the sections: Water, Salts and Ions; Drugs Affecting Renal Function and Electrolyte Metabolism; Drugs Affecting Gastrointestinal Function; Chemotherapy of Microbial Diseases; Chemotherapy of Neoplastic Diseases; Drugs Acting on Blood-Forming organs; Hormones and Hormone Antagonists; Vitamins, Dermatology; and Toxicology, all incorporated herein by reference.

Test compounds include all of the classes of molecules described above, and may further comprise samples of unknown content. Of interest are complex mixtures of naturally occurring compounds derived from natural sources such as plants. While many samples will comprise compounds in solution, solid samples that can be dissolved in a suitable solvent may also be assayed. Samples of interest include manufacturing samples, pharmaceuticals, libraries of compounds prepared for analysis, and the like. Samples of interest include compounds being assessed for potential therapeutic value, i.e. drug candidates.

Compounds, including candidate agents, are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Agents are screened for biological activity by adding the agent to at least one and usually a plurality of cell samples, usually in conjunction with cells lacking the agent. The change in parameters in response to the agent is measured, and the result evaluated by comparison to reference cultures, e.g. in the presence and absence of the agent, obtained with other agents, etc.

The agents are conveniently added in solution, or readily soluble form, to the medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method.

Preferred agent formulations do not include additional components, such as preservatives, that may have a significant effect on the overall formulation. Thus preferred formulations consist essentially of a biologically active compound and a physiologically acceptable carrier, e.g. water, ethanol, DMSO, etc. However, if a compound is liquid without a solvent, the formulation may consist essentially of the compound itself.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

The cells may be freshly isolated, cultured, genetically altered as described above, or the like. The cells may be environmentally induced variants of clonal cultures: e.g. split into independent cultures and grown under distinct conditions, for example with or without virus; in the presence or absence of other biological agents. The manner in which cells respond to an agent, particularly a pharmacologic agent, including the timing of responses, is an important reflection of the physiologic state of the cell.

Parameters are quantifiable components of cells, particularly components that can be accurately measured, desirably in a high throughput system. A parameter can be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc. Characteristically a range of parameter readout values will be obtained for each parameter from a multiplicity of the same assays. Variability is expected and a range of values for each of the set of test parameters will be obtained using standard statistical methods with a common statistical method used to provide single values.

In vitro cardiomyocytes produced by the subject methods can also be used in developmental biology, disease modeling, and post-genomic personalized medicine. Deriving hiPSCs from patients with specific cardiac diseases, differentiating them to cardiomyocytes using the subject methods, and then performing electrophysiological and molecular analyses will provide a powerful tool for deciphering the molecular mechanisms of disease (Josowitz et al., 2011). Studies to date have largely concentrated on recapitulating genetic disease phenotypes in vitro, such as long QT syndromes (Itzhaki et al., 2011a; Matsa et al., 2011; Moretti et al., 2010), Timothy syndrome (Yazawa et al., 2011), and LEOPARD syndrome (Carvajal-Vergara et al., 2010). The possibility of modeling cardiac diseases without a known genetic element is another exciting prospect. The combination of novel drug discovery and efficacy testing with cardiomyocytes derived from patient-specific hiPSCs is a potentially groundbreaking option for personalized medicine.

Kits

Also provided are kits for use in the methods. The subject kits include a Wnt signaling agonist, a Wnt signaling antagonist; and a minimal media. In some embodiments, the Wnt signaling agonist is a compound selected from the group consisting of: TWS119, BIO, CHIR-99021, and combinations thereof. In some embodiments, the Wnt signaling antagonist is a compound selected from the group consisting of: C59, IWR-1, IWP-2, IWP-4, XAV-939, and combinations thereof. In some embodiments, a subject kit includes an antibody specific for a cardiomyocyte marker protein for use in a verifying step. In some such embodiments, the cardiomyocyte marker protein is selected from the group consisting of: cardiac troponin T type 2 (cTNT, TNNT2), myosin light chain 2 a (MLC2a), myosin light chain 2 v (MLC2v), and combinations thereof. In some embodiments, a subject kit includes a cardioactive drug for use in a verifying step. In some embodiments a subject kit includes a mammalian pluripotent stem cell.

In the context of a kit, the minimal media can be provided in liquid or sold form. In some embodiments, al components of the minimal media are provided in liquid form, in some cases as a single solution. In some embodiments, all components of the minimal media are provided in solid form, in some cases as a single mixture. In some embodiments, while all components are provided, some are provided in liquid form and the remainder in solid form. Components of the minimal media, packaged as liquids or as solids, can be packaged independently, as mixtures of more than one component, or as any combination thereof. When provided in liquid form, solutions can be concentrated (e.g., 2×, 5×, 10×, 20×, etc.) so as to require dilution prior to use.

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), flash drive, and the like, on which the information has been recorded. Yet another form of these instructions that may be present is a website address which may be used via the internet to access the information at a removed site.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., room temperature (RT); base pairs (bp); kllobases (kb); picoliters (pl); seconds (s or sec); minutes (m or min); hours (h or hr); days (d); weeks (wk or wks); nanoliters (nl); microliters (ul); milliliters (ml); liters (L); nanograms (ng); micrograms (ug); milligrams (mg); grams ((g), in the context of mass); kilograms (kg); equivalents of the force of gravity ((g), in the context of centrifugation); nanomolar (nM); micromolar (uM), millimolar (mM); molar (M); amino acids (aa); kilobases (kb); base pairs (bp); nucleotides (nt); intramuscular (i.m.); intraperitoneal (i.p.); subcutaneous (s.c.); and the like.

Disclosed here is a chemically defined, growth factor-free, and cost-effective protocol for in vitro cardiac differentiation that is effective for a wide variety of PSCs (including multiple hESC lines and hiPSCs). This highly optimized protocol produces contracting monolayers of cardiomyocytes with high purity and yield in 8-12 days, producing up to 60 million cardiomyocytes per 1 million starting cells. A single operator can produce more than 1×100 cardiomyocytes in a single experiment. The contracting cardiomyocytes produced by this protocol display highly reproducible electrophysiological profiles and pharmacologic responsiveness to known cardioactive drugs.

Materials

Cells: hESC (H9 (WA09), H7 (WA07), HES2 (ES02), or HES3 (ES03), supplied by WiCell Research Institute) (Thomson et al., Science 1998; 282:1145-7; Reubinoff et al., Nat Biotechnol 2000:18:399-404). Viral construct-integrated hiPSC iPS(IMR90)-1 or iPS(IMR90)-4, supplied by WiCell Research Institute) (Yu et al., Science 2009; 324:797-801). Non-viral, non-integrated hiPSC (Gibco Episomal hiPSC line, derived from neonatal CD34+ cord blood, Life Technologies, cat. no. A13777) (Burridge et al., PLoS One 2011; 6:e18293).

Reagents (in addition to those included in Tables 1 and/or 2)
  Dulbecco's Phosphate-buffered saline (D-PBS), pH 7.4, without $CaCl_2$ and $MgCl_2$
  Geltrex LDEV-Free Reduced Growth Factor Basement Membrane Matrix, store at −80° C., thaw at 4° C., thawed vials may be stored at 4° C.
  Recombinant vitronectin, store at −80° C.
  Synthemax II-SC, store at −20° C.
  DMEM F12 with 2.5 mM Glutamine and 15 mM HEPES, store at 4° C.
  0.5 M EDTA, store at RT
  TrypLE Express
  Thiazovivin, 2 mM stocks in DMSO, store at −20° C.
  RPMI 1640 with 2 mM L-glutamine with glucose, store at 4° C.

RPMI 1640 with 2 mM L-glutamine without glucose, store at 4° C.
Recombinant human albumin, store at 4° C.
Human serum albumin, store at 4° C.
Bovine serum albumin, store at 4° C.
UltraPure DNase/RNase-Free Distilled Water, store at RT
CHIR-99021, 10 mM stocks in DMSO, store at −20° C.
C59, 1 mM stocks in DMSO, store at −20° C.
CDM3 media (a "Chemically defined minimal media") (See Table 2 above). Allow recombinant human albumin (or BSA) and L-ascorbic acid-2-phosphate to first dissolve in bottle of RPMI for 30 min at RT. Add additional components, filter sterilize and store at 4° C. for up to 2 weeks.

D3 and D4 media (a "Minimal media") (See Tables 3 and 4 above). Allow BSA (or HSA) and L-ascorbic acid-2-phosphate to first dissolve in bottle of RPMI for 30 min at RT. Add additional components, filter sterilize and store at 4° C. for up to 2 weeks. This method of growing hESC/h PSC as a monolayer has been demonstrated to be successful for the growth of hESC for over 40 passages without karyotypic abnormality. We commonly grow cells for up to 12 passages in this manner to minimize concerns of karyotypic abnormality.

Methods

Compatible methods for hPSC growth. All pluripotent cultures are maintained at 37° C. in a humidified incubator with about 10% $CO_2$ and about 5% $O_2$. Pluripotent cultures can also be maintained at 37° C. in a humidified incubator with about 5% $CO_2$ and atmospheric $O_2$. All differentiation cultures are maintained at atmospheric $O_2$.

Passaging of hPSC with EDTA ("EDTA method" or "EDTA passage"), (volumes provided are for a T25 flask; adjust volumes proportionately for larger vessels). On the first day that cells are ~85% confluent, aspirate medium, wash cells with 0.5 mM EDTA and add 2.5 ml of room temperature EDTA for 3 min at RT. Aspirate EDTA, add 5 ml per flask E8 media, and use a 5 ml pipette dislodge cells. Transfer 500 µl of cell solution to a new Geltrex coated flask and add 4.5 ml of E8 media and 5 µl of 2 mM Thiazovivin. Change E8 media every day for 4 days.

Passaging hPSC with TrypLE for reproducible cell growth, (volumes provided are for a T25 flask; adjust volumes proportionately for larger vessels). On the first day that cells are ~85% confluent, aspirate medium, wash cells with D-PBS and add 1 ml of room temperature TrypLE for ~3-5 min at 37° C. Add 10 ml per flask DMEM/F12 and using a 10 ml dislodge the cells by squirting the medium against the growth surface. Transfer cell suspension to a 15 ml conical tube and centrifuge at 200 g for 4 min at RT, aspirate supernatant and re-suspend pellet in 5 ml of E8 media.

Plate $1.2 \times 10^4$ to $2 \times 10^4$ cells/$cm^2$ (300,000 to 500,000 in a T25) into a Geltrex-coated flask and add E8 media to a final volume of 5 ml and add 5 ul of the ROCK inhibitor 2 mM Thiazovivin. Other ROCK inhibitors, e.g., Y-27632, GSK429288A. Fasudil, and the like may also be used instead of Thiazovivin. As cell growth depends on seeding density, calibrate for confluence after 4 days and passage on a strictly regular 4 day cycle. The most efficient differentiations are obtained when cells are seeded at the lowest initial densities that still achieve near confluence after 4 days of culture. Every day aspirate media and replace with fresh E8 media. $3 \times 10^5$ cells/T25 will result in confluence in 4 days and growth to $3-4 \times 10^6$ cells. Cells must be grown at this rate for successful differentiation.

Directed Cardiac Differentiation Procedure. (volumes provided are for a T25 flask; adjust volumes proportionately for larger vessels) Day 0 (day 4 after passage): Aspirate medium, and replace with 5 mL of minimal media (CDM3, D3, D4, or D11) supplemented with 6 uM of CHIR-99021 (CHIR-99021 can be used at 4-15 µM). Place flasks in a regular ambient $O_2$, 5% $CO_2$ incubator. Day 2: 48 h. Aspirate media and replace with 5 mL of minimal media (CDM3, D3, D4, or D11). Day 3: 72 h. Aspirate media and replace with 5 mL of minimal media (CDM3, D3, D4, or D11) supplemented with 0.5 uM C59 (C59 may be used at 0.5-5 µM). Day 5: Aspirate media and replace with 5 mL of minimal media (CDM3, D3, D4, or D11). From day 5 onwards media should be changed every 2 days with minimal media (CDM3, D3, D4, or D11).

Cardiomyocyte Purification Using Glucose Deprivation. (volumes provided are for a T25 flask; adjust volumes proportionately for larger vessels). Day 11 (Once cells are contracting): Aspirate media and replace with 5 mL of minimal media (CDM3, D3, D4, or D11) made with RPMI containing no glucose. Day 13: Aspirate media and replace with 5 mL of minimal media (CDM3, D3, D4, or D11) made with RPMI containing no glucose. Day 15: swap back to regular minimal media (CDM3, D3, D4, or D11).

Cryopreservation of Purified Cardiomyocytes

We commonly freeze cells at differentiation day 12-15. To freeze cells aspirate media, replace with 1 mL per 10 $cm^2$ room temperature TrypLE. Express and incubate at 37° C. for 5-10 min. Detach cells from growth cell surface with minimal media (CDM3, D3, D4, or D11) and manually triturate to form a single cell suspension. Centrifuge at 200 g for 4 min and resuspend pellet in minimal media (CDM3, D3, D4, or D11) with 10% DMSO. Cells can be frozen at 1-50 million cells per vial for later use.

Results

To eliminate the variability in growth rate commonly experienced with hPSC we further developed our existing monolayer growth method (Burridge et al., PLoS One 2011; 6:e18293). Pluripotent cells were cultured as small clumps of cells using TrypLE or EDTA passaging and in a chemically defined E8 medium (i.e., maintenance media) (containing insulin, FGF2 and TGFB1 as the signaling molecules), modified from Chen et al (Chen et al., Nat Methods 2011; 8:424-9), on a Geltrex/Matrigel, Synthemax (Corning, a synthetic substrate) or recombinant vitronectin matrix. We have simplified the production of E8 so it can be used in general lab settings without media production facilities and for less cost than the commercial variant.

Cell growth and density were found to be major factors in subsequent cardiac differentiation. Cells are passaged to a strict 4-day schedule and seeded at a set density ($1.2 \times 10^4$ cells per $cm^2$), allowing tight control of growth rate prior to differentiation and allowing maximal population doubling time (PD) to be achieved which we demonstrate has a major influence on differentiation efficiency.

After this four days of pluripotent growth cells are approximately 85-90% confluent and differentiation is initiated by media exchange to minimal media (CDM3, D3, D4, or D11). The recombinant human albumin containing variant of this media can currently be made for roughly one eighth the cost of the commercial variant.

From day 0 to day 2 (d0-d2), minimal media (CDM3, D3, D4, or D11) was supplemented with the Wnt signaling agonist CHIR-99021 (6-10 uM 48 h, d0-d2), which triggers canonical Wnt/β-Catenin signaling that leads to the subsequent up-regulation of BMP4 and activin A. Media is then exchanged to non-supplemented minimal media (CDM3, D3, D4, or D11) for 1 day followed by contact with a Wnt signaling antagonist (e.g., C59: 0.5-5 uM, 48 h, d3-d5) for 2 days. At day 5, 7, and 9 minimal media (CDM3, D3, D4, or D11) is exchanged for fresh media, and contraction begins between d7 and d10. At day 11, media is exchanged to a variant of minimal media (CDM3, D3, D4, or D11) without L-glucose that results in the depletion of non-cardiomyocytes due to a lack of glycogen stores. Media was exchanged on day 13 for fresh media lacking glucose. At day 15, media was exchanged for fresh minimal media (CDM3, D3, D4, or D11) (containing glucose). Finally, we demonstrate an efficient and chemically defined method for cryopreservation with ~70-90% viability.

Figure 2:
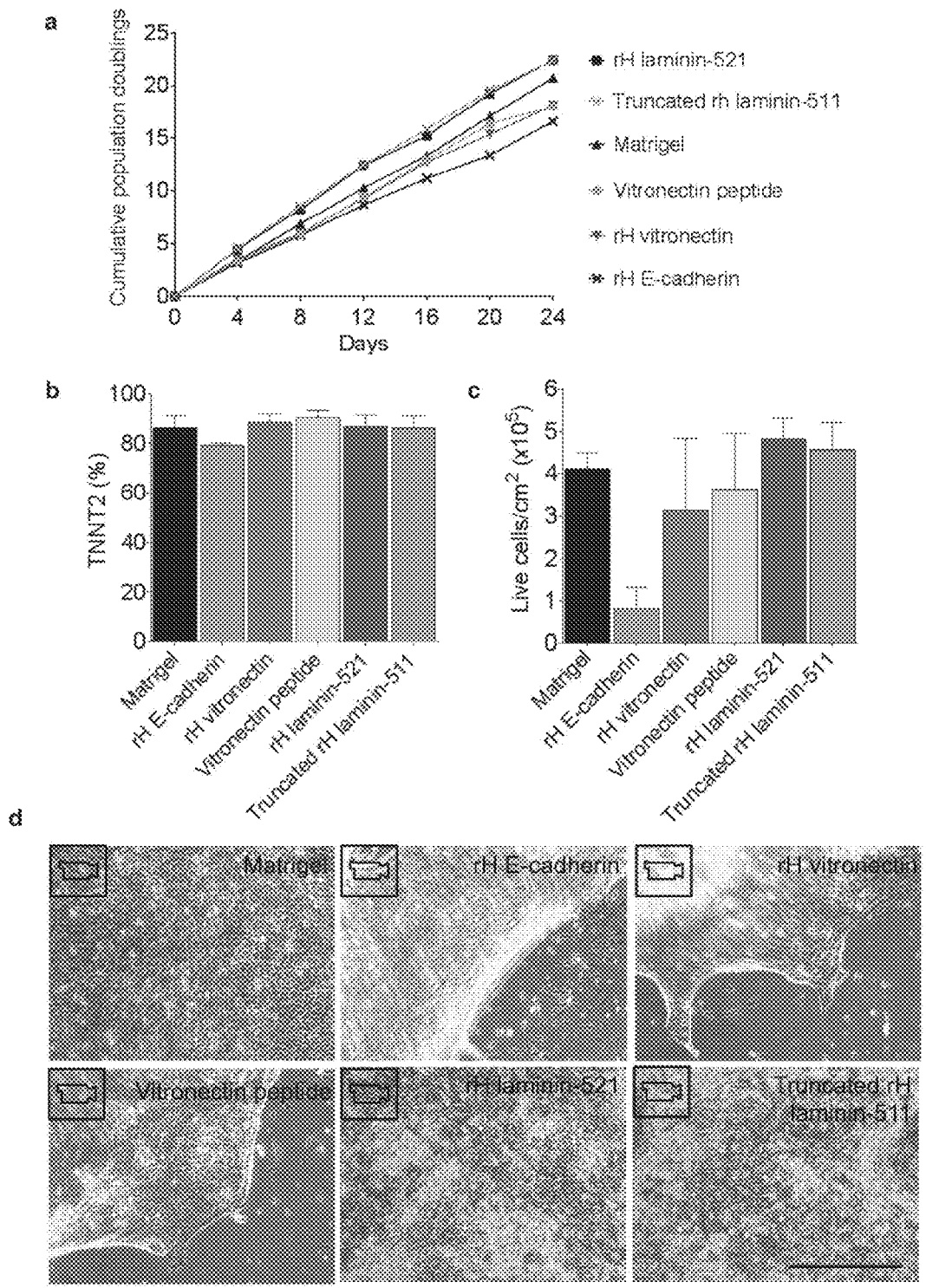
FIG. 2: Cardiac differentiation of hiPSC on chemically defined matrices. a) Comparison of growth rates of hiPSC line 59FSDNC3 in E8 media on optimal concentrations of various defined matrices: rH laminin-521, 2.5 μg/cm; Truncated rH laminin-511, 2 μg/cm; Matrigel, 9 μg/cm; vitronectin pepetide, 625 ng/cm; rH vitronectin. 1 μg/cm; and rH E-cadherin, 1 μg/cm. b) Cardiac differentiation efficiency of cells cultured on defined matrices measured on day 15 by flow cytometry for TNNT2 positive cells, n=3. c) Yield of live cells at differentiation day 15 from cells cultured on various defined matrices, n=4. d) Phase contrast images of day 13 cells demonstrating issues with cell adhesion on some matrices. Of note, combining vitronectin peptides with fibronectin peptides (Pronectin) did not alleviate the adhesion issue.

All previously described cardiomyocyte differentiation methods were performed in either RPMI 1640 supplemented 2% B27 minus insulin (Life Technologies) or StemPro34 (Life Technologies). To form a minimal media in this protocol we considered the constituents of mTeSR1, E8, APEL, our previous xeno-free differentiation medium, and reverse engineered both the B27 minus insulin and StemPro34 (Burridge et al., PLoS One 2011; 6:e18293; Chen et al., Nat Methods 2011; 8:424-9; Ludwig et al., Nat Methods 2006; 3:637-46; Ng et al., Nat Protoc 2008; 3:768-76; Chen et al., J Neurosci Methods 2008; 171:239-47; Yang et al., Nature 2008; 453: 524-8). By subtractive analysis we found that only 2 constituents of B27 minus insulin were required for successful cardiac differentiation. A high concentration of L-ascorbic acid-2-phosphate was capable of replacing the multiple antioxidants from the B27 formula. Cardiac differentiation can be performed in a 3 component media consisting of RPMI, recombinant human albumin, and L-ascorbic acid-2-phosphate. Once the 3 optimal constituents were confirmed, dose-response was assessed to optimize concentrations. (FIGS. 2A and 2B; and Tables 2-4).

We tested a wide range of GSK-3β inhibitors (Wnt signaling agonists) including AR-A014418, 3F8, TWS-119, TDZD-8, BIO and CHIR99021. BIO (2-5 µM) and CHIR-99021 (4-10 µM), were successful at inducing cardiac differentiation in this system. Small molecule WNT inhibitors (Wnt signaling antagonists) found to be effective (at a concentration of 5 µM) include IWR-1, IWP-2, IWP-4, XAV939 and C59. ICG-001 was not found to be effective. Small molecules inhibitors at the later stage of differentiation such as B8431542 and LY364947 (inhibitors of TGFB), dorsomorphin, and LDN193189 (inhibitors of BMP), and SB203580 (inhibitor of p38 MAPK) did not further enhance the differentiation.

The presence of cardiomyocytes was verified in a number of different ways, for example: flow cytometry of cells contacted with an antibody specific for a cardiomyocyte marker (TNNT2); imaging of cells stained with antibodies specific for α-Sarcomeric actin (red) and Troponin T (TNNT2); electrophysiological profiling; and evaluating responsiveness to known cardioactive drugs (e.g., Norepinephrine). Assays performed on multiple different cell lines (including several hESC lines and over 30 hiPSC lines) confirmed that the subject methods are highly consistent and highly efficient, as very little variability was observed among the different cell lines.

Media volumes and days of media exchange were found to be crucial to the protocol with 1 ml per 5 $cm^2$ producing the most efficient differentiation and media changes on day 0, 2, 3, 5, 7 optimal. We found that exposure to hypoxia (during or at any time after contacting the mammalian pluripotent stem cell population with a Wnt signaling agonist), addition of 0.4% PVA (d0-d2), or addition of 1-thioglycerol (d0-d2) severely limited rather than enhanced differentiation. Matrigel overlayer (1:60 at d0) did improve differentiation but also hindered later cell growth.

Example 2

Chemically Defined and Small Molecule-Based Generation of Human Cardiomyocytes

Existing methodologies for human induced pluripotent stem cell (hiPSC) cardiac differentiation are efficient but require the use of complex undefined media constituents that hinder further elucidation of the molecular mechanisms of cardiomyogenesis. Using hiPSCs derived under chemically defined conditions on synthetic matrices, we systematically developed a highly optimized cardiac differentiation strategy employing a chemically defined medium, consisting of just three components: RPMI 1640, L-ascorbic acid 2-phosphate, and rice-derived recombinant human albumin. Along with small molecule-based differentiation induction, this produced contractile sheets of up to 95% TNNT2+ cardiomyocytes at a yield of up to 100 cardiomyocytes for every input pluripotent cell. This methodology was effective in 11 hiPSC lines tested repeatedly from p20 to p83, representing >600 differentiations. This is the first fully chemically defined platform for cardiac specification of hiPSCs and permits elucidation of cardiomyocyte macromolecular/metabolic requirements, providing a minimally complex system for the study of maturation and subtype specification.

Human induced pluripotent stem cells (hiPSCs) are increasingly used in various areas of cardiovascular research, including disease modeling, cardotoxicity screening, drug discovery, and the study of human cardiac development. One aim of the cardiac differentiation field is to provide cells suitable for cellular therapy. These objectives require large numbers ($10^7$-$10^9$) of cells made in a scalable, cheap, and highly reproducible fashion, ideally under chemically defined conditions in which all constituents are chemically known and which lack animal derived products (e.g., bovine serum albumin (BSA), Matrigel, or B27). Differentiation techniques have progressed from early inefficient and variable fetal bovine serum (FBS)-based embryoid body (EB) methods and now multiple methodologies have been shown to produce high purity cardiac troponin T (TNNT2)$^+$ cells with relative ease. Improvements in these methods have largely concentrated on mimicking the embryonic developmental signals that control mesoderm induction: activin/NODAL, BMP, Wnt, and FGF, and subsequent cardiac specification using inhibition of Wnt, BMP, and TGFβ pathways. Despite this progress, little is known of the pathways and macromolecules required for in vitro cardiac differentiation due to the complexity of proprietary media used, the seemingly somewhat autonomous nature of in vitro cardiac differentiation, and the complex secretome involved. The most efficient protocols to date rely on the basal media RPMI 1640 (which is chemically defined) supplemented with 'B27', a complex mix of 21 components (many of animal origin), originally designed for the culture of hippocampal neurons. It is unknown whether B27 components influence differentiation reproducibility, maturation, or subtype specification.

We developed a novel, optimized, and low-cost cardiac differentiation protocol without undefined/proprietary media components that would provide highly reproducible differentiation and allow further understanding of the macromolecules required for cardiac differentiation. This protocol was demonstrated to reproducibly and efficiently differentiate 11 hiPSC lines that were generated under chemically defined conditions. Using this methodology, cardiomyocytes could be produced at >85% purity and enriched to >95% using chemically defined metabolic selection. Cardiomyocytes produced this way were demonstrated to be of a predominantly atnal phenotype that progressively matured to a ventricular phenotype. The complete absence of any undefined or animal derived product in the entire hiPSC culture and differentiation platform makes it ideal for production of large numbers (>10$^9$) of cardiomyocytes to cGMP standards. This methodology is the 'first of its kin' fully chemically defined differentiation system for any pluripotent cell derived lineage. Finally, this system provides a minimally complex and clean platform requiring only three media components and a chemically defined surface for the study of effectors of cardiomyocyte subtype specification and maturation.

Results

Figure 7:
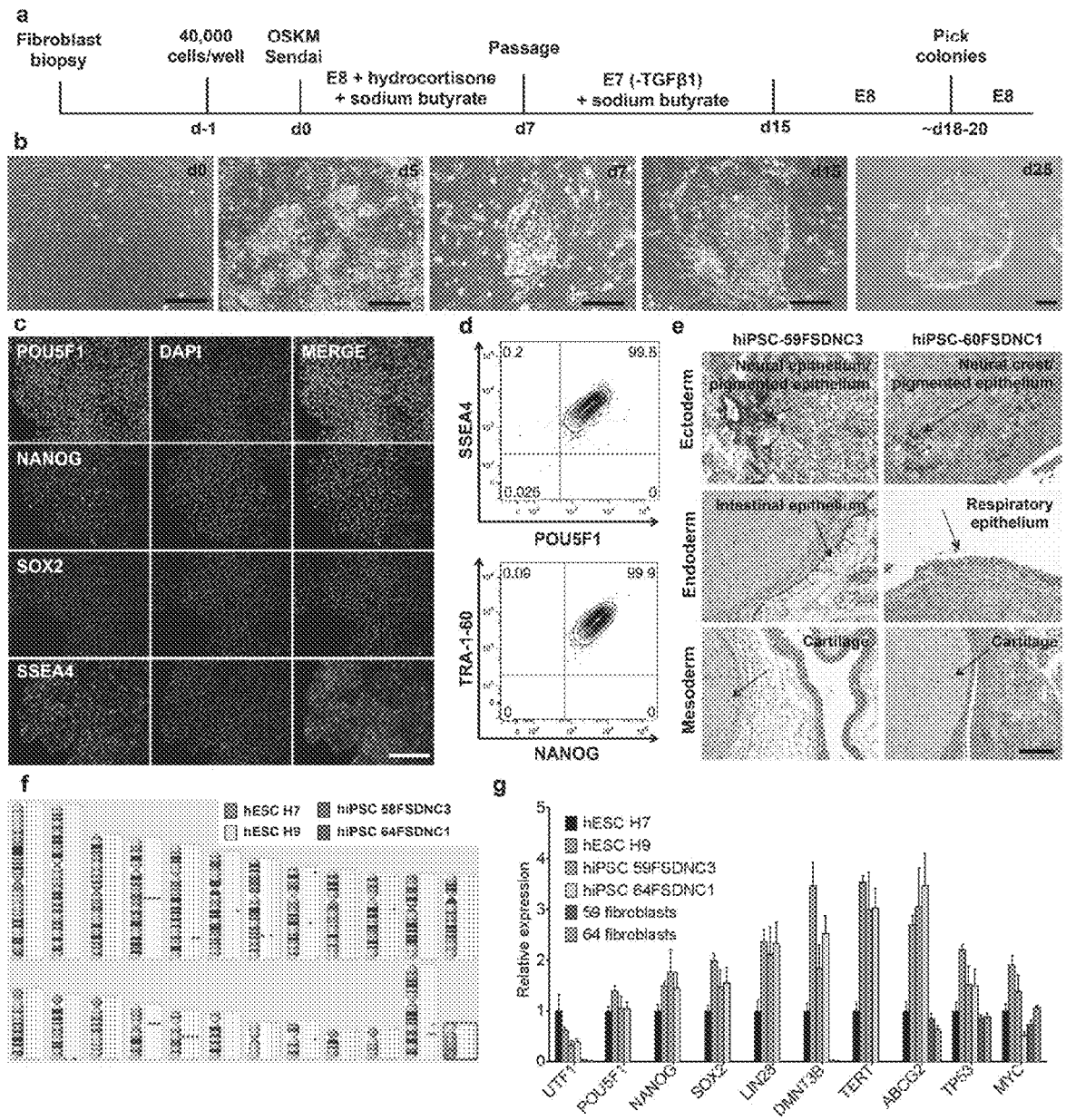
FIG. 7: Generation of hiPSCs using a chemically defined, synthetic matrix, integration-free methodology. a) Timeline of strategy for chemically defined fibroblast reprogramming and phase contrast images of cells during reprogramming. 11 cell lines were made using this strategy from fibroblasts or peripheral blood mononuclear cells, reprogrammed with either Sendai virus (OCT4, SOX2, KLF4, MYC), episomal plasmids (OCT4, SOX2, KLF4, MYCL, LIN28, short hairpin p53), or a single ~9 kb codon optimized mini-intronic plasmid (OCT4, SOX2, KLF4, MYC), Scale bar, 25 μm. b) Phase contrast images of fibroblasts during reprogramming (cell line 59FSDNC3 show as an example). c) Immunofluorescence staining for pluripotency marker expression. Scale bar, 12.5 μm. d) Flow cytometry assessment of pluripotency markers. e) Teratoma assay demonstrating cell types from all three germ layer lineages. Scale bar, 50 μm. f) SNP karyotype of hESC (H7 and H9) and hiPSC (59FSDNC3 and 60FSDNC1) lines demonstrating normal karyotype of hiPSC after reprogramming. g) Real time RT-PCR assessment of genes associated with pluripotency in hiPSC lines (59FSDNC3 and 64FSDNC1), and fibroblasts they were derived from, relative to H7 hESC.
Figure 8:
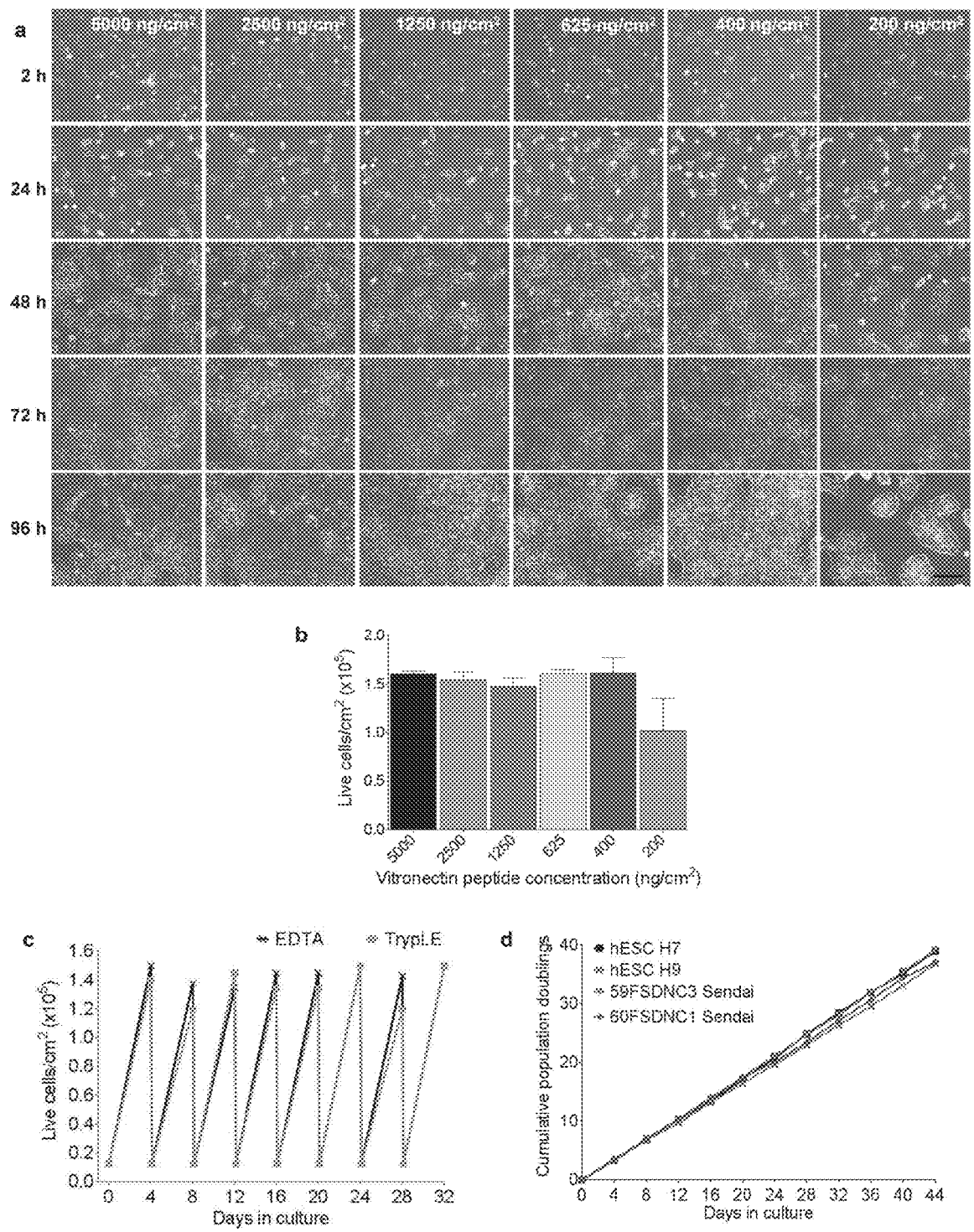
FIG. 8: Growth of hiPSCs in chemically defined media on a synthetic vitronectin peptide matrix. a) Phase contrast images of hiPSC line 59FSDNC3 grown on increasingly lower concentrations of vitronectin peptide. A concentration of 625 ng/cm was used for subsequent studies. Scale bar, 25 μm. b) Cell yields after seeding on vitronectin peptide at 1.25×10 cells/cm and 96 hours of growth, n=3. Cost of vitronectin peptide at a concentration of 625 ng/cm were equivalent to standard costs of Matrigel. c) Comparison of EDTA and TrypLE express for passage on reproducibility of growth rate, cells were split 1:12 for EDTA or counted and plated at $1.25 \times 10_4$ cells/$cm_2$ for TrypLE. d) Cumulative population doublings of two hESC lines (H7 and H9) and two hiPSC lines (59FSDNC3 and 60FSDNC1) grown in E8 medium on vitronectin peptide.
Figure 9:
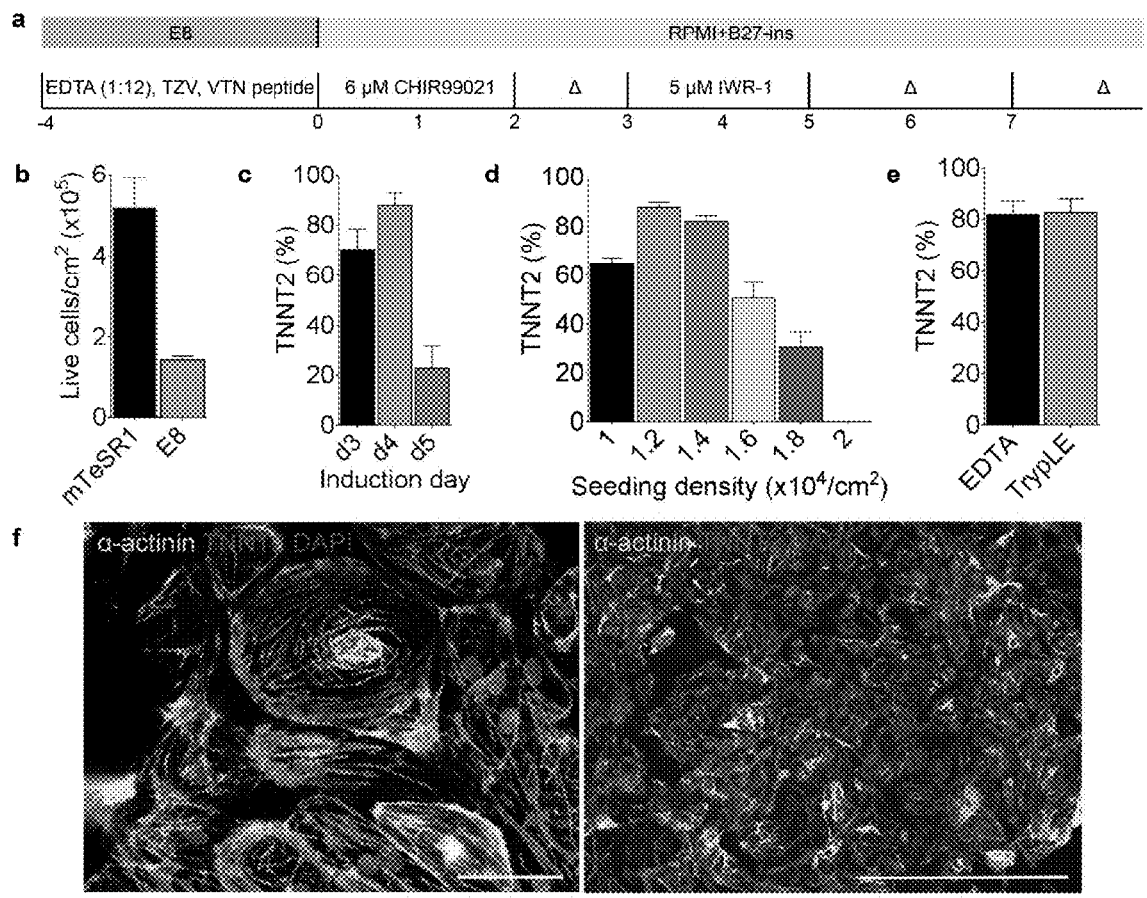
FIG. 9: Modification of existing RPMI+B27-ins small molecule-based differentiation methodology for pluripotent cells cultured under chemically defined conditions. a) Schematic of modified differentiation protocol. b) Yield of live cells after 96 hr culture in either mTeSR1 or E8. mTeSR1 cells were seeded at $1.25 \times 10^5$ cells per $cm_2$ and E8 cells at $1.25 \times 10^4$ cells per $cm^2$, n=3. c) Optimization of number of day after passage for highest efficiency cardiac differentiation efficiency measured by percentage TNNT2 positive cells assessed by flow cytometry, n=3. d) Optimization of seeding density at for subsequent differentiation efficacy, n=3. e) Effect of clump (EDTA) or single cell (TrypLE) passaging method on subsequent differentiation efficiency. f) Immunofluorescence images of cells produced by E8/EDTA/RPMI+B27-ins methodology. Scale bar, 100 μM.

Development of a Chemically Defined Cardiac Differentiation Platform. We first generated eleven pluripotent hiPSC lines under chemically defined conditions (FIG. 7) on a chemically synthesized vitronectin peptide substrate, with nonenzymatic passaging (FIG. 8). Early experiments demonstrated that previous monolayer cardiac differentiation protocols could be adapted to function with hiPSCs grown under chemically defined conditions (FIG. 9). To formulate a chemically defined differentiation protocol, we concentrated on the observation that three unrelated media formations are capable of supporting growth factor-based monolayer cardiac differentiation: RPMI+B27-ins, supplemented StemPro-34, and LI-APEL (Table 5). Initial experiments demonstrated that of the three media examined, RPMI+B27-ins resulted in the most efficient small molecule-based cardiac differentiation. Beginning with the 21 components of B27, we subtracted one component at a time and assessed for continued high efficiency differentiation (Table 6a-c) and also assessed components from two other two media (supplemented StemPro-34 and LI-APEL) that yielded benefits (Table 6d-f). We concluded that hiPSC cardiac differentiation was successful in a media consisting of two three components: RPMI 1640 basal medium, L-ascorbic acid 2-phosphate (AA 2-P), and BSA (Table 6g).

TABLE 5

| RPMI+B27-ins | | LI-APEL | | StemPro-34 based | | Xeno-free varient | |
|---|---|---|---|---|---|---|---|
| | µg/mL | | µg/mL | | µg/mL | | µg/mL |
| RPMI 1640 | | IMDM: F-12, 5% PFHM II | | IMDM | | RPMI | |
| L-glutamine (2 mM) | 300 | L-alanyl-L-glutamine (4 mM) | 892 | L-glutamine (2 mM) | 300 | L-glutamine (2 mM) | 300 |
| BSA | 2500 | Albucult | 5000 | HSA | 5000 | HSA | 5000 |
| Holo transferrin | 5 | Holo transferrin | 54 | Holo transferrin | 250 | | |
| Sodium selenite | 0.014 | Sodium selenite | 0.07 | Sodium selenite | 0.01 | | |
| Ethanolamine | 1 | Ethanolamine | 203 | Ethanolamine | 10 | | |
| | | Insulin | 1 | Insulin | 10 | | |
| | | | Steroids | | | | |
| Corticosterone | 0.02 | | | Hydrocortisone | 0.04 | | |
| Progesterone | 0.006 | | | | | | |
| | | | Lipids | | | | |
| Linoleic acid | 1 | Linoleic acid | 0.1 | Human EX-CYTE | 5 | Chemically defined lipids | 1x |
| Linolenic acid | 1 | Linolenic acid | 0.1 | | | | |
| Lipoic acid | 0.047 | Synthetic cholesterol | 2.2 | | | | |
| | | | Vitamins | | | | |
| Retinol, all trans (vit. A) | 0.1 | L-Ascorbic acid 2-phosphate | 50 | L-Ascorbic acid | 50 | L-Ascorbic acid | 50 |
| Retinol acetate (vit. A) | 0.1 | | | | | | |
| D,L-a-Tocopherol (vit E) | 1 | | | | | | |
| D,L-a-Tocopherol acetate | 1 | | | D,L-a-tocopherol acetate | 0.02 | | |
| Biotin (vit B7) | 0.1 | | | | | | |
| | | | Antioxidants | | | | |
| Catalase | 2.5 | 1-Thioglycerol | 49 | 2-Mercaptoethanol | 4 | 1-Thioglycerol | |
| Glutathione (reduced) | 1 | | | 1-Thioglycerol | 49 | | |
| Superoxidase dismutase | 2.5 | | | | | | |
| | | | Other | | | | |
| T3 (triiodol-l-thyronine) | 0.002 | Polyvinyl alcohol | 500 | | | | |
| L-Carnitine | 2 | | | | | | |
| D(+)-galactose | 15 | | | | | | |
| Putrescine | 16.1 | | | | | | |

Analysis of components of defined media demonstrated effective for hESC cardiac differentiation. The constituent components of four defined media formulae, which have proven successful in either monolayer or embryoid body-based cardiac differentiation, were assessed to begin elucidation of macromolecules essential for cardiac differentiation. Concentration of L-glutamine/GlutaMAX is calculated as total in media including any that is present in the basal media.

TABLE 6

| a<br>21 components<br>subtracting: | | b<br>10 components<br>subtracting: | | c<br>9 components<br>subtracting: | | d<br>9 components<br>with the<br>addition of: | | e<br>9 components<br>(with 4 at 10x)<br>subtracting: | | f<br>6 components<br>subtracting: | | g<br>2 components<br>subtracting: | |
|---|---|---|---|---|---|---|---|---|---|---|---|---|---|
| BSA | 0 | BSA | 0 | BSA | 0 | 2 x BSA | 0 | BSA | | BSA | 0 | BSA | 0 |
| Holo transferrin | 0 | Holo transferrin | 0 | Holo transferrin | 0 | 10 x Holo transferrin | 0 | Holo transferrin | | Holo transferrin | +++ | | |
| Sodium selenite | 0 | Sodium selenite | 0 | Sodium selenite | 0 | 10 x Sodium selenite | +++ | 10 x Sodium selenite | | 10 x Sodium selenite | +++ | | |
| Ethanolamine | ++ | | | | | | | | | | | | |
| Steroids | | Steroids | | Steroids | | Steroids | | Steroids | | Steroids | | Steroids | |
| Corticosterone | 0 | Corticosterone | ++ | | | Hydrocortisone | + | | | | | | |
| Progesterone | ++ | | | | | | | | | | | | |
| Lipids | | Lipids | | Lipids | | Lipids | | Lipids | | Lipids | | Lipids | |
| Linoleic acid | 0 | Linoleic acid | 0 | Linoleic acid | 0 | 10 x Linoleic acid | + | Linoleic acid | 0 | Linoleic acid | +++ | | |
| Linolenic acid | 0 | Linolenic acid | 0 | Linolenic acid | 0 | 10 x Linolenic acid | + | Linolenic acid | 0 | Linolenic acid | +++ | | |
| Lipoic acid | ++ | | | | | Chemically defined lipids | ++ | | | | | | |
| Vitamins | | Vitamins | | Vitamins | | Vitamins | | Vitamins | | Vitamins | | Vitamins | |
| Retinol, all trans (vit. A) | ++ | | | | | 10 x L-ascorbic acid 2-phosphate | +++ | 10 x L-ascorbic acid 2-phosphate | 0 | 10 x L-ascorbic acid 2-phosphate | 0 | 10 x L-ascorbic acid 2-phosphate | 0 |
| Retinol acetate (vit A) | 0 | Retinol acetate (vit A) | 0 | Retinol acetate (vit A) | 0 | 10 x Retinol acetate (vit A) | +++ | 10 x Retinol acetate (vit A) | +++ | | | | |
| D,L-a-tocopherol (vit E) | ++ | | | | | | | | | | | | |
| D,L-a-tocopherol acetate | 0 | D,L-a-tocopherol acetate | 0 | D,L-a-tocopherol acetate | 0 | 10 x D,L-a-tocopherol acetate | +++ | 10 x D,L-a-tocopherol acetate | +++ | | | | |
| Biotin (vit B7) | ++ | | | | | | | | | | | | |
| Antioxidants | | Antioxidants | | Antioxidants | | Antioxidants | | Antioxidants | | Antioxidants | | Antioxidants | |
| Catalase | ++ | | | | | 1-thioglycerol | 0 | | | | | | |
| Glutathione (reduced) | ++ | | | | | 1-mercaptoethanol | 0 | | | | | | |
| Superoxidase dismutase | ++ | | | | | | | | | | | | |
| Other | | Other | | Other | | Other | | Other | | Other | | Other | |
| T3 (triiodol-l-thyronine) | 0 | T3 (triiodol-l-thyronine) | 0 | T3 (triiodol-l-thyronine) | 0 | 10 x T3 (triiodol-l-thyronine) | +++ | 10 x T3 (triiodol-l-thyronine) | +++ | | | | |
| L-carnitine | 0 | L-carnitine | 0 | L-carnitine | 0 | 10x L-carnitine | 0 | | | | | | |
| D(+)-galactose | ++ | | | | | Polyvinyl alcohol | 0 | | | | | | |
| Putrescine | ++ | | | | | | | | | | | | |

Analysis of components of defined media demonstrated effective for hiPSC cardiac differentiation.

a) Each of the 21 components of the media supplement "B27 without insulin," were substracted one a time.

Results were scored 0, no cardiac differentiation or cell death; +, some contraction; ++, >50% contraction; +++, and >75% contraction.

b) A second medium was formulated using the 10 components demonstrated to be essential in a) and each component substracted one at a time. Only corticosterone was dispensable.

c) Subtraction of any component from the 9-component media was not viable.

d) Assessment of the addition of logarithmically higher or lower concentrations (x 0.1 or x 10) or the addition of components from any of the three other media formulae detailed in Table 5.

e). A third medium was formulated with the four increased concentrations from d) and then each component was subtracted to find which are still necessary.

f) A fourth 6-component medium was formulated and then component substracted.

g) The final 3-component medium from which CDM3 was optimized.

Figure 10:
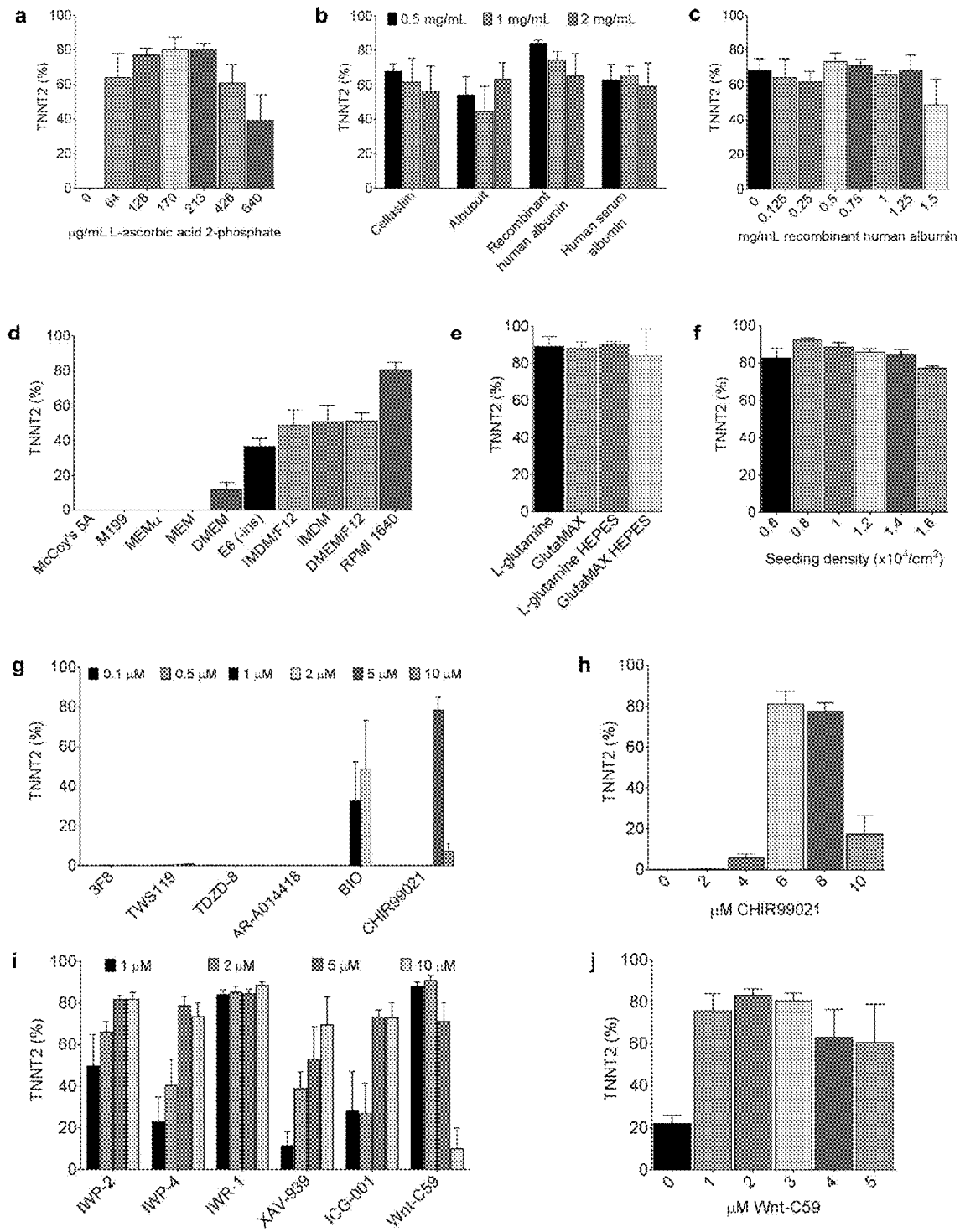
FIG. 10: Optimization of chemically defined differentiation media and small molecules. a) Optimal dose of L-ascorbic acid 2-phosphate, n=7. b) Optimization of recombinant human albumin supplier, n=3. c) Optimization of rHA dose, Qualitatively 500 μg/mL rHA produced the most suitable contracting monolayers whereas 750 μg/mL and above were more likely to have more three-dimensional structures, n=7. d) Optimization of basal media, n=3. e) Assessment of different RPMI 1640 media variants, n=3. f) Optimization of pluripotent cell seeding density, n=3. g) Optimization of GSK3β inhibitor; only BIO and CHIR99021 did not cause total cell death, n=3. h) Optimization of CHIR99021 dose, n=4. i) Optimization of Wnt inhibitor dose, n=3. j) Optimization of Wnt-C59 dose, n=4.

Optimization of a chemically defined cardiac differentiation medium. To confirm the full optimization of this formula and protocol, we further fine-tuned component concentrations andtiming. We showed that total cell death was seen without AA 2-P (FIG. 10a). To make the formula chemically defined and xeno-free, we replaced the BSA with recombinant human albumin (rHA) (FIG. 10b-c). Although it was possible to differentiate cells without rHA in an entirely protein-free medium and produce ~65% TNNT2+ cells, the yield was drastically reduced. To further probe the role of rHA in the formula, we attempted to replace it with polyvinyl alcohol (PVA), which prevents sheer-stress in a similar manner to rhA. Combined with varying doses of AA 2-P, PVA did not increase differentiation yield over that of RPMI 1640 with AA 2-P alone. Likewise, varying doses of AA 2-P without rHA did not improve yield. These data suggest that neither the sheer-stress prevention nor the antioxidant properties of rHA necessitates its inclusion in this formula.

The most effective basal medium was RPMI 1640 (FIG. 10d-e). Efficient differentiation was achieved over a broader range of initial seeding densities than those demonstrated in RPMI+B27-ins (FIG. 10f), suggesting improved differentiation robustness when using in this final media formulation which we termed CDM3 (chemically defined medium, 3 components). We next assessed a range of small molecules with GSK3B inhibitory activity to identify if any had increased mesoderm induction potential in comparison to CHIR99021. Out of six GSK3B inhibitors tested: only BIO and CHIR99021 were successful at inducing any suitable cardiac differentiation and many were found to be highly toxic (FIG. 10g-h).

We also assessed alternative small molecule Wnt inhibitors of which numerous were found to be similarly effective despite the differences in inhibition mechanism (FIG. 10i-j). For example, IWR-1 stabilizes the β-catenin destruction complex while IWP-2 and Wnt-C59 inhibit the acyltransferase PORCN involved in Wnt production. Next we analyzed the importance of the timing of canonical Wnt signaling activation with CHIR99021 and Wnt signaling inhibition with Wnt-C59. We modified the process by either lengthening or shortening the duration of doses and including media changes between and after small molecule doses. We discovered that application of CHIR99021 for 2 days followed by Wnt-C59 for 2 days was optimal (FIG. 11). This short biphasic Wnt modulation was not optimal in RPMI+B27-ins, suggesting that factors slowing response to Wnt induction may be present in RPMI+B27-ins.

The final protocol (FIG. 1a) and formula (FIG. 1b) were demonstrated to produce cardiomyocytes at equivalent efficiencies (FIG. 1c,e) and yields as our optimized RPMI+B27-ins protocol (FIG. 1d). Minimal cell death was seen throughout differentiation (FIG. 12) and contraction began at days 7-9.

Assessment of Developmental Pathways Essential for Chemically Defined Cardiac Differentiation. We have previously proposed that Wnt signaling initiated paracrine feedback loop via FGF, BMP, Wnt and activin/NODAL signaling and may be responsible for mesoderm induction in hiPSC. To test this hypothesis and to determine if more specific signaling pathway control could improve differentiation robustness, we inhibited the six major pathways associated with in vivo cardiac differentiation—FGF, activin/NODAL, BMP, Wnt, TGFβ, and MAPK to assess their roles during mesoderm induction and cardiac specification (FIG. 1f). Inhibitors of each of these pathways were added at differentiation day 0-2 or day 1-2. Our results demonstrated that FGF, activin/NODAL, BMP, and Wnt signaling were all essential for mesoderm induction, as inhibition of these pathways hindered efficient cardiac differentiation. By contrast, TGFβ and p38 MAPK were dispensable (FIG. 1f). We wanted to know whether the inhibition of these pathways could improve the robustness of subsequent cardiac specification. and we therefore added the above inhibitors during differentiation days 2-4, 3-4, and 4-6. We found that after day 3, none of the six pathways was required as inhibition did not diminish or enhance differentiation efficiency (FIG. 1g).

Determination that Laminin-Based Matrices are Most Suitable for Cardiac Differentiation. Although we found a synthetic vitronectin peptide matrix suitable for pluripotent culture and cardiac differentiation in CDM3, the highly motile cardiomyocyte monolayers produced would detach from the surface at ~day 15 (FIG. 2d), reducing the yield and increasing variability (FIG. 2c). This lack of long-term adhesion during the differentiation was present irrelevant of vitronectin peptide concentrations and could be resolved by passaging and replating onto new matrix, yet we sought to find a more suitable solution. We assessed culture of hiPSC in E8 medium and subsequent differentiation on other defined matrices: recombinant human (rH) Ecadherin, rH vitronectin, rH laminin-521, truncated rH laminin-511, human fibronectin, or a fibronectin mimetic (FIG. 2a). Chemically defined long-term maintenance of pluripotency in E8 was successful on all surfaces except those based on fibronectin. Laminin-based matrices demonstrated higher growth rates than vitronectin peptide (FIG. 2a), potentially due to the established role of laminin-511/-521 interacting with α6β1 integrin and activating the PI3K/Akt pathway. Cells cultured on each of the five successful matrices (>6 passages) were then differentiated in CDM3. Although all matrices produced efficient differentiations (FIG. 2b), the laminin matrices were both successful for maintaining long-term adhesion during chemically defined cardiac differentiation (FIG. 2d), but prohibitively expensive for large-scale application. Therefore, further characterization was performed in vitronectin peptide.

Figure 3:
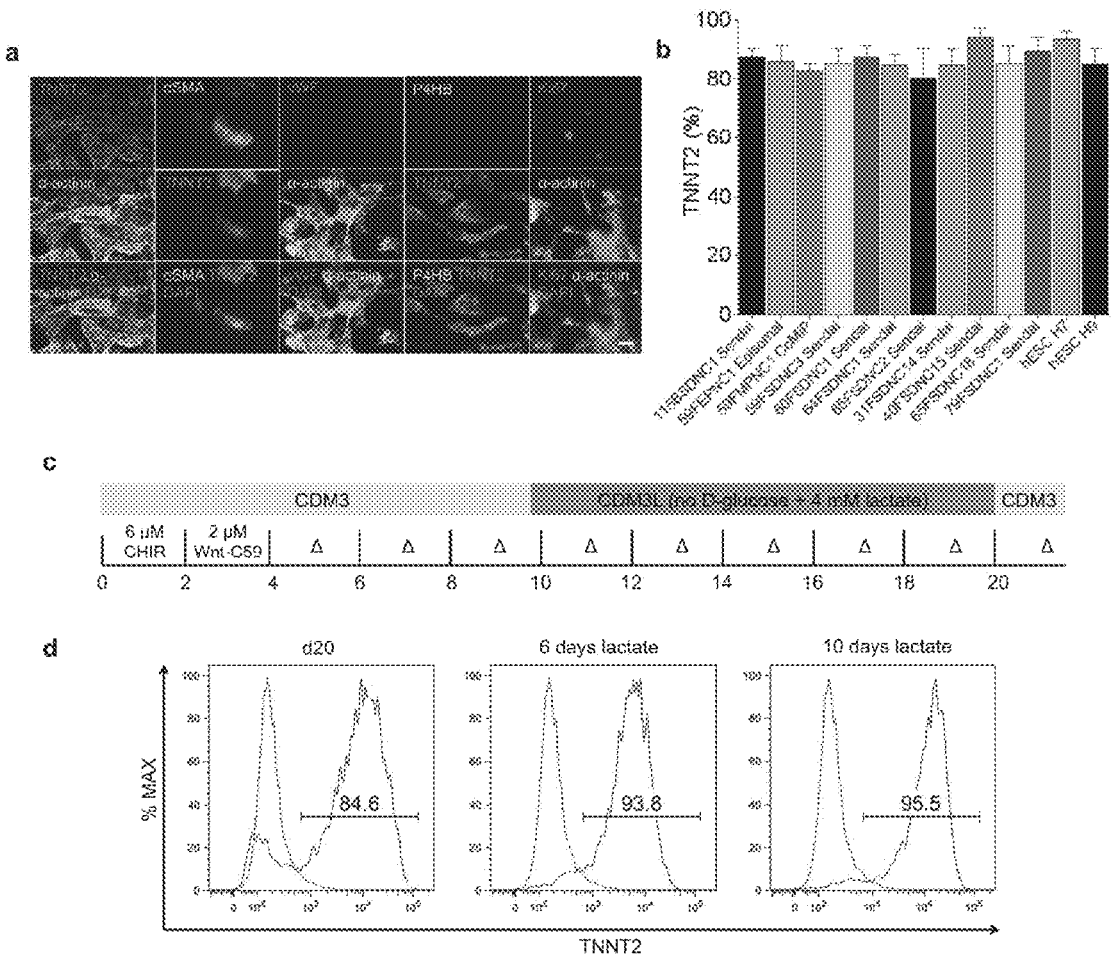
FIG. 3: Characterization and purification of cardiomyocytes produced by chemically defined differentiation. a) Immunofluorescent staining for TNNT2 and α-actinin (cardiomyocyte structural markers), α-smooth muscle actin (primitive cardiomyocytes), vWF (endothelial cells), P4HB (fibroblasts), and Ki67 (proliferating cells). Scale bar, 100 μm. b) Efficiency of chemically defined cardiac differentiation measured by flow cytometry for TNNT2+ on day 15 cells in a range of peripheral blood or fibroblast-derived hiPSC and hESC lines cultured under chemically defined conditions with Sendai virus, 'Yamanak' episomal plasmids, or a mini intronic plasmid (CoMiP). Both hiPSCs and hESC lines were differentiated in CDM3. c) Schematic of chemically defined cardiac differentiation including purification by metabolic selection. CDM3L: CDM3 without D-glucose and supplemented with 4 mM lactate. d) Effect of chemically defined metabolic purification measured by flow cytometry for TNNT2 on day 20 cells. 6 days lactate, day 10-16; 10 days lactate, day 10-20.

Demonstration of Efficacy of Final Formulation Across a Wide Variety of Human Pluripotent Stem Cell Lines and Passage Numbers. Cells were positive for cardiac markers (TNNT2, α-actinin) and the immature cardiomyocyte marker smooth muscle actin (βSMA), and negative for the endothelial marker vWF and fibroblast marker P4HB. A small proportion of cells were positive for the proliferation marker Ki67 (FIG. 3a). One criticism of established cardiac differentiation protocols is the lack of efficacy across multiple hESC and hiPSC lines. To address this issue, we tested our protocol with a variety of hESC and hiPSC lines (described in Methods); all demonstrated 80-95% differentiation efficiency as assessed by flow cytometry for TNNT2 (FIG. 3b) and produced yields of greater than $3 \times 10^5$ cardiomyocytes per $cm^2$ of cell culture surface. The eight Sendai virus-derived lines were maintained using the E8/EDTA culture method for more than 1 year and overall all lines repeatedly differentiated efficiently from passage 25 to >80. Cardiomyocytes could be generated and maintained in these chemically defined conditions for >200 days, suggesting minimal macromolecular requirements for long-term cardiomyocyte maintenance.

Purification of hiPSC-derived Cardiomyocytes Using Metabolic Selection. It has been demonstrated that culturing hiPSC-derived cardiomyocytes in glucose-free MEMα-supplemented with FBS and lactate can enrich cells from 4.5% to 98.0% α-actinin positive. Because B27 supplement contains a source of glucose (D(+)-galactose), media formulas with this supplement are not suitable for this methodology. Replacing the RPMI 1640 in our CDM3 formula with RPMI 1640 without glucose and supplementing with sodium DL-lactate (FIG. 3c), we found that 6-10 days of glucose deprivation (day 10-16 or day 10-20) was able to purify cardiomyocytes from ~85% TNNT2$_+$ to >95% (FIG. 3d). This simple methodology can be used to provide highly pure hiPSC-derived cardiomyocytes with minimal experimental complexity.

Figure 4:
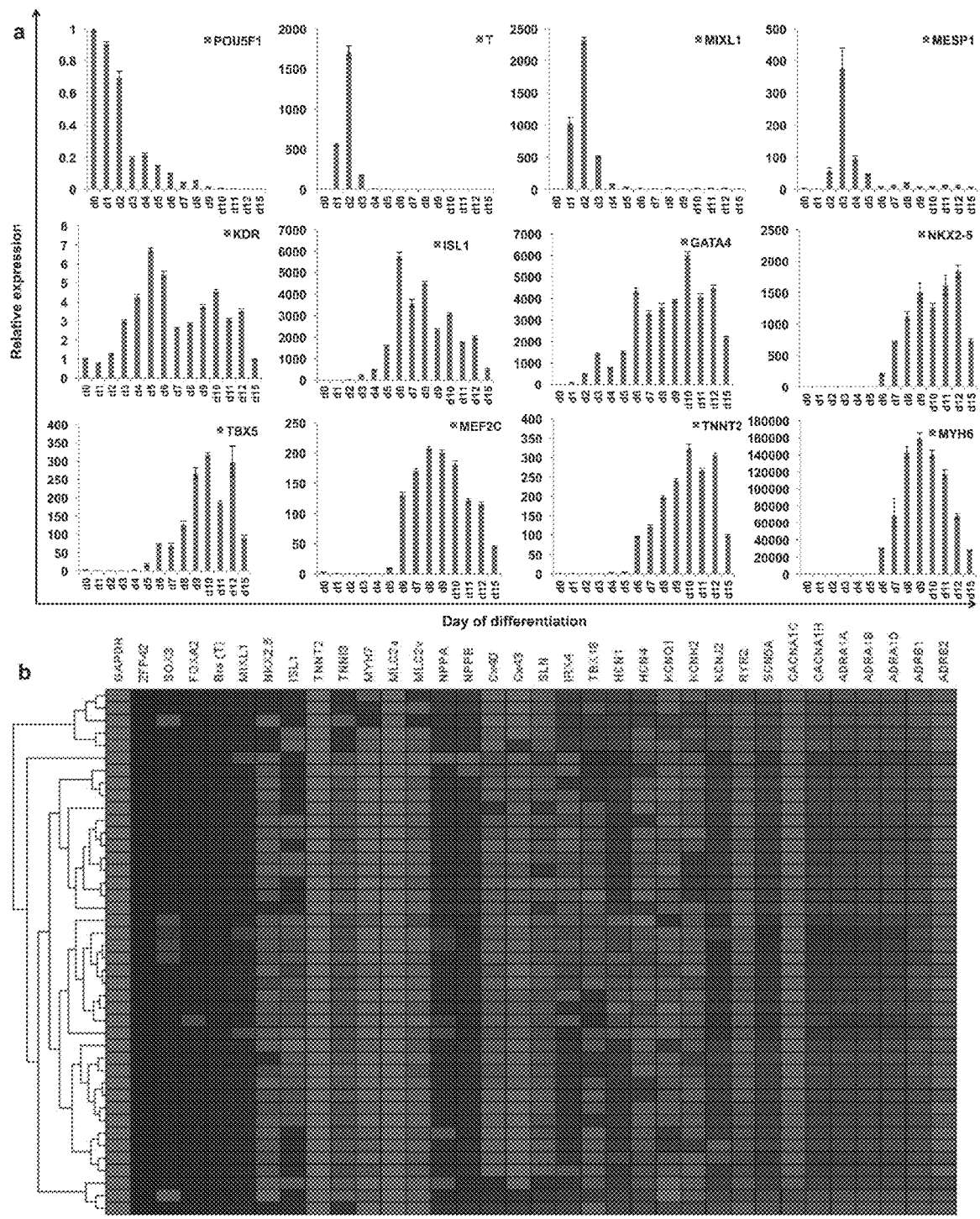
FIG. 4: Gene expression during differentiation and in cardiomyocytes produced under chemically defined conditions. a) Real time RT-PCR for markers of pluripotency (POU5F1), mesoderm (T, MIXL1), cardiac mesoderm (MESP1, KDR), committed cardiac progenitors (ISL1, GATA4, NKX2-5, TBX5, MEF2C), and cardiomyocytes (TNNT2, MYH6). Samples used in this analysis were matched pairs for phase contrast images. b) Assessment of gene expression heterogeneity using single cell real time RT-PCR of day 20 cardiomyocytes differentiated in CDM3.
Figure 12:
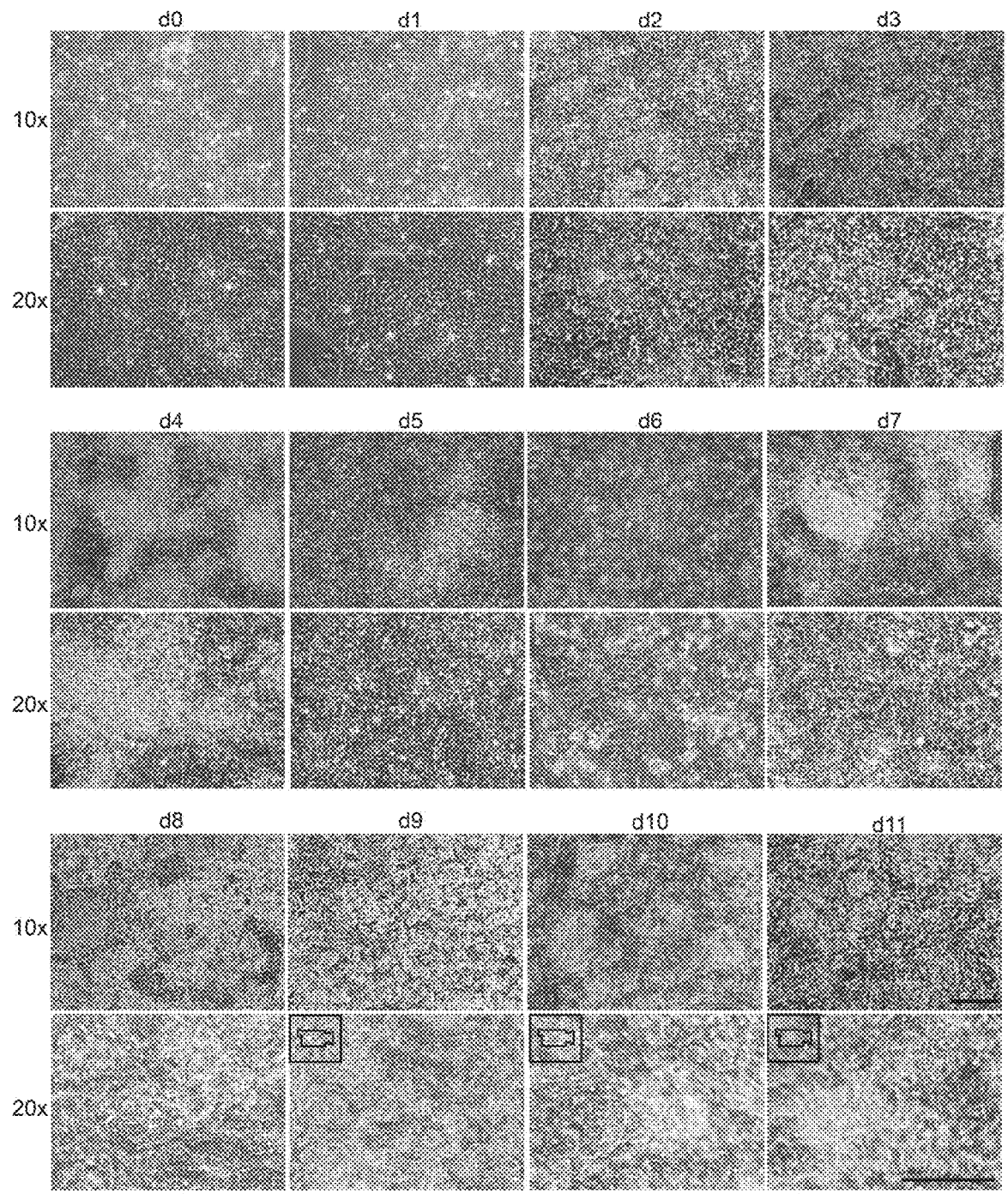
FIG. 12: Phase contrast images of hiPSC during chemically defined differentiation. Scale bar, 25 μM.

Characterization Of Atrial and Ventricular Cardiomyocyte Subtypes Produced Under Chemically Defined Conditions. To characterize cardiomyocytes produced under chemically defined conditions, samples were taken every day during differentiation and assessed by real-time RT-PCR (FIG. 4a and FIG. 12). Gene expression patterns were consistent with those from previous differentiation strategies and with embryonic development. The pluripotency marker POU5F1 was rapidly downregulated at day 2 at the same time as upregulation of the mesoderm markers T and MIXL1, followed by the cardiac mesoderm marker MESP1. Early cardiomyocyte markers (KDR, ISL1, and GATA4) became highly expressed from days 5-6, with later markers (NKX2-5, TBX5, and MEF2C) peaking at days 8-9. Finally the cardiomyocyte structural genes TNNT2 and MYH6 peaked at days 8-10. Single cell real-time RT-PCR on day 20 cardiomyocytes (not metabolically selected) showed substantial homogeneity among cells (FIG. 4b), although significant variation was noted in the expression of the ion channels HCN1, HCN4, KCNQ1, and KCNH2.

Figure 5:
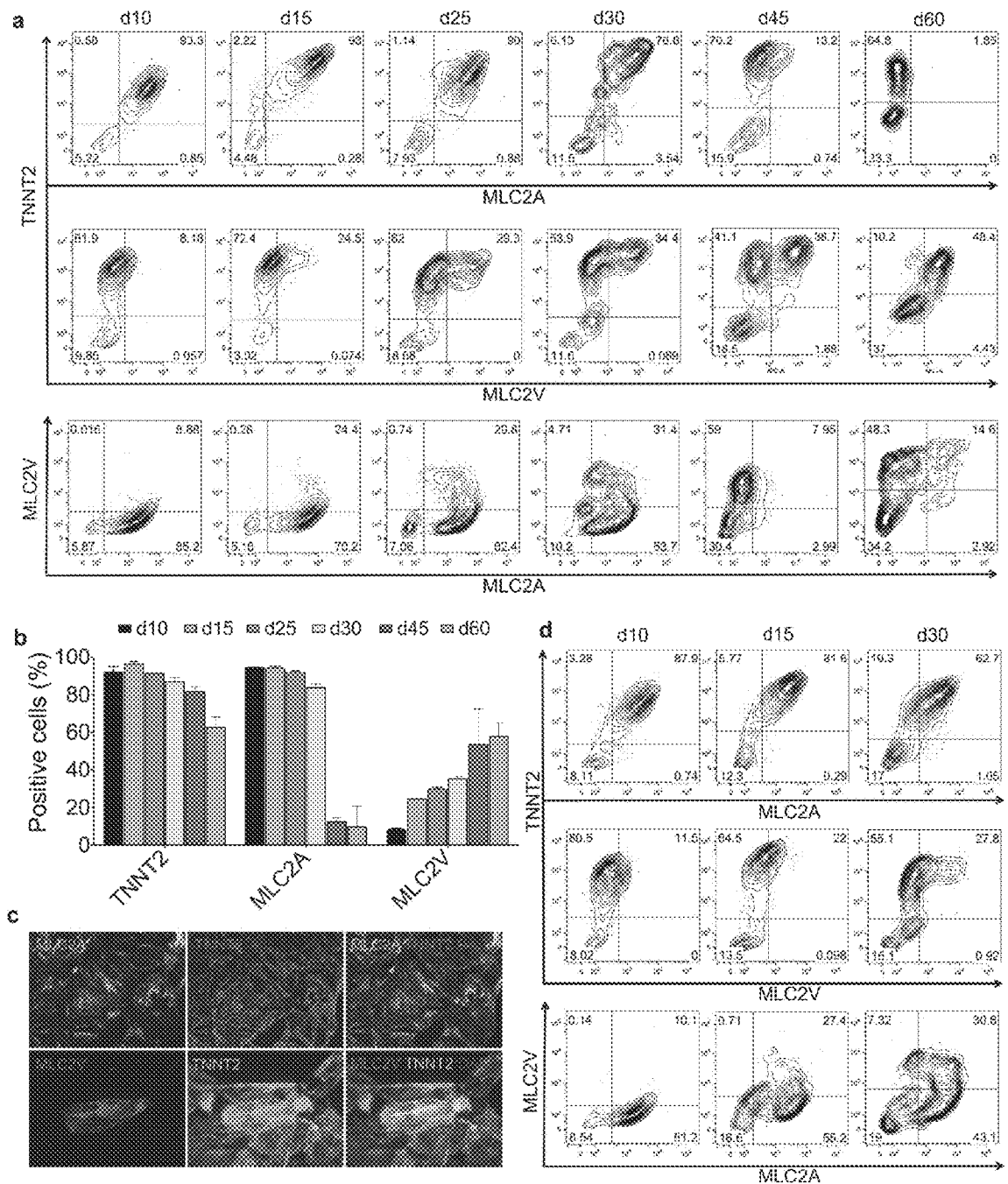
FIG. 5: Characterization of atrial vs. ventricular profile of cardiomyocytes produced under chemically defined conditions. a) Flow cytometry assessment of expression of cardiac troponin T (TNNT2), atrial myosin light chain 2 (MLC2A), and ventricular myosin light chain (MLC2V) in cardiomyocytes derived and maintained in CDM3 at differentiation day 10 through day 60. b) Graphical representation of the above data. c) Immunofluorescence staining of day 20 cardiomyocytes with the same antibodies used for flow cytometry to demonstrate specificity. d) Flow cytometry assessment of expression of TNNT2, MLC2V, and MLC2A in cardiomyocytes differentiated using RPMI+B27-ins media at differentiation day 10 through day 30.

As shown in FIG. 4b, many cells co-expressed markers of atrial (NPPA, CX40, and SLN), ventricular (MLC2V, IRX4, and NPPB), and nodal cells (TBX18), suggesting that the cells are immature. To assess the maturation of the atrial vs. ventricular phenotype of cardiomyocytes derived under chemically defined conditions, we next used flow cytometry of cells at differentiation d10 and d60 (FIG. 5a). Early cardiomyocytes (day 10) demonstrated an atrial TNNT2$_+$ MLC2A$_+$MLC2V$_-$ phenotype at day 10 and cells progressively became less atrial (MLC2A$_+$) and increasingly ventricular (MLC2V$_+$) (FIG. 5b). MLC2A was specifically seen to decrease dramatically after day 30. MLC2V expression reached 60% at day 60. Antibody specificity was confirmed by immunofluorescence staining (FIG. 5c). Similar flow cytometry results were seen in cells differentiated in RPMI+B27-ins (FIG. 5d), suggesting minimal effect of media on subtype specification.

Figure 6:
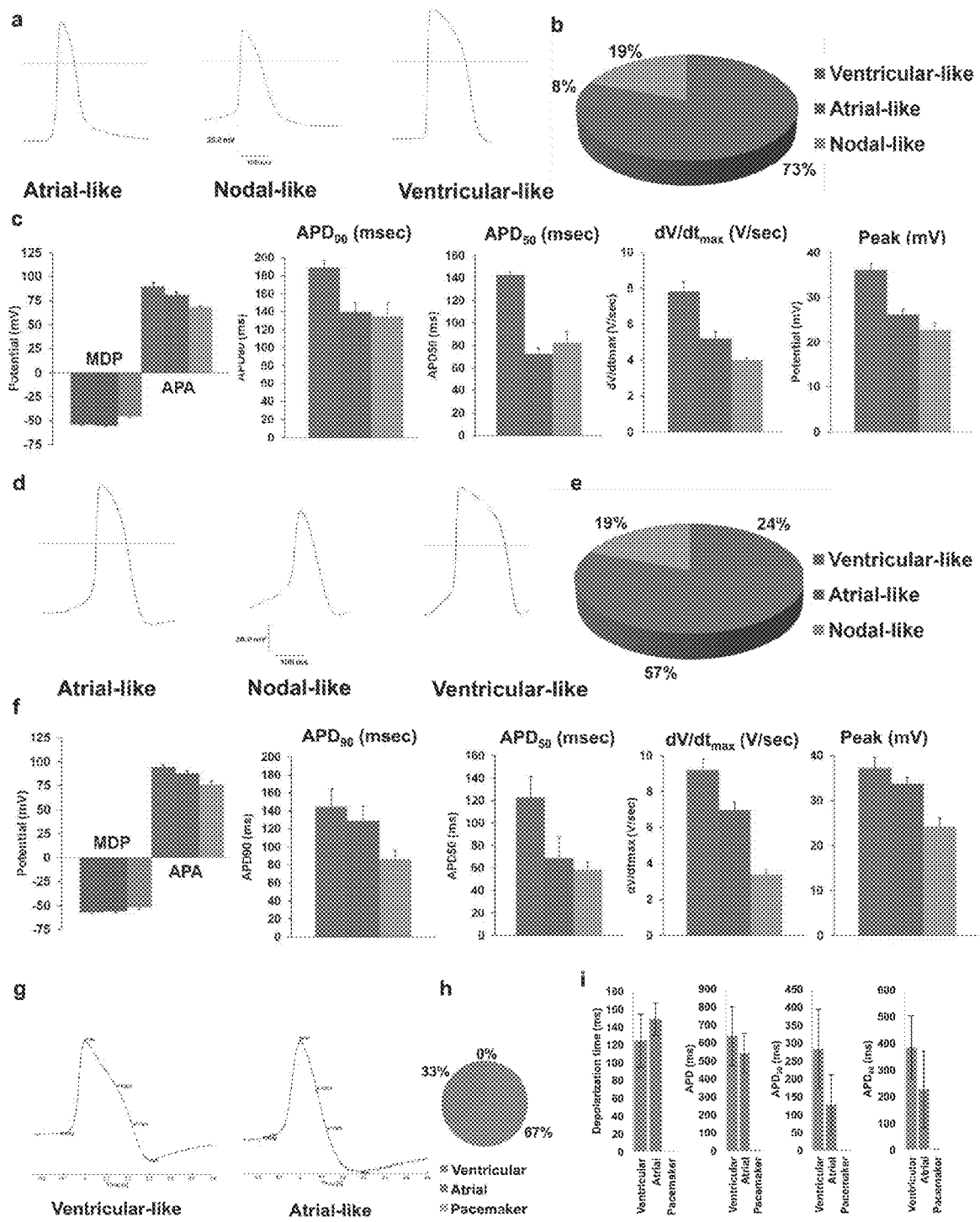
FIG. 6: Electrophysiological characterization of cardiomyocytes produced under chemically defined conditions. Action potential (AP) recordings using whole cell patch clamp of hiPSC-derived cardiomyocytes differentiation in CDM3 at day 15-d20 of differentiation. Cells exhibit AP morphologies that can be categorized as atrial-, nodal-, or ventricular-like. a) Representative trace of three cardiomyocyte subtypes produced. b) Proportions of cardiomyocyte subtypes at day 15-d20, n=26 c) The AP characteristics used to classify cells in to atrial-, nodal-, or ventricular-like. RMP (resting membrane potential), APA (action potential amplitude), AP duration at different levels of repolarization (i.e., 50 or 90%), $dV/dt_{max}$ (maximal rate of depolarization), and peak voltage. To determine the type of cardiomyocyte analyzed, APD90/50 values <1.4, designated ventricular-like cells, 1.4-1.7 designated nodal-like cells, and >1.7 designated atrial-like cells. d) Assessment of cells differentiated in CDM3 at day 30-d35 of differentiation, representative trace of three cardiomyocyte subtypes. e) Proportions of cardiomyocyte subtypes at day 15-d20, n=21 f) The AP characteristics used to classify cells in to atrial-, nodal-, or ventricular-like (as above). To determine the type of cardiac myocyte analyzed, APD90/50 values <1.4, designated ventricular cells, 1.4-1.7 designated nodal cells, and >1.7 designated atrial cells. g) Assessment of cells differentiated in CDM3 at day 30 differentiation using MEA-based nanopillar, representative trace of ventricular-like and atrial-like subtypes. h) Percentages of ventricular-like and atrial-like cells, n=20. i) Depolarization time, APD, action potential duration, AP duration at different levels of repolarization (i.e., 50 or 90%) used to classify cardiomyocyte subtype.

Finally, electrophysiological analysis was performed using two independent techniques. Patch clamp demonstrated that cells differentiated in CDM3 possessed a mixture of atrial, ventricular, and nodal phenotypes (FIG. 6a-b). Between days 15-20 of differentiation, cells differentiated in CDM3 were largely atrial-like with a fetal-like average maximum diastolic potential (MDP) of 55.2 mV (FIG. 6c-d). In contrast, at day 30-35 a greater proportion of cells demonstrated a ventricular phenotype (FIG. 6e-h). A second electrophysiological technique, nanopillar electroporation, was also used to further verify the cardiomyocyte electrophysiological properties. Vertical nanopillar electrodes can record both the extracellular and intracellular action potentials over a long period of time and it is possible to repeatedly switch between extracellular and intracellular recording by nanoscale electroporation and resealing processes[26]. The nanopillar demonstrated that day 30 cells possess a predominantly ventricular phenotype (FIG. 6i). Taken together, these electrophysiological analysis data were consistent with our flow cytometry (FIG. 5), immunofluorescence (FIG. 3a), and single cell realtime RT PCR (FIG. 4b) findings, demonstrating an immature atrial phenotype that progresses to a more ventricular phenotype.

Discussion

During these studies, we were surprised to find how few media components are required during the progression from pluripotent cell to cardiomyocyte. Of the 21 components in B27, only albumin was required and the simple CDM3 media consisting of 3 components (recombinant albumin, ascorbic acid, and RPMI 1640) supported cardiac differentiation at the same efficiency as RPMI+B27-ins. Albumin can fulfill multiple roles in media formulations, including acting as a detoxifier/buffer by binding lipids and excessive proteins, binding hormones and growth peptides to keep them stable, and binding free radicals to reduce oxidative damage to cells. In this protocol, we used a rice-derived recombinant albumin and can therefore rule out the presence of any contaminating mammalian albumin-associated proteins/lipids/small molecules. Intriguingly, removal of recombinant albumin in CDM3 did not result in cell death (as with removal of AA 2-P), but merely reduction in cardiomyocyte yield.

Ascorbic acid is an antioxidant with a well-established role in improving cardiac differentiation, which could be via increasing collagen synthesis resulting in greater proliferation of cardiovascular progenitor cells. The utility of ascorbic acid in E8 pluripotent media and during reprogramming raises the question of whether ascorbic acid is merely acting as an antioxidant in the cardiac differentiation system. It has recently been demonstrated that ascorbic acid produces widespread but targeted Tet-dependent DNA demethylation[30], and this demethylation may have a role during differentiation.

RPMI 1640 is one of the simplest classical basal media, related to McCoy's 5A and consists of 20 amino acids, inorganic salts, the eight B vitamins, and the antioxidant glutathione. RPMI 1640 does not contain any lipids, iron or zinc.

In the optimization of this system, we found that very tight specifications for pluripotent growth were required for successful subsequent differentiation, and from repeatedly differentiating eight hiPSC lines over >80 passages, it became clear that the pluripotent state governs the differentiation efficiency. A major issue in cardiac differentiation has been the demonstrated wide variation in efficiency between hiPSC lines and even at different passage numbers, requiring line-specific optimization of growth-factors and inhibitors of signaling pathways. It is also well established that pluripotent cell culture conditions can affect cardiomyocyte differentiation efficiency and yield. Two major advances in this area have been the development of a chemically defined medium for hiPSC culture (E8), and the development of synthetic and recombinant matrices replacing mouse sarcoma-derived Matrigel. Together, these advances eliminate many of the variables of pluripotent culture. Substantial progress has also been made in our understanding of the requirements to maintain pluripotency using a simple combination of FGF2 and insulin signaling through the PI3K/Akt pathway and TGFβ induction of SMAD2/3. The next inevitable step will be the development of a protein/growth factor-free hiPSC culture medium replacing FGF2 and TGFβ1 (and transferrin) with small molecules. The use of small molecules to maintain long-term pluripotent growth may alleviate some of the variation that is still present in pluripotent culture.

Experiments analyzing requirements for BMP, activin/NODAL, TGFβ, and FGF signaling pathways (FIG. 2) demonstrated the continued presence of a paracrine-dependent mesoderm inductive loop initiated by CHIR99021 treatment. The matrix to which the pluripotent cells are attached plays an integral role in differentiation. In our study, recombinant laminin-521 and truncated recombinant laminin-511 were found to be most successful for the support of pluripotent hiPSC growth and long-term adherence of CMs. It has been demonstrated that hESC-derived cardiomyocytes express integrin α3, α5, α6, α7, αV, β1, and β5, very similar to the predominant expression of α5, α6, αV, β1, and β5 in pluripotent hESCs. hESCs adhere to both laminin-511/-521 and Matrigel using the α6β1 integrin, likely explaining the similar long-term adherence performance. In contrast, pluripotent cells adhere to vitronectin using αVβ5 integrin. It has been suggested that αVβ5 has a substantially lower binding affinity for its preferred substrates than does α6β1, which may account for the differences noted between long-term cardiomyocyte adherence on the two matrices, or that hiPSC-derived cardiomyocytes may express lower levels of αVβ5 than hiPSCs. The costs of recombinant laminins are significant, and integrin α6β1 binding laminin-521 synthetic peptides may provide a better solution, building on the promising work that has been done on laminin peptides and hESC growth. Despite expanding research on polymer-based cell culture surfaces, which offer the greatest potential for cost reduction, it has been difficult to rule out the absorption of albumin/proteins from the media onto the surface as a crucial facilitator of cell adhesion. These surfaces have not yet been demonstrated to function with E8.

This chemically defined differentiation methodology provides a much needed reproducibility in hiPSC cardiomyocytes required in sensitive disease modeling applications. Scalability has also been a major issue in cardiac differentiation. Our optimizations reduced E8 media costs significantly; the costs of small molecules for cardiac induction were negligible. These reduced costs indicate that this formula can also be suitable for suspension-based pluripotent culture and differentiation. Finally, as CDM3 medium is highly defined, it will also help facilitate the transfer of basic research on human pluripotent stem cells to the clinic and provide significant insight into the macromolecular requirements of cardiovascular progenitor cells and hiPSC-derived cardiomyocytes.

Methods.

All pluripotent and reprogramming cultures were maintained at 37° C. in a New Brunswick Galaxy 170R humidified incubator (Eppendorf, Enfield, Conn., USA) with 5% $CO_2$ and 5% $O_2$ controlled by the injection of carbon dioxide and nitrogen. All primary cell and differentiation cultures were maintained at 5% $CO_2$ and atmospheric (21%) $O_2$.

Human induced pluripotent cell derivation. Following protocols were approved by the Stanford University Human Subjects Research Institutional Review Board. With informed written consent, two 2 mm skin punch biopsies were taken from each volunteer, diced with a scalpel, digested with 1 mg/mL collagenase IV (Life Technologies, Carlsbad, Calif., USA) for 2 h at 37° C. Fibroblasts were then grown in DMEM with GlutaMAX (Life Technologies) supplemented with 10% fetal bovine serum (FBS, US origin, Life Technologies) on 6-well plates (Greiner, Monroe, N.C., USA) coated with a 1:200 dilution of growth-factor reduced Matrigel (9 g/cm$^2$, Corning, Corning, N.Y., USA). Media was changed every other day. When confluent, fibroblasts were passaged with TrypLE Express (Life Technologies) on to Matrigel-coated T225 flasks (ThermoFisher Scientific/Nalge Nunc. Waltham, Mass., USA).

For Sendai reprogramming, early passage (p2-p3) fibroblasts were seeded at 40,000 cells per well on Synthemax II-SC (625 ng/cm$^2$, Corning) coated 6-well plates in E8. The E8 formula was modified to replace human-derived transferrin with an *Oryza sative*-derived recombinant version to make the formula completely chemically defined. The successful application of Synthemax II-SC at the low concentration of 625 ng/cm$^2$ is in line with reports that the minimal surface density of vitronectin protein is very low at 250 ng/cm$^2$. E8 was made in-house consisting of DMEM/F12 (10-092-CM, Corning), 20 µg/mL *E. coli*-derived recombinant human insulin (Dance Pharmaceuticals/CS Bio, Menlo Park, Calif., USA), 64 µg/mL L-ascorbic acid 2-phosphate sesquimagnesium salt hydrate (Sigma-Aldrich, St Louis, Mo., USA), 10.7 µg/mL *Oryza sativa*-derived recombinant human transferrin (Optiferrin, Invitria/Sigma-Aldrich), 14 ng/mL sodium selenite (Sigma-Aldrich), 100 ng/mL recombinant human FGF2 (154 amino acid. *E. coli*-derived, Peprotech, Rocky Hill, N.J., USA), and 2 ng/mL recombinant human TGFβ1 (112 amino acid, *E. coli*-derived, Peprotech). After 24 h, media was changed to fresh E8 and supplemented with four SOKM CytoTune Sendai viral particle reprogramming factors (Life Technologies) diluted 1/10 based on manufacturer's recommendations (10 µL of each per well). Media was changed after 24 h and thereafter once every day.

For the first 7 days, cultures were maintained in E8 supplemented with 100 nM hydrocortisone (Sigma-Aldrich) and 200 µM sodium butyrate (Sigma-Aldrich). At day 7, cells were passaged with TrypLE (Life Technologies) and seeded into 6 wells of a Synthemax II-SC-coated 6-well plate in E7N media (E8 minus TGFβ1; supplemented with 200 µM sodium butyrate). 2 µM thiazovivin (Selleck Chemicals, Houston, Tex., USA) was added for the first 24 h after passage. Media was changed every day then switched to E8 at day 20.

For plasmid-based reprogramming, pCXLE-hSK (27078), pCXLE-hUL (27080), and pCXLE-hOCT4-shp53 (27077) plasmids were obtained from Addgene (Cambridge, Mass., USA). The SOKM codon optimized mini-intronic plasmid (CoMiP) was generated by S. Diecke. Plasmid-containing *E. coli* were grown in Miller's LB (Life Technologies) and purified using Plasmid Maxi Kit (QIAGEN, Germantown, Md., USA) following manufacturer's instructions and quantified using a NanoDrop 2000 (ThermoFisher Scientific). 1×10$^6$ cells were electroporated with 6 µg total DNA (2 µg of each for 3 plasmid-based systems, 6 µg for CoMiP) using a Neon Transfection System (Life Technologies), using the settings 1650 V, 3 pulses, 10 ms, and 100 µL tips, with Buffers R and E2. Cells were plated on Synthemax II-SC-coated (625 ng/cm$^2$) 1×100 mm plates.

For peripheral blood mononuclear cell (PBMC) reprogramming 20 mL of blood was collected in EDTA-containing Vacutainer tubes, and PBMCs were isolated using a Ficoll-Paque PLUS (1.077 g/mL) gradient (GE Healthcare, Waukesha, Wis., USA) and plated at 1 million cells per mL in a humanized version of blood media$_6$ comprised of IMDM/F12 (Life Technologies), 2 mg/mL recombinant human albumin, 1% v/v chemically defined lipid concentrate (Life Technologies), 10 µg/mL recombinant human insulin, 100 µg/mL recombinant human transferrin. 15 ng/mL sodium selenite, 64 µg/mL L-ascorbic acid 2-phosphate, 450 µM 1-thioglycerol (Sigma-Aldrich), 100 ng/mL SCF (Peprotech), 10 ng/mL IL3 (Peprotech), 2 U/mL EPO (R&D Systems, Minneapolis, Minn., USA), 40 ng/mL IGF1 (Peprotech) and 1 µM dexamethasone (Sigma-Aldrich). Cells were cultured for 9 days with media changes every other day by centrifugation. After 9 days, 1×10$^6$ cells were plated per well in a 6-well Synthemax IISC-coated plate in blood media with Sendal virus as above. Media was changed every other day and switched to E7N at d7.

For all reprogramming methods, individual colonies with hESC morphology were picked into a well of a 12-well plate (1 colony per well) at d17-d25 in E8 with 2 µM thiazovivin for 24 h after picking. Subsequently cells were expanded in to 6-well plates by passaging 1:1, 1:3, 1:6, and finally 1:12 using 0.5 mM EDTA (Life Technologies) in D-PBS without Ca$^{2+}$/Mg (Life Technologies) for 7 min at RT.

Human pluripotent stem cell culture. Cells were routinely maintained in E8 (made in-house as above) on either Synthemax II-SC (625 ng/cm$^2$) or 1:200 growth factor-reduced Matrigel (9 μg/cm$^2$) and passaged every four days using 0.5 mM EDTA (as above). Cells were frozen in E8+10% dimethyl sulfoxide (EMD Millipore, Philadelphia, Pa., USA). hESC lines H7 (WA07) and H9 (WA09)$_7$ were supplied by WiCell Research Institute (Madison, Wis., USA). All hESCs and iPSCs were converted to E8/EDTA-based culture for at least 5 passages before beginning differentiation. Comparable cells were grown in mTeSR1 (Stemcell Technologies, Vancouver, BC, Canada). Cell lines were used between passages 20 and 85. All cultures (primary, pluripotent and differentiation) were maintained with 2 mL media per 10 cm$^2$ of surface area or equivalent. All cultures were routinely tested for mycoplasma using a MycoAlert Kit (Lonza, Allendale, N.J., USA).

Growth assays. To assess cell growth, cells were counted using a Countess automated cell counter (Life Technologies). For growth rate calculation, cells were seeded at 1.25×10$^4$ cells per cm$^2$ (120,000 cells per well of a 6-well plate) and grown for 96 h. Cumulative population doublings was calculated using the formula n=3.32 [log$_{10}$(N/N$_0$)].

Teratoma analysis. Three confluent wells of pluripotent cells were dissociated with 0.5 mM EDTA, centrifuged at 200 g for 4 min, re-suspended in 100 μL of growth factor-reduced Matrigel, and injected into the kidney capsule of female NOD-SCID mice (NOD.CB17-Prkd$_{Cscid}$/NcrCrl Strain code 394, Charles River, Wilmington, Mass., USA). After 4-6 weeks, teratomas were removed, fixed in 4% PFA, embedded in paraffin wax, sectioned and hematoxylin and eosin stained by the Stanford Tissue Bank. Slides were imaged and analyzed by a qualified clinical pathologist.

SNP karyotyping. A single well of >p20 pluripotent cells was dissociated with 0.5 mM EDTA, centrifuged at 200 g for 4 min, and the pellet was snap frozen in liquid nitrogen and stored at −80° C. Genomic DNA was extracted from the cell pellets using a Blood and Tissue DNA extraction kit (QIAGEN) following the manufacturer's directions. SNP karyotyping was performed using a Genome-Wide CytoScan HD Array (Affymetrix, Santa Clara, USA) covering 2.7 million markers and 750,000 SNPs and was analyzed using Chromosome Analysis Suite (ChAS, Affymetrix).

Cardiac differentiation of hiPSCs. hiPSCs and hESCs (>p20) were split at 1:10 or 1:12 ratios using EDTA as above and grown for 4 days at which time they reached ~85% confluence. Media was changed to CDM3, consisting of RPMI 1640 (11875, Life Technologies), 495 μg/mL *Oryza sativa*-derived recombinant human albumin (A0237, Sigma-Aldrich, 75 mg/mL stock solution in dH$_2$O, stored at −20° C.), 213 μg/mL L-ascorbic acid 2-phosphate (Sigma-Aldrich, 64 mg/mL stock solution in dH$_2$O, stored at −20° C.). Media was changed every other day (48 h). For d0-d2, media was supplemented with 6 μM CHIR99021 (LC Laboratories, Woburn, Mass., USA). On d2, media was change to CDM3 supplemented with 2 M Wnt-C59 (Cellagentech, San Diego, Calif., USA). Media was changed on d4 and every other day for CDM3. Contracting cells were noted from d7.

Other additions to cardiac differentiation media tested were 10.7 μg/mL recombinant human transferrin, 14 μg/mL sodium selenite, 1 μg/mL linoleic acid, 1 μg/mL linolenic acid, 2 ng/mL triiodo-l-thyronine, 2 μg/mL L-carnitine, 1 μg/mL D,L-alpha-tocopherol acetate, 100 ng/mL retinol acetate, 1 μg/mL ethanolamine, 20 ng/mL corticosterone, 9 ng/mL progesterone, 47 ng/mL lipoic acid, 100 ng/mL retinol, 1 μg/mL D,L-alpha-tocopherol, 100 ng/mL biotin, 2.5 ug/mL catalase, 2.5 μg/mL glutathione, 2.5 μg/mL superoxide dismutase, 2 μg/mL L-carnitine, 15 μg/mL D(+)-galactose, 16.1 μg/mL putrescine, 450 μM 1-thioglycerol, 55 μM 2-mercaptoethanol, 64 μg/mL L-ascorbic acid 2-phosphate (all from Sigma-Aldrich).

Basal media assessed were DMEM (catalogue #11965), DMEM/F12 (11330), IMDM (12440), IMDM/F12 (12440/11765), RPMI 1640 (11875), McCoy's 5A (16600), M199 (with Earle's Salts, 11150), MEMα (with Earle's Salts, no nucleosides, 12561), and MEM (with Earle's Salts, 11095) (all from Life Technologies). RPMI 1640 media assessed were RPMI 1640 with L-glutamine (catalogue number 11875), RPMI 1640 with L-glutamine and HEPES (22400), RPMI 1640 with GlutaMAX (61870), and RPMI with GlutaMAX and HEPES (72400) (all from Life Technologies).

Albumin sources assessed were human serum albumin (A1653, Sigma-Aldrich), *Oryza sativa*-derived recombinant human albumin (A0237, Sigma-Aldrich), *Saccharomyces cerevisiae* derived recombinant Albucult (Novozymes Biopharma/A6608, Sigma Aldrich). *Oryza sativa* derived recombinant Cellastim (Invitria/A9731, Sigma Aldrich), and embryo-grade bovine serum albumin (A3311, Sigma Aldrich).

Wnt inhibitors assessed were IWP-2, IWR-1 (Sigma-Aldrich), XAV-939, ICG-001 (Selleck Chemicals), IWP-4 (Stemgent, Cambridge, Mass., USA), and Wnt-C59 (Cellagentech). GSK3B inhibitors assessed were CHIR99021 (LC Laboratories), BIO, TWS119 (Selleck Chemicals), 1-azenkenpaullone, TDZD-8, ARA014418, and 3F8 (all Sigma-Aldrich). Inhibitors used for pathway analysis were PD173074, SB203580, LDN193189, SB431542 (all Selleck Chemicals), SU5402, Dorsomorphin, A83-01 (Tocris, Bristol, UK), ALK5 inhibitor (Stemgent), and ITD-1 (Xcessbio, San Diego, Calif., USA). All small molecules were re-suspended to 10 mM in dimethyl sulfoxide (DMSO).

For control treatments (0 μM) 0.1% DMSO was used. Comparisons were made to RPMI+B27-ins consisting of RPMI 1640 (11875) supplemented with 2% B27 without insulin (0050129SA, Life Technologies), StemPro-34 (Life Technologies) supplemented as shown in Table 5. LI-APEL low insulin media and Xeno-free Differentiation Medium were made as described.

Matrices. The following matrices were assessed for the ability to support pluripotent growth and subsequent cardiac differentiation: 9 μg/cm$^2$ Growth-factor reduced Matrigel (1:200, Corning) in DMEM/F12; 625 ng/cm$^2$ vitronectin peptide (Synthemax II-SC, Corning) in ultrapure water (1:50 also tested); 1 μg/cm$^2$ full length recombinant human vitronectin (1:50, Primorigen, Madison, Wis., USA) in D-PBS with Mg$^{2+}$ and Ca$^{2+}$; 2.5 μg/cm$^2$ laminin-521 (1:80, Biolamina, Stockholm, Sweden) in DPBS; 2 μg/cm$^2$ truncated recombinant human laminin-511 iMatrix-511 (1:50, Iwai North America, Foster City, Calif., USA) in DPBS; 1 μg/cm$^2$ rH E-cadherin (1:25, StemAdhere, Primorigen/Stemcell Technologies); 10 μg/cm$^2$ fibronectin (1:20, EMD Millipore) in DPBS. All were used at 2 mL per well of a 6-well (9.6 cm$_2$). Matrices were assessed on both 6-well polystyrene tissue culture plates and untreated plates (both from Greiner). Also tested were Synthemax-T 6-well plates and fibronectin mimetic plates (both from Corning) and 10 μg/cm$^2$ Pronectin (Sigma-Aldrich).

In vitro purification of cardiomyocytes. To purify cardiomyocytes, a variant of RPMI 1640 without D-glucose (11879, Life Technologies) was used in the media formula. RPMI without D glucose was supplemented with 213 μg/mL L-ascorbic acid 2-phosphate (Sigma-Aldrich), 495 μg/mL *Oryza sativa*-derived recombinant human albumin (Sigma- Aldrich), and 5 mM sodium DL-lactate (L4263, Sigma-Aldrich, equal to ~4 mM lactate) and used in place of CDM3 on differentiation days 10-20. Cryopreservation of purified cardiomyocytes. Differentiation day 15 cardiomyocytes were treated with TrypLE for 10 min at 37° C. and triturated with a P1000 tip. Cells were filtered through a 100 μM cell strainer (BD Biosciences), counted using a Countess Cell Counter (Life Technologies) and cryopreserved at 2-50 million cells per vial in CDM3+10% DMSO.

Immunofluorescence for pluripotency. For assessment of pluripotency, cells were passaged with EDTA and plated onto Synthemax II-SC-coated (625 ng/cm$^2$) Lab-Tek II 8-chamber glass slides (154524, ThermoFisher Scientific/Nunc) in E8 and allowed to grow for 3 days. Cells were fixed with 4% PFA (Electron Microscopy Services, Hatfield, Pa., USA) for 15 min at RT, permeabilized with 0.1% Triton-X (Sigma-Aldrich) for 10 min at RT, blocked in 10% goat serum (Sigma-Aldrich), 0.1% Triton-X for 15 min at RT and stained with 1:200 mouse IgM TRA-1-60 (09-0010), 1:200 mouse IgM TRA-1-80 (09-0012). 1:200 mouse IgG$_3$ SSEA4 (09-0006, all Stemgent), 1:200 rabbit IgG POU5F1 (sc-9081), 1:200 rabbit IgG NANOG (sc-33759, both Santa Cruz Biotechnology, Santa Cruz, Calif., USA), or 1:200 rabbit IgG SOX2 (651901, Biolegend, San Diego, Calif., USA) in D-PBS overnight at 4° C. Cells were washed and then stained with secondary antibodies 1:1000 Alexa Fluor 488 goat anti-mouse IgM (μ chain), 1:1000 Alexa Fluor 488 goat anti-mouse IgG (H+L), or 1:1000 Alexa Fluor 594 goat anti-rabbit IgG (H+L) (all Life Technologies) in D-PBS for 30 min at RT in the dark. Nuclei were stained with NucBlue Fixed Cell Stain (Life Technologies) and coverslips were attached to the slides with Vectashield (Vectorlabs, Burlingame, Calif., USA). Slides were imaged with a Leica DM IL LED inverted fluorescent microscope (Leica, Wetzlar, Germany) at 40× and LAS software and processed using Volocity 6.0 (PerkinElmer, Waltham, Mass., USA).

Immunofluorescence for cardomyocyte markers. Cells at d15-d60 were dissociated using TrypLE Express for 10 min at 37° C., triturated, centrifuged at 200 g for 4 min, plated onto Synthemax II-SC-coated (625 ng/cm$^2$) coverslips in CDM3 and allowed to adhere for 3-5 days. Cells were then processed as above and stained with 1:200 mouse monoclonal IgG$_1$ TNNT2 (13-11, ThermoFisher Scientific Lab Vision, Kalamazoo, Mich., USA), 1:400 mouse monoclonal IgG$_{2b}$ MLC2A (MYL7, Synaptic Systems, Goettingen, Germany), 1:200 rabbit polyclonal IgG MLC2V (MYL2, ProteinTech, Chicago, Ill., USA), 1:50 mouse monoclonal IgG$_1$ P4HB (Abcam, Cambridge, UK), 1:400 mouse monoclonal IgG$_{2a}$ SMA (Sigma-Aldrich, St. Louis, Mo., USA), 1:400 rabbit polyclonal IgG vWF (Abcam), and 1:500 rabbit polyclonal IgG Ki67 (Thermo Scientific Lab Vision). Cells were washed 4 times, for 10 min, with 1% BSA in PBS-T and then incubated for 1 hour at RT in the dark with 1:400 Alexa Fluor secondary antibodies (Life Technologies) diluted in 2% BSA. Cells were washed again as above and mounted with Slow-Fade Gold Antifade Reagent with DAPI (Life Technologies) onto Superfrost Plus (VWR) slides and imaged with an LSM510Meta Confocal Microscope (Zeiss).

Flow cytometry. For optimization of cardiac differentiation conditions, cells were cultured in 12-well plates. For analysis of cardiomyocyte differentiation efficacy and subtype specification, expression of TNNT2, MLC2A and MLC2V was analyzed by flow cytometry. At d14-15 of differentiation, the entire well was dissociated with TrypLE Express for 10 min at 37° C. and transferred to flow cytometry tubes (BD Biosciences). Cells were then fixed with 1% PFA for 15 min, permeabilized with 90% methanol for 15 min and stained using 1:200 mouse monoclonal IgG1 TNNT2 (13-11, Thermo Scientific), 1:400 mouse monoclonal IgG2b MLC2A (MYL7, Synaptic Systems) and 1:200 rabbit polyclonal IgG MLC2V (MYL2, ProteinTech) for 45 min at RT. Secondary staining was performed with 1:1000 Alexa Fluor 488 goat anti-mouse IgG1, 1:1000 Alexa Fluor 488 goat anti-rabbit IgG (H+L), 1:1000 Alexa Fluor 647 goat anti-mouse IgG2b and 1:1000 Alexa Fluor 647 goat anti-rabbit IgG (H+L) secondary antibodies for 20 min. These conditions were shown to stain negative on human skin fibroblasts. Cells were analyzed using a FACSAria II (BD Biosciences) with a 100 μM nozzle and FACSDiva software. Data were analyzed using FlowJo 8.7 (Tree Star).

Quantitative real-time polymerase chain reaction. To analyze gene expression, cells were dissociated with TryPLE Express for 10 min at 37° C., triturated and diluted in CDM3 and centrifuged at 200 g for 4 min. Media was aspirated and pellets of cells were snap frozen in liquid nitrogen and stored at −80° C. RNA was isolated using an RNeasy Plus kit (QIAGEN), cDNA produced using a High Capacity RNA-to-cDNA kit (Life Technologies), and Real-time PCR was performed using TaqMan Gene Expression Assays, TaqMan Gene Expression Master Mix and a 7900HT Real-Time PCR System (all Life Technologies). All PCR reactions were performed in triplicate, normalized to the 18S endogenous control gene and assessed using the comparative $C_t$ method.

Single cell quantitative real-time polymerase chain reaction. To analyze single cell gene expression, cells were dissociated as above and a 300,000 cells/mL suspension was prepared. 11 The cell suspension was loaded onto a 17-25 μm $C_1$ Fluidigm chip for single-cell capture (Fluidigm, South San Francisco, Calif., USA) and treated with LIVE/DEAD Viability/Cytotoxicity Kit (Life Technologies). The $C_1$ chip was then imaged under phase-contrast and fluorescence microscopes to exclude doublets and dead cells from subsequent PCR analysis. Single-cell lysis, reverse transcription, and pre-amplification were all performed on the $C_1$ chip using the $C_1$ Single Cell Auto Prep (Fluidigm) and Single Cell-to-CT kits (Ambion). Reverse transcription was performed at 25° C. for 10 min, 42° C. for 1 hour and finally 85° C. for 5 min. Preamplification was at 95° C. for 10 min, followed by 18 cycles of 95° C. for 15 sec, and 60° C. for 4 min. Amplified cDNA products were harvested from the $C_1$ chip into 96-well 0.2 mL PCR plates and then loaded onto Biomark 48.48 Dynamic Array chips using the Nanoflex IFC controller (Fluidigm). Quantitative single cell PCR was performed using gene amplification with TaqMan Assays (Life Technologies) and threshold cycle ($C_t$) as a measurement of relative fluorescence intensity was extracted by the BioMark Real-Time PCR Analysis software. All PCR reactions were performed in duplicates or triplicates, and CT values were directly used in data analysis after normalization to the 18S endogenous control gene.

Patch clamp. To record cellular action potentials, cardiomyocytes at d15 were dissociated using TrypLE for 10 min, filtered through a 100 μM cell strainer (BD Biosciences), counted with a Countess Cell Counter and plated as single cells (1×10$^5$ cells per well of a 24-well plate) on No. 1 8 mm glass cover slips (Warner Instruments, Hamden, Conn., USA) coated with Synthemax IISC (650 ng/cm$^2$) in CDM3 supplemented with 2 μM thiazovivin and allowed to attach for 72 h, changing the media every other day. Cells were then subjected to whole-cell patch-clamp at 36-37° C. using an EPC-10 patch-clamp amplifier (HEKA, Lambrecht, Germany) attached to a RC12 26C recording chamber (Warner) and mounted onto the stage of an inverted microscope (Nikon. Tokyo, Japan). Sharp microelectrodes were fabricated from standard wall borosilicate glass capillary tubes (Sutter BF 100-50-10, Sutter Instruments) using a P-97 Sutter micropipette puller to generate electrodes with tip resistances between 50 and 70 MΩ when backfilled with 3 M KCl. Cell cultures were perfused with warm (35-37° C.) Tyrode's solution consisting of (mM) 135 NaCl, 5.4 KCl, 1.8 $CaCl_2$, 1.0 $MgCl_2$, 0.33 $NaH_2PO_4$, 5 HEPES, and 5 glucose; pH was adjusted to 7.4 with NaOH. Membrane potential measurements were made using the current clamp mode of the Multiclamp 700B amplifier after electrode potential offset and capacitance were neutralized. Data were acquired using PatchMaster software (HEKA) and digitized at 1.0 kHz. Nanopillar action potential recordings. Before plating, nanopillar electrode devices$_{11}$ were cleaned with 5 minutes of oxygen plasma treatment. The culture chamber was coated with 9 μg/$cm_2$ Matrigel for 30-60 minutes. hiPSC-CMs were then plated at a density of 1×$10^5$ per cm in CDM3 or RPMI+B27-ins with 2 μM thiazovivin for the first 24 h. The cells were maintained in a standard incubator at 37° C. and 5% $CO_2$. Medium was changed every 24 h. 2-3 days after plating spontaneous and synchronous beating was observed. A 60-channel voltage amplifier system (Multichannel System, MEA1060-Inv-BC) was used for recording hiPSC-CM cells cultured on nanopillar electrode arrays (9 nanopillars per array) after cells started beating. Recording was performed in the same culture medium at room temperature using a Ag/AgCl electrode in the medium as the reference electrode. The amplification was 53 and the sampling rate was 5 kHz. For electroporation, 20 biphasic square pulses of 3.5 V amplitude and 400 μs period were applied to a nanopillar electrode. The recording system was blanked during the 13 electroporation period. Electrophysiology recordings were resumed 10-20 s after the electroporation to avoid amplifier saturation. Recordings were taken daily. The recordings were analyzed by a custom MATLAB code. Briefly, the first 20-30 intracellular recorded action potentials were overlayed and averaged. The action potential maximum and resting potentials were then identified. $APD_{50}$ and $APD_{90}$ were subsequently computed. Nanopillar electrode devices were reused after removal of the cells by TrypLE Express.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

That which is claimed is:

1. A method of producing a cardiomyocyte population from a human pluripotent stem cell population, the method comprising:
    (a) contacting the human pluripotent stem cell population with an effective amount of a Wnt signaling agonist in a minimal media for a period of about 12-60 hours, to produce an agonist-contacted cell population; and
    (b) contacting the agonist-contacted cell population with an effective amount of a Wnt signaling antagonist in a minimal media for a period of at least 12 hours
    wherein the minimal media is selected from the group consisting of: CDM3, D3 media, D4 media, and D11 media.

2. The method according to claim 1, wherein the Wnt signaling agonist is an inhibitor of GSK-3β.

3. The method according to claim 2, wherein the inhibitor of GSK-3β is BIO, CHIR-99021, or a combination thereof.

4. The method according to claim 1, wherein the Wnt signaling antagonist is a compound selected from the group consisting of: C59, IWR-1, IWP-2, IWP-4, XAV-939, and combinations thereof.

5. The method according to claim 4, wherein the Wnt signaling antagonist is C59.

6. The method according to claim 1, wherein the human pluripotent stem cell population is a population of embryonic stem cells or a population of induced pluripotent stem cells.

7. The method according to claim 1, wherein the minimal media is a chemically defined minimal media.

8. The method according to claim 7, wherein the chemically defined minimal media is CDM3 media.

9. The method according to claim 1, wherein prior to contact with the Wnt signaling agonist, the mammalian pluripotent stem cell population is cultured in maintenance media.

10. The method according to claim 9, wherein the maintenance media is supplemented with a ROCK inhibitor for a period of about 24 hours each time the human pluripotent stem cell population is passaged.

11. The method according to claim 1, wherein the human pluripotent stem cell population is cultured as a monolayer on a matrix.

12. The method according to claim 1, further comprising the step of verifying the presence of cardiomyocytes in the antagonist-contacted cell population.

13. The method according to claim 12, wherein verifying comprises one or more of: determining a cardiomyocyte electrophysiological profile; determining responsiveness of the antagonist-contacted cell population to known cardioactive drugs; or contacting the antagonist-contacted cell population with an antibody specific for a cardiomyocyte marker protein, and determining the percentage of cells positive for expression, wherein cells positive for expression are cardiomyocytes.

14. The method according to claim 12, wherein at least 80% of the cells of the antagonist-contacted cell population are determined to be cardiomyocytes.

15. The method according to claim 1, wherein cells are not contacted with the compounds SB431542, LY364947, dorsomorphin, LDN 193189, or SB203580.

16. The method according to claim 1, further comprising a step of contacting the antagonist-contacted cell population with a minimal media lacking glucose for a period of time sufficient to enrich the cell population for cardiomyocytes.

* * * * *